US011008370B2

(12) United States Patent
Sahni et al.

(10) Patent No.: US 11,008,370 B2
(45) Date of Patent: May 18, 2021

(54) GENETICALLY MODIFIED YEAST CELL AND IMPROVED PROCESS FOR PRODUCTION OF CLOT-SPECIFIC STREPTOKINASE

(71) Applicant: Council of Scientific & Industrial Research, New Delhi (IN)

(72) Inventors: Girish Sahni, Chandigarh (IN); Kishore Kumar Joshi, Chandigarh (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/771,127

(22) PCT Filed: Oct. 26, 2016

(86) PCT No.: PCT/IN2016/050363
§ 371 (c)(1),
(2) Date: Apr. 26, 2018

(87) PCT Pub. No.: WO2017/072791
PCT Pub. Date: May 4, 2017

(65) Prior Publication Data
US 2018/0362596 A1  Dec. 20, 2018

(30) Foreign Application Priority Data
Oct. 26, 2015 (IN) .......................... 3448/DEL/2015

(51) Int. Cl.
| | |
|---|---|
| C07K 14/315 | (2006.01) |
| C12N 15/81 | (2006.01) |
| A61P 7/02 | (2006.01) |
| A61K 9/00 | (2006.01) |
| C07K 14/78 | (2006.01) |
| A61K 38/00 | (2006.01) |
| G01N 33/569 | (2006.01) |

(52) U.S. Cl.
CPC ........ *C07K 14/3153* (2013.01); *A61K 9/0019* (2013.01); *A61P 7/02* (2018.01); *C07K 14/78* (2013.01); *C12N 15/81* (2013.01); *C12Y 304/21* (2013.01); *G01N 33/56961* (2013.01); *A61K 38/00* (2013.01)

(58) Field of Classification Search
CPC ...................................................... C12N 9/81
See application file for complete search history.

(56) References Cited

U.S. PATENT DOCUMENTS

| 7,163,817 B2 | 1/2007 | Sahni et al. | |
|---|---|---|---|
| 8,143,027 B2 | 3/2012 | Sahni et al. | |
| 2003/0059921 A1* | 3/2003 | Sahni ................. | C07K 14/3153 435/226 |
| 2008/0187940 A1 | 8/2008 | Lim et al. | |
| 2010/0034804 A1 | 2/2010 | Kumar et al. | |

FOREIGN PATENT DOCUMENTS

| EP | 0248227 A1 | 5/1987 |
|---|---|---|
| EP | 2684948 A1 | 1/2014 |
| WO | 2014208583 A1 | 12/2014 |

OTHER PUBLICATIONS

Pratap et al., "Characteristics of glycosylated streptokinase secreted from Pichia pastoris : enhanced resistance of SK to proteolysis by glycosylation", Appl Microbiol Biotechnol (2000) 53: 469-475.*
User Manual for Pichia Expression Kit, Invitrogen, Version L, 2000, pp. 1-73. Retrieved from <http://www.img.bio.uni-goettingen.de/ms-www/internal/methods/Yeast/PichiaExpression.pdf> on Oct. 9, 2019.*
Joshi & Sahni, "Molecular cloning, expression, purification and characterization of truncated forms of human plasminogen in Pichia pastoris expression system", Process Biochemistry, 2010, vol. 45, pp. 1251-1260.*
Castellino, "Recent Advances in the Chemistry of the Fibrinolytic System", American Chemical Society, Oct. 1981, vol. 81, No. 5, pp. 431-446.
Malke et al., "Streptokinase: Cloning, expression, and excretion by *Escherichia coli*", Proceedings of the National Academy of Sciences of the USA, vol. 81, No. 11, Jun. 1, 1984, pp. 3557-3561.
Malke et al., "Expression of a streptokinase gene from *Streptococcus equisimilis* in *Streptococcus sanguis*", Mol Gen Genet, 1984, pp. 360-363.
Grierson et al., "Pharmacokinetics of streptokinase in patients based on amidolytic activator complex activity", Division of Clinical Pharmacology and Cardiology, Dept. of Medicine, Duke Univ. Medical Center, vol. 41, No. 3, Sep. 2, 1986, pp. 304-313.
Cregg et al., "Pichia pastoris as a Host System for Transformations", Molecular and Cellular Biology, Dec. 1985, vol. 5, No. 12, pp. 3376-3385.
Simon et al., "A Rapid and Efficient Procedure for Transformation of Intact *Saccharomyces cerevisiae* by Electroporation", Biochemical and Biophysical Research Communications, Nov. 15, 1989, vol. 164, No. 3, pp. 1157-1164.
Orsonneau et al., "An Improved Pyrogallol Red-Molybdate Method for Determining Total Urinary Protein", Clin. Chem. 35/11, 1989, pp. 2233-2236.

(Continued)

*Primary Examiner* — Suzanne M Noakes
(74) *Attorney, Agent, or Firm* — Dinsmore & Shohl LLP

(57) ABSTRACT

Disclosed herein is an expression system for the production and secretion of biologically active clot-specific streptokinase (CSSK) protein in methylotrophic yeast. Yeast-expressed CSSK protein displays improved plasminogen activation and fibrin selectivity. Further disclosed are methylotrophic yeast transformed with at least one copy of functional cDNA sequence encoding CSSK adjunct with modified signal sequence which results in secretion of mature and correctly processed CSSK.

19 Claims, 25 Drawing Sheets

Specification includes a Sequence Listing.

(56) References Cited

OTHER PUBLICATIONS

Wong et al., "Engineering and Production of Streptokinase in a Bacillus Subtilis Expression-Secretion System", Applied and Environmental Microbiology, Feb. 1994, vol. 60, No. 2, pp. 517-523.

Hagenson et al., "Expression of Streptokinase in Pichia pastoris yeast", Enzyme Microb. Technol., vol. 11, Oct. 1989, pp. 650-656, USA.

Ito et al., "Transformation of Intact Yeast Cells Treated with Alkali Cations", Journal of Bacteriology, vol. 153, No. 1, 1983, American Society for Microbiology, pp. 163-168.

Gold et al., "Rapid and sustained coronary artery recanalization with combined bolus injection of recombinant tissue-type plasminogen activator and monoclonal antiplatelet GPIIb/IIIa antibody in a canine preparation", Laboratory Investigation, Coronary Thrombolysis, vol. 77, No. 3, Mar. 1988, http://ahajournals.org, pp. 670-677.

Rothstein, "One-Step Gene Disruption in Yeast", Cloning of Genes into Yeast Cells, Academic Press, Inc., 1983, Methods in Enzymology, vol. 101, ISBN 0-12-182001-7, pp. 202-211.

Cregg et al., "High-Level Expression and Efficient Assembly of Hepatitis B Surface Antigen in the Methylotrophic Yeast, *Pichia pastoris*", Nature Biotechnology, May 1987, vol. 5, pp. 479-485.

International Search Report and Written Opinion completed Mar. 7, 2017, pertaining to International Application No. PCT/IN2016/050363, filed Oct. 26, 2016, 11 pages.

\* cited by examiner

```
         AOX1 mRNA 5'end (824)                    5' AOX1 primer site (855-875)
 82  TTATCATCAT TATTAGCTTA CTTTCATAAT TGCGACTGGT TCCAATTGAC 87  AAGCTTTTGA TTTTAACGAC TTTTAACGAC AACTTGAGAA GATCAAAAAA
                                     Start (949)    α-Factor Signal Sequence
 92  CAACTAATTA TTCGAAGGAT CCAAACG ATG AGA TTT CCT TCA ATT
                                   Met Arg Phe Pro Ser Ile 96  TTT ACT GCA GTT TTA TTC GCA GCA TCC TCC GCA TTA GCT GCT
     Phe Thr Ala Val Leu Phe Ala Ala Ser Ser Ala Leu Ala Ala 100  CCA GTC AAC ACT ACA ACA GAA GAT GAA ACG GCA CAA ATT CCG
     Pro Val Asn Thr Thr Thr Glu Asp Glu Thr Ala Gln Ile Pro 105  GCT GAA GCT GTC ATC GGT TAC TCA GAT TTA GAA GGG GAT TTC
     Ala Glu Ala Val Ile Gly Tyr Ser Asp Leu Glu Gly Asp Phe 109  GAT GTT GCT GTT TTG CCA TTT TCC AAC AGC ACA AAT AAC GGG
     Asp Val Ala Val Leu Pro Phe Ser Asn Ser Thr Asn Asn Gly
                                    α-Factor primer site (1152-1172)
113  TTA TTG TTT ATA AAT ACT ACT ATT GCC AGC ATT GCT GCT AAA
     Leu Leu Phe Ile Asn Thr Thr Ile Ala Ser Ile Ala Ala Lys
                         XhoI          Kex2 signal cleavage        SnaBI
117  GAA GAA GGG GTA TCT CTC GAG AAA AGA GAG GCT GAA GCT TAC
     Glu Glu Gly Val Ser Leu Glu Lys Arg Glu Ala Glu Ala Tyr
        EcoRI     AvrII    NotI                      Ste13 signal cleavage
121  GTA GAA TTC CCT AGG GCG GCC GCG AAT TAA TTCGCCTTAG
     Val Glu Phe Pro Arg Ala Ala Ala Asn ***

125  ACATGACTGT TCCTCAGTTC AAGTTGGGCA CTTACGAGAA GACCGGTCTT
                          3' AOX1 primer site (1327-1347)
130  GCTAGATTCT AATCAAGAGG ATGTCAGAAT GCCATTTGCC TGAGAGATGC 135  AGGCTTCATT TTTGATACTT TTTTATTTGT AACCTATATA GTATAGGATT
                ↓ AOX1 mRNA 3' end (1418)
140  TTTTTTGTCA
```

FIG. 3

A
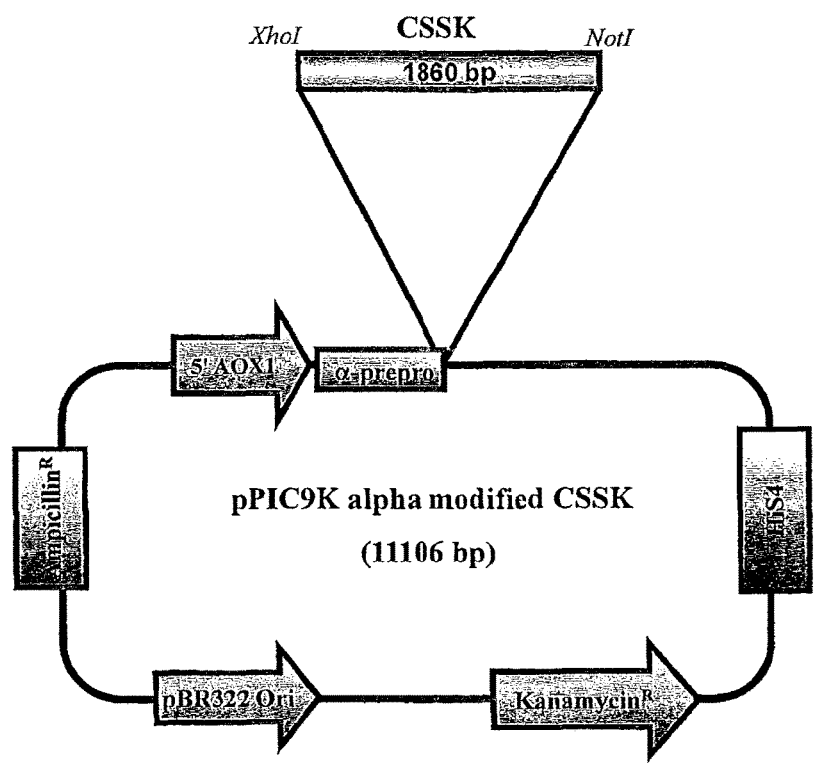
B
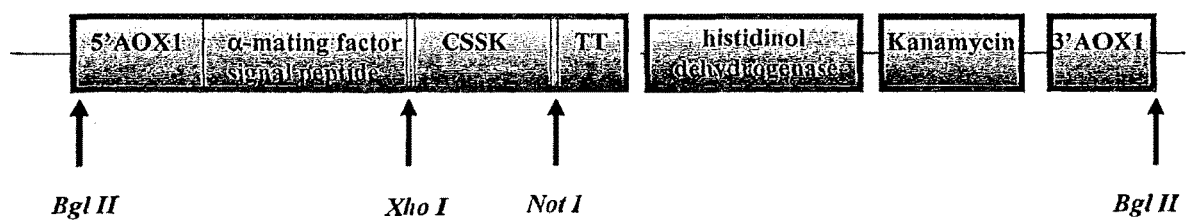
FIG. 6

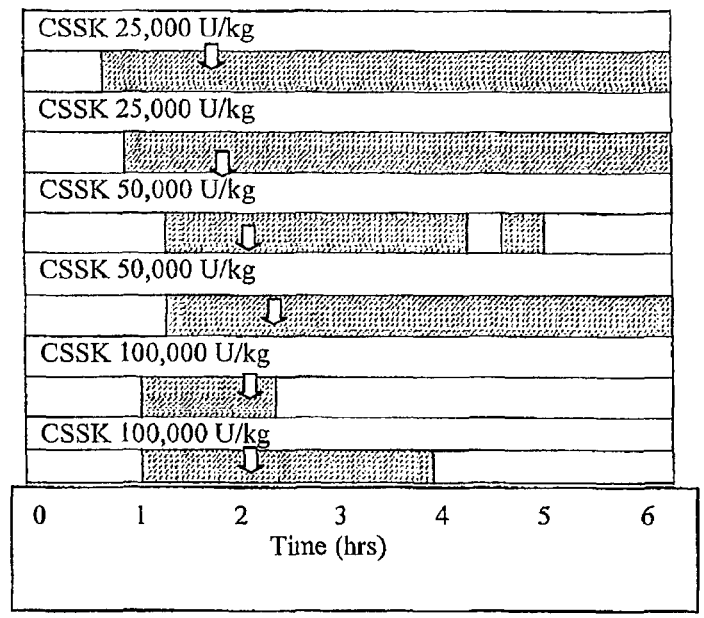
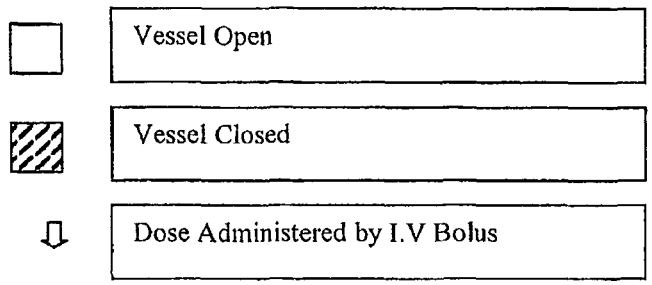
FIG. 21

SEQUENCE LISTING

```
<160> NUMBER OF SEQ ID NOS: 33

<210> SEQ ID NO 1
<211> LENGTH: 620
<212> TYPE: PRT
<213> ORGANISM: Artificial Sequence
<220> FEATURE:
<223> OTHER INFORMATION: CSSK amino acid

<400> SEQUENCE: 1

Met Val Gln Ala Gln Gln Ile Val Pro Ile Ala Glu Lys Cys Phe Asp
1               5                   10                  15

His Ala Ala Gly Thr Ser Tyr Leu Val Gly Glu Thr Trp Glu Lys Pro
            20                  25                  30

Tyr Gln Gly Trp Met Met Val Asp Cys Thr Cys Leu Gly Glu Gly Ser
        35                  40                  45

Gly Arg Ile Thr Cys Thr Ser Arg Asn Arg Cys Asn Asp Gln Asp Thr
    50                  55                  60

Arg Thr Ser Tyr Arg Ile Gly Asp Thr Trp Ser Lys Lys Asp Asn Arg
65                  70                  75                  80

Gly Asn Leu Leu Gln Cys Ile Cys Thr Gly Asn Gly Arg Gly Glu Trp
                85                  90                  95

Lys Cys Glu Arg His Thr Ser Val Gln Thr Thr Ser Ser Gly Ser Gly
            100                 105                 110

Pro Phe Thr Asp Val Arg Ile Ala Gly Pro Glu Trp Leu Leu Asp Arg
        115                 120                 125

Pro Ser Val Asn Asn Ser Gln Leu Val Val Ser Val Ala Gly Thr Val
    130                 135                 140
```

```
Glu Gly Thr Asn Gln Asp Ile Ser Leu Lys Phe Glu Ile Asp Leu
145                 150                 155                 160

Thr Ser Arg Pro Ala His Gly Lys Thr Glu Gln Gly Leu Ser Pro
            165                 170                 175

Lys Ser Lys Pro Phe Ala Thr Asp Ser Gly Ala Met Ser His Lys Leu
            180                 185                 190

Glu Lys Ala Asp Leu Leu Lys Ala Ile Gln Glu Gln Leu Ile Ala Asn
            195                 200                 205

Val His Ser Asn Asp Asp Tyr Phe Glu Val Ile Asp Phe Ala Ser Asp
    210                 215                 220

Ala Thr Ile Thr Asp Pro Asn Gly Lys Val Tyr Phe Ala Asp Lys Asp
225                 230                 235                 240

Gly Ser Val Thr Leu Pro Thr Gln Pro Val Gln Glu Phe Leu Leu Ser
            245                 250                 255

Gly His Val Arg Val Arg Pro Tyr Lys Glu Lys Pro Ile Gln Asn Gln
            260                 265                 270

Ala Lys Ser Val Asp Val Glu Tyr Thr Val Gln Phe Thr Pro Leu Asn
            275                 280                 285

Pro Asp Asp Asp Phe Arg Pro Gly Leu Lys Asp Thr Lys Leu Leu Lys
290                 295                 300

Thr Leu Ala Ile Gly Asp Thr Ile Thr Ser Gln Glu Leu Leu Ala Gln
305                 310                 315                 320

Ala Gln Ser Ile Leu Asn Lys Asn His Pro Gly Tyr Thr Ile Tyr Glu
            325                 330                 335

Arg Asp Ser Ser Ile Val Thr His Asp Asn Asp Ile Phe Arg Thr Ile
            340                 345                 350

Leu Pro Met Asp Gln Glu Leu Ser Tyr Arg Val Lys Asn Arg Glu Gln
            355                 360                 365

Ala Tyr Arg Ile Asn Lys Lys Ser Gly Leu Asn Glu Glu Ile Asn Asn
            370                 375                 380

Thr Asp Leu Ile Ser Glu Lys Tyr Tyr Val Leu Lys Lys Gly Glu Lys
385                 390                 395                 400

Pro Tyr Asp Pro Phe Asp Arg Ser His Leu Lys Leu Phe Thr Ile Lys
            405                 410                 415

Tyr Val Asp Val Asp Thr Asn Glu Leu Leu Lys Ser Glu Gln Leu Leu
            420                 425                 430

Thr Ala Ser Glu Arg Asn Leu Asp Phe Arg Asp Leu Tyr Asp Pro Arg
            435                 440                 445

Asp Lys Ala Lys Leu Leu Tyr Asn Asn Leu Asp Ala Phe Gly Ile Met
450                 455                 460

Asp Tyr Thr Leu Thr Gly Lys Val Glu Asp Asn His Asp Thr Asn
465                 470                 475                 480

Arg Ile Ile Thr Val Tyr Met Gly Lys Arg Pro Glu Gly Glu Asn Ala
            485                 490                 495

Ser Tyr His Leu Ala Gly Gly Gln Ala Gln Ile Val Pro Ile
            500                 505                 510

Ala Glu Lys Cys Phe Asp His Ala Ala Gly Thr Ser Tyr Leu Val Gly
            515                 520                 525

Glu Thr Trp Glu Lys Pro Tyr Gln Gly Trp Met Met Val Asp Cys Thr
            530                 535                 540

Cys Leu Gly Glu Gly Ser Gly Arg Ile Thr Cys Thr Ser Arg Asn Arg
545                 550                 555                 560

Cys Asn Asp Gln Asp Thr Arg Thr Ser Tyr Arg Ile Gly Asp Thr Trp
```

|  |  | 565 |  |  |  | 570 |  |  |  | 575 |  |
| --- | --- | --- | --- | --- | --- | --- | --- | --- | --- | --- | --- |
| Ser | Lys | Lys | Asp | Asn | Arg | Gly | Asn | Leu | Leu | Gln | Cys | Ile | Cys | Thr | Gly |
|  |  |  | 580 |  |  |  | 585 |  |  |  | 590 |

Asn Gly Arg Gly Glu Trp Lys Cys Glu Arg His Thr Ser Val Gln Thr
     595              600              605

Thr Ser Ser Gly Ser Gly Pro Phe Thr Asp Val Arg
   610              615             620

<210> SEQ ID NO 2
<211> LENGTH: 1860
<212> TYPE: DNA
<213> ORGANISM: Artificial Sequence
<220> FEATURE:
<223> OTHER INFORMATION: CSSK nucleuic acid

<400> SEQUENCE: 2

```
gtgcaagctc aacaaattgt gcccatagct gagaagtgtt ttgatcatgc tgctgggact      60
tcctatttgg tcggagaaac gtgggagaag ccctaccaag ctggatgat  ggtagattgt     120
acttgcctgg gagaaggcag cggacgcatc acttgcactt ctagaaatag atgcaacgat    180
caggacacaa ggacatccta tagaattgga gacacctgga gcaagaagga taatcgagga    240
aacctgctcc agtgcatctg cacaggcaac ggccgaggag agtggaagtg tgagaggcac    300
acctctgtgc agaccacatc gagcggatct ggcccttca ccgatgttcg tattgctgga    360
cctgagtggc tgctagaccg tccatctgtc aacaacagcc aattagttgt tagcgttgct    420
ggtactgttg aggggacgaa tcaagacatt agtcttaaat ttttgaaat cgatctaaca    480
tcacgacctg ctcatggagg aaagacagag caaggcttaa gtccaaaatc aaaccatt    540
gctactgata gtggcgcgat gtcacataaa cttgagaaag ctgacttact aaaggctatt    600
caagaacaat tgatcgctaa cgtccacagt aacgacgact actttgaggt cattgatttt    660
gcaagcgatg caaccattac tgatccaaac ggcaaggtct actttgctga caaagatggt    720
tcggtaacct tgccgaccca acctgtccaa gaattttgc taagcggaca tgtgcgcgtt    780
agaccatata aagaaaaacc aatacaaaac caagcgaaat ctgttgatgt ggaatatact    840
gtacagttta ctcccttaaa ccctgatgac gatttcagac caggtctcaa agatactaag    900
ctattgaaaa cactagctat cggtgacacc atcacatctc aagaattact agctcaagca    960
caaagcattt taaacaaaaa ccacccaggc tatacgattt atgaacgtga ctcctcaatc   1020
gtcactcatg acaatgacat tttccgtacg attttaccaa tggatcaaga gttatcttac   1080
cgtgttaaaa atcgggaaca agcttatagg atcaataaaa aatctggtct gaatgaagaa   1140
ataaacaaca ctgacctgat ctctgagaaa tattacgtcc ttaaaaaagg ggaaaagccg   1200
tatgatccct tgatcgcag  tcacttgaaa ctgttcacca tcaaatacgt tgatgtcgat   1260
accaacgaat tgctaaaaag tgagcagctc ttaacagcta gcgaacgtaa cttagacttc   1320
agagatttat acgatcctcg tgataaggct aaactactct acaacaatct cgatgctttt   1380
ggtattatgg actataccct aactggaaaa gtagaggata tcacgatga  caccaaccgt   1440
atcataaccg tttatatggg caagcgaccc gaaggagaga atgctagcta tcatttagcc   1500
ggtggcggac aagctcaaca aattgtgccc atagctgaga agtgttttga tcatgctgct   1560
gggacttcct atttggtcgg agaaacgtgg gagaagccct accaaggctg gatgatggta   1620
gattgtactt gcctgggaga aggcagcgga cgcatcactt gcacttctag aaatagatgc   1680
aacgatcagg acacaaggac atcctataga attggagaca cctggagcaa gaaggataat   1740
```

-continued

```
cgaggaaacc tgctccagtg catctgcaca ggcaacggcc gaggagagtg gaagtgtgag   1800
aggcacacct ctgtgcagac cacatcgagc ggatctggcc ccttcaccga tgttcgttag   1860
```

<210> SEQ ID NO 3
<211> LENGTH: 619
<212> TYPE: PRT
<213> ORGANISM: Artificial Sequence
<220> FEATURE:
<223> OTHER INFORMATION: CSSK sequences modified for Pichia

<400> SEQUENCE: 3

```
Val Gln Ala Gln Gln Ile Val Pro Ile Ala Glu Lys Cys Phe Asp His
1               5                   10                  15

Ala Ala Gly Thr Ser Tyr Leu Val Gly Glu Thr Trp Glu Lys Pro Tyr
            20                  25                  30

Gln Gly Trp Met Met Val Asp Cys Thr Cys Leu Gly Glu Gly Ser Gly
        35                  40                  45

Arg Ile Thr Cys Thr Ser Arg Asn Arg Cys Asn Asp Gln Asp Thr Arg
    50                  55                  60

Thr Ser Tyr Arg Ile Gly Asp Thr Trp Ser Lys Lys Asp Asn Arg Gly
65                  70                  75                  80

Asn Leu Leu Gln Cys Ile Cys Thr Gly Asn Gly Arg Gly Glu Trp Lys
                85                  90                  95

Cys Glu Arg His Thr Ser Val Gln Thr Thr Ser Ser Gly Ser Gly Pro
            100                 105                 110

Phe Thr Asp Val Arg Ile Ala Gly Pro Glu Trp Leu Leu Asp Arg Pro
        115                 120                 125

Ser Val Asn Asn Ser Gln Leu Val Ser Val Ala Gly Thr Val Glu
    130                 135                 140

Gly Thr Asn Gln Asp Ile Ser Leu Lys Phe Phe Glu Ile Asp Leu Thr
145                 150                 155                 160

Ser Arg Pro Ala His Gly Gly Lys Thr Glu Gln Gly Leu Ser Pro Lys
                165                 170                 175

Ser Lys Pro Phe Ala Thr Asp Ser Gly Ala Met Ser His Lys Leu Glu
            180                 185                 190

Lys Ala Asp Leu Leu Lys Ala Ile Gln Glu Gln Leu Ile Ala Asn Val
        195                 200                 205

His Ser Asn Asp Asp Tyr Phe Glu Val Ile Asp Phe Ala Ser Asp Ala
    210                 215                 220

Thr Ile Thr Asp Pro Asn Gly Lys Val Tyr Phe Ala Asp Lys Asp Gly
225                 230                 235                 240

Ser Val Thr Leu Pro Thr Gln Pro Val Gln Glu Phe Leu Leu Ser Gly
                245                 250                 255

His Val Arg Val Arg Pro Tyr Lys Glu Lys Pro Ile Gln Asn Gln Ala
            260                 265                 270

Lys Ser Val Asp Val Glu Tyr Thr Val Gln Phe Thr Pro Leu Asn Pro
        275                 280                 285

Asp Asp Asp Phe Arg Pro Gly Leu Lys Asp Thr Lys Leu Leu Lys Thr
    290                 295                 300

Leu Ala Ile Gly Asp Thr Ile Thr Ser Gln Glu Leu Leu Ala Gln Ala
305                 310                 315                 320

Gln Ser Ile Leu Asn Lys Asn His Pro Gly Tyr Thr Ile Tyr Glu Arg
                325                 330                 335

Asp Ser Ser Ile Val Thr His Asp Asn Asp Ile Phe Arg Thr Ile Leu
            340                 345                 350
```

```
Pro Met Asp Gln Glu Leu Ser Tyr Arg Val Lys Asn Arg Glu Gln Ala
        355                 360                 365
Tyr Arg Ile Asn Lys Lys Ser Gly Leu Asn Glu Glu Ile Asn Asn Thr
        370                 375                 380
Asp Leu Ile Ser Glu Lys Tyr Tyr Val Leu Lys Lys Gly Glu Lys Pro
385                 390                 395                 400
Tyr Asp Pro Phe Asp Arg Ser His Leu Lys Leu Phe Thr Ile Lys Tyr
                405                 410                 415
Val Asp Val Asp Thr Asn Glu Leu Leu Lys Ser Glu Gln Leu Leu Thr
            420                 425                 430
Ala Ser Glu Arg Asn Leu Asp Phe Arg Asp Leu Tyr Asp Pro Arg Asp
        435                 440                 445
Lys Ala Lys Leu Leu Tyr Asn Asn Leu Asp Ala Phe Gly Ile Met Asp
    450                 455                 460
Tyr Thr Leu Thr Gly Lys Val Glu Asp Asn His Asp Asp Thr Asn Arg
465                 470                 475                 480
Ile Ile Thr Val Tyr Met Gly Lys Arg Pro Glu Gly Glu Asn Ala Ser
                485                 490                 495
Tyr His Leu Ala Gly Gly Gln Ala Gln Gln Ile Val Pro Ile Ala
            500                 505                 510
Glu Lys Cys Phe Asp His Ala Ala Gly Thr Ser Tyr Leu Val Gly Glu
        515                 520                 525
Thr Trp Glu Lys Pro Tyr Gln Gly Trp Met Met Val Asp Cys Thr Cys
    530                 535                 540
Leu Gly Glu Gly Ser Gly Arg Ile Thr Cys Thr Ser Arg Asn Arg Cys
545                 550                 555                 560
Asn Asp Gln Asp Thr Arg Thr Ser Tyr Arg Ile Gly Asp Thr Trp Ser
                565                 570                 575
Lys Lys Asp Asn Arg Gly Asn Leu Leu Gln Cys Ile Cys Thr Gly Asn
            580                 585                 590
Gly Arg Gly Glu Trp Lys Cys Glu Arg His Thr Ser Val Gln Thr Thr
        595                 600                 605
Ser Ser Gly Ser Gly Pro Phe Thr Asp Val Arg
    610                 615

<210> SEQ ID NO 4
<211> LENGTH: 1860
<212> TYPE: DNA
<213> ORGANISM: Artificial Sequence
<220> FEATURE:
<223> OTHER INFORMATION: CSSK sequence modified for Pichia

<400> SEQUENCE: 4
gttcaagccc agcagattgt ccaatcgct gagaagtgtt tcgatcacgc tgctggtact      60
tcatacttgg tcggtgaaac ctgggaaaag ccataccagg gatggatgat ggttgactgc    120
acctgtttag gtgaaggttc cggtagaatc acctgtacct ccagaaacag atgtaacgac    180
caggacacca gaacctctta cagaatcggt gatacctggt ccaagaagga caacagaggt    240
aacctgttgc agtgtatctg taccggtaac ggtcgtggag aatggaagtg cgagagacac    300
acttccgttc aaactacttc ttccggttcc ggtccattca ctgatgttag aatcgctggt    360
ccagaatggt tgttggacag accatccgtt aacaactccc agttggttgt ttctgttgct    420
ggtactgttg agggaactaa ccaggacatc tccttgaagt tcttcgagat cgacttgact    480
tctagaccag ctcatggtgg aaagactgag caaggcttaa gtccaaagtc caagccattc    540
```

```
gctactgatt ctggtgctat gtcccacaag ttggagaagg ctgacttgtt gaaggctatc    600
caagagcagt tgatcgctaa cgttcactct aacgacgact acttcgaggt tatcgacttc    660
gcttccgacg ctactattac tgacccaaac ggaaaggttt acttcgctga caaggacggt    720
tctgttactt tgccaactca gccagttcaa gagttcttgt tgtccggtca tgttagagtt    780
agaccataca aagagaagcc aatccagaac caggctaagt ctgttgacgt tgagtacact    840
gttcagttca ctccattgaa cccagatgac gactttagac caggattgaa ggacactaag    900
ttgttgaaaa ctttggctat cggtgacact attacttccc aagagttgtt ggctcaagct    960
cagtccatct tgaacaagaa ccacccaggt tacactatct acgagagaga ctcctccatt   1020
gttactcacg acaacgacat cttcagaact atcttgccaa tggaccaaga gttgtcctac   1080
agagttaaga acagagagca ggcttacaga atcaacaaga agtccggatt gaacgaagag   1140
atcaacaaca ctgacttgat ctccgagaag tactacgttt tgaagaaggg tgaaaagcca   1200
tacgatccat cgacagatc ccacttgaag ttgttcacta tcaagtacgt tgacgttgac   1260
actaacgagt tgttgaagtc cgagcagttg ttgactgctt ccgagagaaa cttggacttc   1320
agagacttgt acgacccaag agacaaggct aaattgttgt acaataactt ggacgctttc   1380
ggtatcatgg actacacttt gactggaaag gttgaggata accacgacga cactaacaga   1440
atcatcactg tttacatggg taaaagacca gagggtgaaa acgcttctta ccacttggct   1500
ggaggtggtc aagctcaaca atcgtccct atcgccgaaa agtgttttga ccatgccgct   1560
ggtactagtt acctggtggg tgaaacttgg gagaaacctt atcaaggatg gatgatggtc   1620
gattgtactt gtttgggaga gggatccggt agaattactt gcaccagtag aaacagatgc   1680
aatgatcaag atactagaac ttcctacaga attggtgaca cttggagtaa gaaggataat   1740
agaggtaatc ttctgcaatg catctgcact ggaaacggaa ggggtgagtg gaaatgcgaa   1800 agacataccct ctgttcagac tacctcttct ggttctggac ccttcaccga tgtcagatag   1860
```

<210> SEQ ID NO 5
<211> LENGTH: 619
<212> TYPE: PRT
<213> ORGANISM: Artificial Sequence
<220> FEATURE:
<223> OTHER INFORMATION: CSSK modified N-terminal original C-terminal

<400> SEQUENCE: 5

```
Val Gln Ala Gln Gln Ile Val Pro Ile Ala Glu Lys Cys Phe Asp His
1               5                   10                  15

Ala Ala Gly Thr Ser Tyr Leu Val Gly Glu Thr Trp Glu Lys Pro Tyr
            20                  25                  30

Gln Gly Trp Met Met Val Asp Cys Thr Cys Leu Gly Glu Gly Ser Gly
        35                  40                  45

Arg Ile Thr Cys Thr Ser Arg Asn Arg Cys Asn Asp Gln Asp Thr Arg
    50                  55                  60

Thr Ser Tyr Arg Ile Gly Asp Thr Trp Ser Lys Lys Asp Asn Arg Gly
65                  70                  75                  80

Asn Leu Leu Gln Cys Ile Cys Thr Gly Asn Gly Arg Gly Glu Trp Lys
                85                  90                  95

Cys Glu Arg His Thr Ser Val Gln Thr Thr Ser Ser Gly Ser Gly Pro
            100                 105                 110

Phe Thr Asp Val Arg Ile Ala Gly Pro Glu Trp Leu Leu Asp Arg Pro
        115                 120                 125
```

```
Ser Val Asn Asn Ser Gln Leu Val Ser Val Ala Gly Thr Val Glu
130                 135                 140

Gly Thr Asn Gln Asp Ile Ser Leu Lys Phe Phe Glu Ile Asp Leu Thr
145                 150                 155                 160

Ser Arg Pro Ala His Gly Gly Lys Thr Glu Gln Gly Leu Ser Pro Lys
                165                 170                 175

Ser Lys Pro Phe Ala Thr Asp Ser Gly Ala Met Ser His Lys Leu Glu
            180                 185                 190

Lys Ala Asp Leu Leu Lys Ala Ile Gln Glu Gln Leu Ile Ala Asn Val
        195                 200                 205

His Ser Asn Asp Asp Tyr Phe Glu Val Ile Asp Phe Ala Ser Asp Ala
210                 215                 220

Thr Ile Thr Asp Pro Asn Gly Lys Val Tyr Phe Ala Asp Lys Asp Gly
225                 230                 235                 240

Ser Val Thr Leu Pro Thr Gln Pro Val Gln Glu Phe Leu Leu Ser Gly
                245                 250                 255

His Val Arg Val Arg Pro Tyr Lys Glu Lys Pro Ile Gln Asn Gln Ala
            260                 265                 270

Lys Ser Val Asp Val Glu Tyr Thr Val Gln Phe Thr Pro Leu Asn Pro
        275                 280                 285

Asp Asp Asp Phe Arg Pro Gly Leu Lys Asp Thr Lys Leu Leu Lys Thr
290                 295                 300

Leu Ala Ile Gly Asp Thr Ile Thr Ser Gln Glu Leu Leu Ala Gln Ala
305                 310                 315                 320

Gln Ser Ile Leu Asn Lys Asn His Pro Gly Tyr Thr Ile Tyr Glu Arg
                325                 330                 335

Asp Ser Ser Ile Val Thr His Asp Asn Asp Ile Phe Arg Thr Ile Leu
            340                 345                 350

Pro Met Asp Gln Glu Leu Ser Tyr Arg Val Lys Asn Arg Glu Gln Ala
        355                 360                 365

Tyr Arg Ile Asn Lys Lys Ser Gly Leu Asn Glu Ile Asn Asn Thr
370                 375                 380

Asp Leu Ile Ser Glu Lys Tyr Tyr Val Leu Lys Lys Gly Glu Lys Pro
385                 390                 395                 400

Tyr Asp Pro Phe Asp Arg Ser His Leu Lys Leu Phe Thr Ile Lys Tyr
                405                 410                 415

Val Asp Val Asp Thr Asn Glu Leu Leu Lys Ser Glu Gln Leu Leu Thr
            420                 425                 430

Ala Ser Glu Arg Asn Leu Asp Phe Arg Asp Leu Tyr Asp Pro Arg Asp
        435                 440                 445

Lys Ala Lys Leu Leu Tyr Asn Asn Leu Asp Ala Phe Gly Ile Met Asp
450                 455                 460

Tyr Thr Leu Thr Gly Lys Val Glu Asp Asn His Asp Asp Thr Asn Arg
465                 470                 475                 480

Ile Ile Thr Val Tyr Met Gly Lys Arg Pro Glu Gly Glu Asn Ala Ser
                485                 490                 495

Tyr His Leu Ala Gly Gly Gln Ala Gln Gln Ile Val Pro Ile Ala
            500                 505                 510

Glu Lys Cys Phe Asp His Ala Ala Gly Thr Ser Tyr Leu Val Gly Glu
        515                 520                 525

Thr Trp Glu Lys Pro Tyr Gln Gly Trp Met Met Val Asp Cys Thr Cys
530                 535                 540

Leu Gly Glu Gly Ser Gly Arg Ile Thr Cys Thr Ser Arg Asn Arg Cys
```

```
                          545                 550                 555                 560
Asn Asp Gln Asp Thr Arg Thr Ser Tyr Arg Ile Gly Asp Thr Trp Ser
                565                 570                 575

Lys Lys Asp Asn Arg Gly Asn Leu Leu Gln Cys Ile Cys Thr Gly Asn
                580                 585                 590

Gly Arg Gly Glu Trp Lys Cys Glu Arg His Thr Ser Val Gln Thr Thr
            595                 600                 605

Ser Ser Gly Ser Gly Pro Phe Thr Asp Val Arg
        610                 615

<210> SEQ ID NO 6
<211> LENGTH: 1860
<212> TYPE: DNA
<213> ORGANISM: Artificial Sequence
<220> FEATURE:
<223> OTHER INFORMATION: CSSK modified 5' original 3'

<400> SEQUENCE: 6
gttcaagccc agcagattgt ccaatcgct gagaagtgtt tcgatcacgc tgctggtact      60
tcatacttgg tcggtgaaac ctgggaaaag ccataccagg gatggatgat ggttgactgc    120
acctgtttag gtgaaggttc cggtagaatc acctgtacct ccagaaacag atgtaacgac    180
caggacacca gaacctctta cagaatcggt gatacctggt ccaagaagga caacagaggt    240
aacctgttgc agtgtatctg taccggtaac ggtcgtggag aatggaagtg cgagagacac    300
acttccgttc aaactacttc ttccggttcc ggtccattca ctgatgttag aatcgctggt    360
ccagaatggt tgttggacag accatccgtt aacaactccc agttggttgt ttctgttgct    420
ggtactgttg agggaactaa ccaggacatc tccttgaagt tcttcgagat cgacttgact    480
tctagaccag ctcatggtgg aaagactgag caaggcttaa gtccaaaatc aaaaccattt    540
gctactgata gtggcgcgat gtcacataaa cttgagaaag ctgacttact aaaggctatt    600
caagaacaat tgatcgctaa cgtccacagt aacgacgact actttgaggt cattgatttt    660
gcaagcgatg caaccattac tgatccaaac ggcaaggtct actttgctga caaagatggt    720
tcggtaacct tgccgaccca acctgtccaa gaattttgc taagcggaca tgtgcgcgtt    780
agaccatata agaaaaaacc aatacaaaac caagcgaaat ctgttgatgt ggaatatact    840
gtacagttta ctcccttaaa ccctgatgac gatttcagac caggtctcaa agatactaag    900
ctattgaaaa cactagctat cggtgacacc atcacatctc aagaattact agctcaagca    960
caaagcattt taaacaaaaa ccacccaggc tatacgattt atgaacgtga ctcctcaatc   1020
gtcactcatg acaatgacat tttccgtacg attttaccaa tggatcaaga gttatcttac   1080
cgtgttaaaa atcgggaaca agcttatagg atcaataaaa aatctggtct gaatgaagaa   1140
ataaacaaca ctgacctgat ctctgagaaa tattacgtcc ttaaaaaagg ggaaaagccg   1200
tatgatccct tgatcgcag tcacttgaaa ctgttcacca tcaaatacgt tgatgtcgat   1260
accaacgaat tgctaaaaag tgagcagctc ttaacagcta gcgaacgtaa cttagacttc   1320
agagatttat acgatcctcg tgataaggct aaactactct acaacaatct cgatgctttt   1380
ggtattatgg actataccctt aactggaaaa gtagaggata tcacgatga caccaaccgt   1440 atcataaccg tttatatggg caagcgaccc gaaggagaga atgctagcta tcatttagcc   1500
ggtggcggac aagctcaaca aattgtgccc atagctgaga agtgttttga tcatgctgct   1560
gggacttcct atttggtcgg agaaacgtgg gagaagccct accaaggctg gatgatggta   1620
gattgtactt gcctgggaga aggcagcgga cgcatcactt gcacttctag aaatagatgc   1680
```

-continued

```
aacgatcagg acacaaggac atcctataga attggagaca cctggagcaa gaaggataat    1740
cgaggaaacc tgctccagtg catctgcaca ggcaacggcc gaggagagtg gaagtgtgag    1800
aggcacacct ctgtgcagac cacatcgagc ggatctggcc ccttcaccga tgttcgttag    1860
```

<210> SEQ ID NO 7
<211> LENGTH: 619
<212> TYPE: PRT
<213> ORGANISM: Artificial Sequence
<220> FEATURE:
<223> OTHER INFORMATION: CSSK original N-terminal modified C-terminal

<400> SEQUENCE: 7

```
Val Gln Ala Gln Gln Ile Val Pro Ile Ala Glu Lys Cys Phe Asp His
1               5                   10                  15

Ala Ala Gly Thr Ser Tyr Leu Val Gly Glu Thr Trp Glu Lys Pro Tyr
            20                  25                  30

Gln Gly Trp Met Met Val Asp Cys Thr Cys Leu Gly Glu Gly Ser Gly
        35                  40                  45

Arg Ile Thr Cys Thr Ser Arg Asn Arg Cys Asn Asp Gln Asp Thr Arg
    50                  55                  60

Thr Ser Tyr Arg Ile Gly Asp Thr Trp Ser Lys Lys Asp Asn Arg Gly
65                  70                  75                  80

Asn Leu Leu Gln Cys Ile Cys Thr Gly Asn Gly Arg Gly Glu Trp Lys
                85                  90                  95

Cys Glu Arg His Thr Ser Val Gln Thr Thr Ser Ser Gly Ser Gly Pro
            100                 105                 110

Phe Thr Asp Val Arg Ile Ala Gly Pro Glu Trp Leu Leu Asp Arg Pro
        115                 120                 125

Ser Val Asn Asn Ser Gln Leu Val Val Ser Val Ala Gly Thr Val Glu
    130                 135                 140

Gly Thr Asn Gln Asp Ile Ser Leu Lys Phe Phe Glu Ile Asp Leu Thr
145                 150                 155                 160

Ser Arg Pro Ala His Gly Gly Lys Thr Glu Gln Gly Leu Ser Pro Lys
                165                 170                 175

Ser Lys Pro Phe Ala Thr Asp Ser Gly Ala Met Ser His Lys Leu Glu
            180                 185                 190

Lys Ala Asp Leu Leu Lys Ala Ile Gln Glu Gln Leu Ile Ala Asn Val
        195                 200                 205

His Ser Asn Asp Asp Tyr Phe Glu Val Ile Asp Phe Ala Ser Asp Ala
    210                 215                 220

Thr Ile Thr Asp Pro Asn Gly Lys Val Tyr Phe Ala Asp Lys Asp Gly
225                 230                 235                 240

Ser Val Thr Leu Pro Thr Gln Pro Val Gln Glu Phe Leu Leu Ser Gly
                245                 250                 255

His Val Arg Val Arg Pro Tyr Lys Glu Lys Pro Ile Gln Asn Gln Ala
            260                 265                 270

Lys Ser Val Asp Val Glu Tyr Thr Val Gln Phe Thr Pro Leu Asn Pro
        275                 280                 285

Asp Asp Asp Phe Arg Pro Gly Leu Lys Asp Thr Lys Leu Leu Lys Thr
    290                 295                 300

Leu Ala Ile Gly Asp Thr Ile Thr Ser Gln Glu Leu Leu Ala Gln Ala
305                 310                 315                 320

Gln Ser Ile Leu Asn Lys Asn His Pro Gly Tyr Thr Ile Tyr Glu Arg
                325                 330                 335
```

Asp Ser Ser Ile Val Thr His Asp Asn Asp Ile Phe Arg Thr Ile Leu
            340                 345                 350

Pro Met Asp Gln Glu Leu Ser Tyr Arg Val Lys Asn Arg Glu Gln Ala
            355                 360                 365

Tyr Arg Ile Asn Lys Lys Ser Gly Leu Asn Glu Glu Ile Asn Asn Thr
        370                 375                 380

Asp Leu Ile Ser Glu Lys Tyr Tyr Val Leu Lys Lys Gly Glu Lys Pro
385                 390                 395                 400

Tyr Asp Pro Phe Asp Arg Ser His Leu Lys Leu Phe Thr Ile Lys Tyr
                405                 410                 415

Val Asp Val Asp Thr Asn Glu Leu Leu Lys Ser Glu Gln Leu Leu Thr
            420                 425                 430

Ala Ser Glu Arg Asn Leu Asp Phe Arg Asp Leu Tyr Asp Pro Arg Asp
        435                 440                 445

Lys Ala Lys Leu Leu Tyr Asn Asn Leu Asp Ala Phe Gly Ile Met Asp
    450                 455                 460

Tyr Thr Leu Thr Gly Lys Val Glu Asp Asn His Asp Asp Thr Asn Arg
465                 470                 475                 480

Ile Ile Thr Val Tyr Met Gly Lys Arg Pro Glu Gly Glu Asn Ala Ser
                485                 490                 495

Tyr His Leu Ala Gly Gly Gln Ala Gln Gln Ile Val Pro Ile Ala
            500                 505                 510

Glu Lys Cys Phe Asp His Ala Ala Gly Thr Ser Tyr Leu Val Gly Glu
        515                 520                 525

Thr Trp Glu Lys Pro Tyr Gln Gly Trp Met Met Val Asp Cys Thr Cys
530                 535                 540

Leu Gly Glu Gly Ser Gly Arg Ile Thr Cys Thr Ser Arg Asn Arg Cys
545                 550                 555                 560

Asn Asp Gln Asp Thr Arg Thr Ser Tyr Arg Ile Gly Asp Thr Trp Ser
                565                 570                 575

Lys Lys Asp Asn Arg Gly Asn Leu Leu Gln Cys Ile Cys Thr Gly Asn
            580                 585                 590

Gly Arg Gly Glu Trp Lys Cys Glu Arg His Thr Ser Val Gln Thr Thr
        595                 600                 605

Ser Ser Gly Ser Gly Pro Phe Thr Asp Val Arg
    610                 615

<210> SEQ ID NO 8
<211> LENGTH: 1860
<212> TYPE: DNA
<213> ORGANISM: Artificial Sequence
<220> FEATURE:
<223> OTHER INFORMATION: CSSK original 5' modified 3'

<400> SEQUENCE: 8
gtgcaagctc aacaaattgt gcccatagct gagaagtgtt ttgatcatgc tgctgggact      60
tcctatttgg tcggagaaac gtgggagaag ccctaccaag gctggatgat ggtagattgt     120
acttgcctgg agaaggcag cggacgcatc acttgcactt ctagaaatag atgcaacgat      180
caggacacaa ggacatccta tagaattgga gacacctgga gcaagaagga taatcgagga     240
aacctgctcc agtgcatctg cacaggcaac ggccgaggag agtggaagtg tgagaggcac     300
acctctgtgc agaccacatc gagcggatct ggccccttca ccgatgttcg tattgctgga     360
cctgagtggc tgctagaccg tccatctgtc aacaacagcc aattagttgt tagcgttgct     420

```
ggtactgttg agggggacgaa tcaagacatt agtcttaaat tttttgaaat cgatctaaca    480
tcacgacctg ctcatggagg aaagacagag caaggcttaa gtccaaagtc caagccattc    540
gctactgatt ctggtgctat gtcccacaag ttggagaagg ctgacttgtt gaaggctatc    600
caagagcagt tgatcgctaa cgttcactct aacgacgact acttcgaggt tatcgacttc    660
gcttccgacg ctactattac tgacccaaac ggaaaggttt acttcgctga caaggacggt    720
tctgttactt tgccaactca gccagttcaa gagttcttgt tgtccggtca tgttagagtt    780
agaccataca aagagaagcc aatccagaac caggctaagt ctgttgacgt tgagtacact    840
gttcagttca ctccattgaa cccagatgac gactttagac caggattgaa ggacactaag    900
ttgttgaaaa ctttggctat cggtgacact attacttccc aagagttgtt ggctcaagct    960
cagtccatct tgaacaagaa ccacccaggt tacactatct acgagagaga ctcctccatt   1020
gttactcacg acaacgacat cttcagaact atcttgccaa tggaccaaga gttgtcctac   1080
agagttaaga acagagagca ggcttacaga atcaacaaga gtccggatt gaacgaagag    1140 atcaacaaca ctgacttgat ctccgagaag tactacgttt tgaagaaggg tgaaaagcca   1200
tacgatccat cgacagatc ccacttgaag ttgttcacta tcaagtacgt tgacgttgac   1260
actaacgagt tgttgaagtc cgagcagttg ttgactgctt ccgagagaaa cttggacttc   1320
agagacttgt acgacccaag agacaaggct aaattgttgt acaataactt ggacgctttc   1380
ggtatcatgg actacttt gactggaaag gttgaggata ccacgacga cactaacaga     1440 atcatcactg tttacatggg taaaagacca gagggtgaaa acgcttctta ccacttggct   1500
ggaggtggtc aagctcaaca aatcgtccct atcgccgaaa agtgttttga ccatgccgct   1560
ggtactagtt acctggtggg tgaaacttgg gagaaacctt atcaaggatg gatgatggtc   1620
gattgtactt gtttgggaga gggatccggt agaattactt gcaccagtag aaacagatgc   1680
aatgatcaag atactagaac ttcctacaga attggtgaca cttggagtaa aaggataat    1740 agaggtaatc ttctgcaatg catctgcact ggaaacggaa ggggtgagtg gaaatgcgaa   1800
agacatacct ctgttcagac tacctcttct ggttctggac ccttcaccga tgtcagatag   1860
```

<210> SEQ ID NO 9
<211> LENGTH: 85
<212> TYPE: PRT
<213> ORGANISM: Artificial Sequence
<220> FEATURE:
<223> OTHER INFORMATION: Modified Alpha Signal Sequence

<400> SEQUENCE: 9

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
            85
```

<210> SEQ ID NO 10
<211> LENGTH: 255

```
<212> TYPE: DNA
<213> ORGANISM: Artificial Sequence
<220> FEATURE:
<223> OTHER INFORMATION: Modified alpha signal sequence

<400> SEQUENCE: 10
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacggggtat tgtttataaa tactactatt gccagcattg ctgctaaaga agaaggggta     240
tctctcgaga aaaga                                                      255

<210> SEQ ID NO 11
<211> LENGTH: 414
<212> TYPE: PRT
<213> ORGANISM: Artificial Sequence
<220> FEATURE:
<223> OTHER INFORMATION: Streptokinase sequence

<400> SEQUENCE: 11
```

Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
        35                  40                  45

Gly Gly Lys Thr Glu Gln Gly Leu Ser Pro Lys Ser Lys Pro Phe Ala
    50                  55                  60

Thr Asp Ser Gly Ala Met Ser His Lys Leu Glu Lys Ala Asp Leu Leu
65                  70                  75                  80

Lys Ala Ile Gln Glu Gln Leu Ile Ala Asn Val His Ser Asn Asp Asp
                85                  90                  95

Tyr Phe Glu Val Ile Asp Phe Ala Ser Asp Ala Thr Ile Thr Asp Arg
            100                 105                 110

Asn Gly Lys Val Tyr Phe Ala Asp Lys Asp Gly Ser Val Thr Leu Pro
        115                 120                 125

Thr Gln Pro Val Gln Glu Phe Leu Leu Ser Gly His Val Arg Val Arg
    130                 135                 140

Pro Tyr Lys Glu Lys Pro Ile Gln Asn Gln Ala Lys Ser Val Asp Val
145                 150                 155                 160

Glu Tyr Thr Val Gln Phe Thr Pro Leu Asn Pro Asp Asp Asp Phe Arg
                165                 170                 175

Pro Gly Leu Lys Asp Thr Lys Leu Leu Lys Thr Leu Ala Ile Gly Asp
            180                 185                 190

Thr Ile Thr Ser Gln Glu Leu Leu Ala Gln Ala Gln Ser Ile Leu Asn
        195                 200                 205

Lys Asn His Pro Gly Tyr Thr Ile Tyr Glu Arg Asp Ser Ser Ile Val
    210                 215                 220

Thr His Asp Asn Asp Ile Phe Arg Thr Ile Leu Pro Met Asp Gln Glu
225                 230                 235                 240

Phe Thr Tyr Arg Val Lys Asn Arg Glu Gln Ala Tyr Arg Ile Asn Lys
                245                 250                 255

Lys Ser Gly Leu Asn Glu Glu Ile Asn Asn Thr Asp Leu Ile Ser Glu
            260                 265                 270

Lys Tyr Tyr Val Leu Lys Lys Gly Glu Lys Pro Tyr Asp Pro Phe Asp

```
                275                 280                 285
Arg Ser His Leu Lys Leu Phe Thr Ile Lys Tyr Val Asp Val Asp Thr
    290                 295                 300

Asn Glu Leu Leu Lys Ser Glu Gln Leu Leu Thr Ala Ser Glu Arg Asn
305                 310                 315                 320

Leu Asp Phe Arg Asp Leu Tyr Asp Pro Arg Asp Lys Ala Lys Leu Leu
                325                 330                 335

Tyr Asn Asn Leu Asp Ala Phe Gly Ile Met Asp Tyr Thr Leu Thr Gly
                340                 345                 350

Lys Val Glu Asp Asn His Asp Asp Thr Asn Arg Ile Ile Thr Val Tyr
                355                 360                 365

Met Gly Lys Arg Pro Glu Gly Glu Asn Ala Ser Tyr His Leu Ala Tyr
    370                 375                 380

Asp Lys Asp Arg Tyr Thr Glu Glu Glu Arg Glu Val Tyr Ser Tyr Leu
385                 390                 395                 400

Arg Tyr Thr Gly Thr Pro Ile Pro Asp Asn Pro Asn Asp Lys
                405                 410

<210> SEQ ID NO 12
<211> LENGTH: 15
<212> TYPE: PRT
<213> ORGANISM: Artificial Sequence
<220> FEATURE:
<223> OTHER INFORMATION: SK C-terminal equence with poly-glycine linder
      and transglutaminase site

<400> SEQUENCE: 12

Asn Ala Ser Tyr His Leu Ala Gly Gly Gly Gln Ala Gln Gln Ile
1               5                   10                  15

<210> SEQ ID NO 13
<211> LENGTH: 53
<212> TYPE: DNA
<213> ORGANISM: Artificial Sequence
<220> FEATURE:
<223> OTHER INFORMATION: SK 3' sequence with poly-glycine liner and
      transglutaminase site

<400> SEQUENCE: 13
gaatgctagc taccatttag ctggtggtgg ccagtgcgca acagattgta ccc         53

<210> SEQ ID NO 14
<211> LENGTH: 99
<212> TYPE: PRT
<213> ORGANISM: Artificial Sequence
<220> FEATURE:
<223> OTHER INFORMATION: Native alpha signal sequence

<400> SEQUENCE: 14

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Tyr Val Glu Phe Pro Arg Ala
```

<210> SEQ ID NO 15
<211> LENGTH: 300
<212> TYPE: DNA
<213> ORGANISM: Artificial Sequence
<220> FEATURE:
<223> OTHER INFORMATION: Native alpha signal sequence

<400> SEQUENCE: 15

```
atgagatttc cttcaatttt tactgcagtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc catttccaa cagcacaaat    180
aacggggttat tgtttataaa tactactatt gccagcattg ctgctaaaga agaaggggta   240
tctctcgaga aaagagaggc tgaagcttac gtagaattcc ctagggcggc cgcgaattaa   300
```

<210> SEQ ID NO 16
<211> LENGTH: 7
<212> TYPE: PRT
<213> ORGANISM: Artificial Sequence
<220> FEATURE:
<223> OTHER INFORMATION: Signal peptide sequence stretch

<400> SEQUENCE: 16

Glu Lys Arg Glu Ala Glu Ala
1               5

<210> SEQ ID NO 17
<211> LENGTH: 594
<212> TYPE: DNA
<213> ORGANISM: Artificial Sequence
<220> FEATURE:
<223> OTHER INFORMATION: Partial vector sequence with AOX1 5' promoter
      and alpha sequence

<400> SEQUENCE: 17

```
ttatcatcat tattagctta cttcataatt gcgactggtt ccaattgaca agctttgatt    60
ttaacgactt ttaacgacaa cttgagaaga tcaaaaacaa ctaattattc gaaggatcca   120
aacgatgaga tttccttcaa tttttactgc aatttttattc gcagcatcct ccgcattagc   180
tgctccagtc aacactacaa cagaagatga aacggcacaa attccggctg aagctgtcat   240
cggttactca satttagaag gggatttcga tgttgctgtt ttgccatttt ccaacagcac   300
aaataacggg ttattgttta aaatactac tattgccagc attgctgcta agaagaagg    360
ggtatctctc gagaaaagag aggctgaagc ttacgtagaa ttccctaggg cggccgcgat   420
ttaattcgcc ttagacatga ctgttcctca gttcaagttg gcacttacg agaagaccgg    480
tcttgctaga ttctaatcaa gaggatgtca gaatgccatt tcggtgagag atgcaggctt   540
cattttttgat actttttta ttgtaaccta tatagtatag gatttttttt gtga         594
```

<210> SEQ ID NO 18
<211> LENGTH: 50
<212> TYPE: DNA
<213> ORGANISM: Artificial Sequence
<220> FEATURE:
<223> OTHER INFORMATION: Partical vector sequence

<400> SEQUENCE: 18

```
ctcgagaaaa gagaggctga agcttacgta gaattcccta gggcggcctc              50
```

<210> SEQ ID NO 19
<211> LENGTH: 13
<212> TYPE: PRT
<213> ORGANISM: Artificial Sequence
<220> FEATURE:
<223> OTHER INFORMATION: Polypeptide encoded by partial vector sequence

<400> SEQUENCE: 19

Glu Lys Arg Glu Ala Glu Ala Tyr Val Glu Phe Pro Arg
1               5                   10

<210> SEQ ID NO 20
<211> LENGTH: 97
<212> TYPE: PRT
<213> ORGANISM: Artificial Sequence
<220> FEATURE:
<223> OTHER INFORMATION: Alpha signal sequence plus N-terminal CSSK

<400> SEQUENCE: 20

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Gln Ala Gln Gln Ile Val Pro Ile Ala Glu Lys
                85                  90                  95

Cys

<210> SEQ ID NO 21
<211> LENGTH: 330
<212> TYPE: DNA
<213> ORGANISM: Artificial Sequence
<220> FEATURE:
<223> OTHER INFORMATION: Fibrin binding domains 4,5

<400> SEQUENCE: 21
cccatagctg agaagtgttt tgatcatgct gctgggactt cctatgtggt cggagaaacg      60
tgggagaagc cctaccaagg ctggatgatg gtagattgta cttgcctggg agaaggcagc     120
ggacgcatca cttgcacttc tagaaataga tgcaacgatc aggacacaag gacatcctat    180
agaattggag acacctggag caagaaggat aatcgaggaa acctgctcca gtgcatctgc    240
acaggcaacg gccgaggaga gtggaagtgt gagaggcaca cctctgtgca gaccacatcg    300
agcggatctg gccccttcac cgatgttcgt                                     330

<210> SEQ ID NO 22
<211> LENGTH: 110
<212> TYPE: PRT
<213> ORGANISM: Artificial Sequence
<220> FEATURE:
<223> OTHER INFORMATION: Fibrin binding domains 4,5

<400> SEQUENCE: 22

Pro Ile Ala Glu Lys Cys Phe Asp His Ala Ala Gly Thr Ser Tyr Val
1               5                   10                  15

-continued

| | | | | | | | | | | | |
|---|---|---|---|---|---|---|---|---|---|---|---|
|Val|Gly|Glu|Thr|Trp|Glu|Lys|Pro|Tyr|Gln|Gly|Trp|Met|Met|Val|Asp|
| | | |20| | | |25| | | |30| | | | |

Cys Thr Cys Leu Gly Glu Gly Ser Gly Arg Ile Thr Cys Thr Ser Arg
          35                  40                  45

Asn Arg Cys Asn Asp Gln Asp Ser Arg Thr Ser Tyr Arg Ile Gly Asp
     50                  55                  60

Thr Trp Ser Lys Lys Asp Asn Arg Gly Asn Leu Leu Gln Cys Ile Cys
65                  70                  75                  80

Thr Gly Asn Gly Arg Gly Glu Trp Lys Cys Glu Arg His Thr Ser Val
               85                  90                  95

Gln Thr Thr Ser Ser Gly Ser Gly Pro Phe Thr Asp Val Arg
               100                 105                 110

<210> SEQ ID NO 23
<211> LENGTH: 2115
<212> TYPE: DNA
<213> ORGANISM: Artificial Sequence
<220> FEATURE:
<223> OTHER INFORMATION: CSSK sequence modified alpha sequence plus
      modified for Picha

<400> SEQUENCE: 23

```
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc catttccaa cagcacaaat      180
aacgggttat tgtttataaa tactactatt gccagcattg ctgctaaaga agaaggggta     240
tctctcgaga aaagagttca agcccagcag attgttccaa tcgctgagaa gtgtttcgat     300
cacgctgctg gtacttcata cttggtcggt gaaacctggg aaaagccata ccagggatgg     360
atgatggttg actgcacctg tttaggtgaa ggttccggta gaatcacctg tacctccaga     420
aacagatgta acgaccagga caccagaacc tcttacagaa tcggtgatac ctggtccaag     480
aaggacaaca gaggtaacct gttgcagtgt atctgtaccg gtaacggtcg tggagaatgg     540
aagtgcgaga gacacacttc cgttcaaact acttcttccg gttccggtcc attcactgat     600
gttagaatcg ctggtccaga tggttgttg acagaccat ccgttaacaa ctcccagttg       660
gttgtttctg ttgctggtac tgttgaggga actaaccagg acatctcctt gaagttcttc     720
gagatcgact tgacttctag accagctcat ggtggaaaga ctgagcaagg cttaagtcca     780
aagtccaagc cattcgctac tgattctggt gctatgtccc acaagttgga aaggctgac     840
ttgttgaagg ctatccaaga gcagttgatc gctaacgttc actctaacga cgactacttc     900
gaggttatcg acttcgcttc cgacgctact attactgacc caaacggaaa ggtttacttc     960
gctgacaagg acggttctgt tactttgcca actcagccag ttcaagagtt cttgttgtcc    1020
ggtcatgtta gagttagacc atacaaagag aagccaatcc agaaccaggc taagtctgtt   1080
gacgttgagt acactgttca gttcactcca ttgaacccag atgacgactt tagaccagga    1140
ttgaaggaca ctaagttgtt gaaaactttg gctatcggtg acactattac ttcccaagag    1200
ttgttggctc aagctcagtc catcttgaac aagaaccacc caggttacac tatctacgag    1260
agagactcct ccattgttac tcacgacaac gacatcttca gaactatctt gccaatggac    1320
caagagttgt cctacagagt taagaacaga gagcaggctt acagaatcaa caagaagtcc    1380
ggattgaacg aagagatcaa caacactgac ttgatctccg agaagtacta cgttttgaag   1440
aagggtgaaa agccatacga tccattcgac agatcccact tgaagttgtt cactatcaag    1500
```

```
tacgttgacg ttgacactaa cgagttgttg aagtccgagc agttgttgac tgcttccgag    1560
agaaacttgg acttcagaga cttgtacgac ccaagagaca aggctaaatt gttgtacaat    1620
aacttggacg ctttcggtat catggactac actttgactg aaaggttgga ggataaccac    1680
gacgacacta acagaatcat cactgtttac atgggtaaaa accagagggg tgaaaacgct    1740
tcttaccact tggctggagg tggtcaagct caacaaatcg tccctatcgc cgaaaagtgt    1800
tttgaccatg ccgctggtac tagttacctg gtgggtgaaa cttgggagaa accttatcaa    1860
ggatggatga tggtcgattg tacttgtttg ggagagggat ccggtagaat tacttgcacc    1920
agtagaaaca gatgcaatga tcaagatact agaacttcct acagaattgg tgacacttgg    1980
agtaagaagg ataatagagg taatcttctg caatgcatct gcactggaaa cggaagggt     2040 gagtggaaat gcgaaagaca tacctctgtt cagactacct cttctggttc tggacccttc    2100
accgatgtca gatag                                                     2115
```

<210> SEQ ID NO 24
<211> LENGTH: 704
<212> TYPE: PRT
<213> ORGANISM: Artificial Sequence
<220> FEATURE:
<223> OTHER INFORMATION: CSSK sequence modified alpha sequence plus
      modified for Pichia

<400> SEQUENCE: 24

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Val Gln Ala Gln Gln Ile Val Pro Ile Ala Glu
                85                  90                  95

Lys Cys Phe Asp His Ala Ala Gly Thr Ser Tyr Leu Val Gly Glu Thr
            100                 105                 110

Trp Glu Lys Pro Tyr Gln Gly Trp Met Met Val Asp Cys Thr Cys Leu
        115                 120                 125

Gly Glu Gly Ser Gly Arg Ile Thr Cys Thr Ser Arg Asn Arg Cys Asn
    130                 135                 140

Asp Gln Asp Thr Arg Thr Ser Tyr Arg Ile Gly Asp Thr Trp Ser Lys
145                 150                 155                 160

Lys Asp Asn Arg Gly Asn Leu Leu Gln Cys Ile Cys Thr Gly Asn Gly
                165                 170                 175

Arg Gly Glu Trp Lys Cys Glu Arg His Thr Ser Val Gln Thr Thr Ser
            180                 185                 190

Ser Gly Ser Gly Pro Phe Thr Asp Val Arg Ile Ala Gly Pro Glu Trp
        195                 200                 205

Leu Leu Asp Arg Pro Ser Val Asn Asn Ser Gln Leu Val Val Ser Val
    210                 215                 220

Ala Gly Thr Val Glu Gly Thr Asn Gln Asp Ile Ser Leu Lys Phe Phe
225                 230                 235                 240

Glu Ile Asp Leu Thr Ser Arg Pro Ala His Gly Gly Lys Thr Glu Gln
```

```
            245                 250                 255
Gly Leu Ser Pro Lys Ser Lys Pro Phe Ala Thr Asp Ser Gly Ala Met
        260                 265                 270

Ser His Lys Leu Glu Lys Ala Asp Leu Leu Lys Ala Ile Gln Glu Gln
            275                 280                 285

Leu Ile Ala Asn Val His Ser Asn Asp Asp Tyr Phe Glu Val Ile Asp
        290                 295                 300

Phe Ala Ser Asp Ala Thr Ile Thr Asp Pro Asn Gly Lys Val Tyr Phe
305                 310                 315                 320

Ala Asp Lys Asp Gly Ser Val Thr Leu Pro Thr Gln Pro Val Gln Glu
                325                 330                 335

Phe Leu Leu Ser Gly His Val Arg Val Arg Pro Tyr Lys Glu Lys Pro
            340                 345                 350

Ile Gln Asn Gln Ala Lys Ser Val Asp Val Glu Tyr Thr Val Gln Phe
        355                 360                 365

Thr Pro Leu Asn Pro Asp Asp Phe Arg Pro Gly Leu Lys Asp Thr
    370                 375                 380

Lys Leu Leu Lys Thr Leu Ala Ile Gly Asp Thr Ile Thr Ser Gln Glu
385                 390                 395                 400

Leu Leu Ala Gln Ala Gln Ser Ile Leu Asn Lys Asn His Pro Gly Tyr
                405                 410                 415

Thr Ile Tyr Glu Arg Asp Ser Ser Ile Val Thr His Asp Asn Asp Ile
            420                 425                 430

Phe Arg Thr Ile Leu Pro Met Asp Gln Glu Leu Ser Tyr Arg Val Lys
        435                 440                 445

Asn Arg Glu Gln Ala Tyr Arg Ile Asn Lys Lys Ser Gly Leu Asn Glu
    450                 455                 460

Glu Ile Asn Asn Thr Asp Leu Ile Ser Glu Lys Tyr Tyr Val Leu Lys
465                 470                 475                 480

Lys Gly Glu Lys Pro Tyr Asp Pro Phe Asp Arg Ser His Leu Lys Leu
                485                 490                 495

Phe Thr Ile Lys Tyr Val Asp Val Asp Thr Asn Glu Leu Leu Lys Ser
            500                 505                 510

Glu Gln Leu Leu Thr Ala Ser Glu Arg Asn Leu Asp Phe Arg Asp Leu
        515                 520                 525

Tyr Asp Pro Arg Asp Lys Ala Lys Leu Leu Tyr Asn Asn Leu Asp Ala
    530                 535                 540

Phe Gly Ile Met Asp Tyr Thr Leu Thr Gly Lys Val Glu Asp Asn His
545                 550                 555                 560

Asp Asp Thr Asn Arg Ile Ile Thr Val Tyr Met Gly Lys Arg Pro Glu
                565                 570                 575

Gly Glu Asn Ala Ser Tyr His Leu Ala Gly Gly Gln Ala Gln Gln
            580                 585                 590

Ile Val Pro Ile Ala Glu Lys Cys Phe Asp His Ala Ala Gly Thr Ser
        595                 600                 605

Tyr Leu Val Gly Glu Thr Trp Glu Lys Pro Tyr Gln Gly Trp Met Met
    610                 615                 620

Val Asp Cys Thr Cys Leu Gly Glu Gly Ser Gly Arg Ile Thr Cys Thr
625                 630                 635                 640

Ser Arg Asn Arg Cys Asn Asp Gln Asp Thr Arg Thr Ser Tyr Arg Ile
                645                 650                 655

Gly Asp Thr Trp Ser Lys Lys Asp Asn Arg Gly Asn Leu Leu Gln Cys
            660                 665                 670
```

Ile Cys Thr Gly Asn Gly Arg Gly Glu Trp Lys Cys Glu Arg His Thr
            675                 680                 685

Ser Val Gln Thr Thr Ser Ser Gly Ser Gly Pro Phe Thr Asp Val Arg
    690                 695                 700

<210> SEQ ID NO 25
<211> LENGTH: 704
<212> TYPE: PRT
<213> ORGANISM: Artificial Sequence
<220> FEATURE:
<223> OTHER INFORMATION: Original CSSK with modified alpha signal
      sequence

<400> SEQUENCE: 25

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg Val Gln Ala Gln Gln Ile Val Pro Ile Ala Glu
                85                  90                  95

Lys Cys Phe Asp His Ala Ala Gly Thr Ser Tyr Leu Val Gly Glu Thr
            100                 105                 110

Trp Glu Lys Pro Tyr Gln Gly Trp Met Met Val Asp Cys Thr Cys Leu
        115                 120                 125

Gly Glu Gly Ser Gly Arg Ile Thr Cys Thr Ser Arg Asn Arg Cys Asn
    130                 135                 140

Asp Gln Asp Thr Arg Thr Ser Tyr Arg Ile Gly Asp Thr Trp Ser Lys
145                 150                 155                 160

Lys Asp Asn Arg Gly Asn Leu Leu Gln Cys Ile Cys Thr Gly Asn Gly
                165                 170                 175

Arg Gly Glu Trp Lys Cys Glu Arg His Thr Ser Val Gln Thr Thr Ser
            180                 185                 190

Ser Gly Ser Gly Pro Phe Thr Asp Val Arg Ile Ala Gly Pro Glu Trp
        195                 200                 205

Leu Leu Asp Arg Pro Ser Val Asn Asn Ser Gln Leu Val Val Ser Val
    210                 215                 220

Ala Gly Thr Val Glu Gly Thr Asn Gln Asp Ile Ser Leu Lys Phe Phe
225                 230                 235                 240

Glu Ile Asp Leu Thr Ser Arg Pro Ala His Gly Gly Lys Thr Glu Gln
                245                 250                 255

Gly Leu Ser Pro Lys Ser Lys Pro Phe Ala Thr Asp Ser Gly Ala Met
            260                 265                 270

Ser His Lys Leu Glu Lys Ala Asp Leu Leu Lys Ala Ile Gln Glu Gln
        275                 280                 285

Leu Ile Ala Asn Val His Ser Asn Asp Asp Tyr Phe Glu Val Ile Asp
    290                 295                 300

Phe Ala Ser Asp Ala Thr Ile Thr Asp Pro Asn Gly Lys Val Tyr Phe
305                 310                 315                 320

Ala Asp Lys Asp Gly Ser Val Thr Leu Pro Thr Gln Pro Val Gln Glu

```
                325                 330                 335
Phe Leu Leu Ser Gly His Val Arg Val Arg Pro Tyr Lys Glu Lys Pro
            340                 345                 350
Ile Gln Asn Gln Ala Lys Ser Val Asp Val Glu Tyr Thr Val Gln Phe
        355                 360                 365
Thr Pro Leu Asn Pro Asp Asp Asp Phe Arg Pro Gly Leu Lys Asp Thr
    370                 375                 380
Lys Leu Leu Lys Thr Leu Ala Ile Gly Asp Thr Ile Thr Ser Gln Glu
385                 390                 395                 400
Leu Leu Ala Gln Ala Gln Ser Ile Leu Asn Lys Asn His Pro Gly Tyr
                405                 410                 415
Thr Ile Tyr Glu Arg Asp Ser Ser Ile Val Thr His Asp Asn Asp Ile
            420                 425                 430
Phe Arg Thr Ile Leu Pro Met Asp Gln Glu Leu Ser Tyr Arg Val Lys
        435                 440                 445
Asn Arg Glu Gln Ala Tyr Arg Ile Asn Lys Lys Ser Gly Leu Asn Glu
    450                 455                 460
Glu Ile Asn Asn Thr Asp Leu Ile Ser Glu Lys Tyr Tyr Val Leu Lys
465                 470                 475                 480
Lys Gly Glu Lys Pro Tyr Asp Pro Phe Asp Arg Ser His Leu Lys Leu
                485                 490                 495
Phe Thr Ile Lys Tyr Val Asp Val Asp Thr Asn Glu Leu Leu Lys Ser
            500                 505                 510
Glu Gln Leu Leu Thr Ala Ser Glu Arg Asn Leu Asp Phe Arg Asp Leu
        515                 520                 525
Tyr Asp Pro Arg Asp Lys Ala Lys Leu Leu Tyr Asn Asn Leu Asp Ala
    530                 535                 540
Phe Gly Ile Met Asp Tyr Thr Leu Thr Gly Lys Val Glu Asp Asn His
545                 550                 555                 560
Asp Asp Thr Asn Arg Ile Ile Thr Val Tyr Met Gly Lys Arg Pro Glu
                565                 570                 575
Gly Glu Asn Ala Ser Tyr His Leu Ala Gly Gly Gln Ala Gln Gln
            580                 585                 590
Ile Val Pro Ile Ala Glu Lys Cys Phe Asp His Ala Ala Gly Thr Ser
        595                 600                 605
Tyr Leu Val Gly Glu Thr Trp Glu Lys Pro Tyr Gln Gly Trp Met Met
    610                 615                 620
Val Asp Cys Thr Cys Leu Gly Glu Gly Ser Gly Arg Ile Thr Cys Thr
625                 630                 635                 640
Ser Arg Asn Arg Cys Asn Asp Gln Asp Thr Arg Thr Ser Tyr Arg Ile
                645                 650                 655
Gly Asp Thr Trp Ser Lys Lys Asp Asn Arg Gly Asn Leu Leu Gln Cys
            660                 665                 670
Ile Cys Thr Gly Asn Gly Arg Gly Glu Trp Lys Cys Glu Arg His Thr
        675                 680                 685
Ser Val Gln Thr Thr Ser Ser Gly Ser Gly Pro Phe Thr Asp Val Arg
    690                 695                 700
```

<210> SEQ ID NO 26
<211> LENGTH: 2115
<212> TYPE: DNA
<213> ORGANISM: Artificial Sequence
<220> FEATURE:
<223> OTHER INFORMATION: Original CSSK with modified alpha signal
      sequence

<400> SEQUENCE: 26

```
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaaggggta     240
tctctcgaga aaagagtgca agctcaacaa attgtgccca tagctgagaa gtgttttgat     300
catgctgctg ggacttccta tttggtcgga gaaacgtggg agaagcccta ccaaggctgg     360
atgatggtag attgtacttg cctgggagaa ggcagcggac gcatcacttg cacttctaga     420
aatagatgca acgatcagga cacaaggaca tcctatagaa ttggagacac ctggagcaag     480
aaggataatc gaggaaacct gctccagtgc atctgcacag caacggccg aggagagtgg     540
aagtgtgaga ggcacacctc tgtgcagacc acatcgagcg atctggccc cttcaccgat     600
gttcgtattg ctggacctga gtggctgcta gaccgtccat ctgtcaacaa cagccaatta     660
gttgttagcg ttgctggtac tgttgagggg acgaatcaag acattagtct taaattttt      720
gaaatcgatc taacatcacg acctgctcat ggaggaaaga cagagcaagg cttaagtcca     780
aaatcaaaac catttgctac tgatagtggc gcgatgtcac ataaacttga aaagctgac     840
ttactaaagg ctattcaaga acaattgatc gctaacgtcc acagtaacga cgactacttt     900
gaggtcattg attttgcaag cgatgcaacc attactgatc caaacggcaa ggtctacttt     960
gctgacaaag atggttcggt aaccttgccg acccaacctg tccaagaatt tttgctaagc    1020
ggacatgtgc gcgttagacc atataaagaa aaaccaatac aaaaccaagc gaaatctgtt    1080
gatgtggaat atactgtaca gtttactccc ttaaaccctg atgacgattt cagaccaggt    1140
ctcaaagata ctaagctatt gaaaacacta gctatcggtg acaccatcac atctcaagaa    1200
ttactagctc aagcacaaag cattttaaac aaaaccacc aggctatac gatttatgaa     1260
cgtgactcct caatcgtcac tcatgacaat gacatttcc gtacgatttt accaatggat    1320
caagagttat cttaccgtgt aaaaatcgg gaacaagctt ataggatcaa taaaaaatct    1380
ggtctgaatg aagaaataaa caacactgac ctgatctctg agaaatatta cgtccttaaa    1440
aaagggaaa agccgtatga tcccttttgat cgcagtcact tgaaactgtt caccatcaaa    1500
tacgttgatg tcgataccaa cgaattgcta aaaagtgagc agctcttaac agctagcgaa    1560
cgtaacttag acttcagaga tttatacgat cctcgtgata aggctaaact actctacaac    1620
aatctcgatg ctttttggtat tatggactat accttaactg aaaagtaga ggataatcac    1680
gatgacacca accgtatcat aaccgtttat atgggcaagc gacccgaagg agagaatgct    1740
agctatcatt tagccggtgg cggacaagct caacaaattg tgcccatagc tgagaagtgt    1800
tttgatcatg ctgctgggac ttcctatttg gtcggagaaa cgtgggagaa gccctaccaa    1860
ggctggatga tggtagattg tacttgcctg ggagaaggca gcggacgcat cacttgcact    1920
tctagaaata gatgcaacga tcaggacaca aggacatcct atagaattgg agacacctgg    1980
agcaagaagg ataatcgagg aaacctgctc cagtgcatct gcacaggcaa cggccgagga    2040
gagtggaagt gtgagaggca cacctctgtg cagaccacat cgagcggatc tggcccttc    2100
accgatgttc gttag                                                    2115
```

<210> SEQ ID NO 27
<211> LENGTH: 704
<212> TYPE: PRT

<213> ORGANISM: Artificial Sequence
<220> FEATURE:
<223> OTHER INFORMATION: CSSK modified N-terminal original C-terminal with modified alpha signal sequence

<400> SEQUENCE: 27

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Lys Glu Glu Gly Val
65                  70                  75                  80

Ser Leu Glu Lys Arg Val Gln Ala Gln Gln Ile Val Pro Ile Ala Glu
                85                  90                  95

Lys Cys Phe Asp His Ala Ala Gly Thr Ser Tyr Leu Val Gly Glu Thr
            100                 105                 110

Trp Glu Lys Pro Tyr Gln Gly Trp Met Met Val Asp Cys Thr Cys Leu
        115                 120                 125

Gly Glu Gly Ser Gly Arg Ile Thr Cys Thr Ser Arg Asn Arg Cys Asn
    130                 135                 140

Asp Gln Asp Thr Arg Thr Ser Tyr Arg Ile Gly Asp Thr Trp Ser Lys
145                 150                 155                 160

Lys Asp Asn Arg Gly Asn Leu Leu Gln Cys Ile Cys Thr Gly Asn Gly
                165                 170                 175

Arg Gly Glu Trp Lys Cys Glu Arg His Thr Ser Val Gln Thr Thr Ser
            180                 185                 190

Ser Gly Ser Gly Pro Phe Thr Asp Val Arg Ile Ala Gly Pro Glu Trp
        195                 200                 205

Leu Leu Asp Arg Pro Ser Val Asn Asn Ser Gln Leu Val Val Ser Val
    210                 215                 220

Ala Gly Thr Val Glu Gly Thr Asn Gln Asp Ile Ser Leu Lys Phe Phe
225                 230                 235                 240

Glu Ile Asp Leu Thr Ser Arg Pro Ala His Gly Gly Lys Thr Glu Gln
                245                 250                 255

Gly Leu Ser Pro Lys Ser Lys Pro Phe Ala Thr Asp Ser Gly Ala Met
            260                 265                 270

Ser His Lys Leu Glu Lys Ala Asp Leu Leu Lys Ala Ile Gln Glu Gln
        275                 280                 285

Leu Ile Ala Asn Val His Ser Asn Asp Tyr Phe Glu Val Ile Asp
    290                 295                 300

Phe Ala Ser Asp Ala Thr Ile Thr Asp Pro Asn Gly Lys Val Tyr Phe
305                 310                 315                 320

Ala Asp Lys Asp Gly Ser Val Thr Leu Pro Thr Gln Pro Val Gln Glu
                325                 330                 335

Phe Leu Leu Ser Gly His Val Arg Val Arg Pro Tyr Lys Glu Lys Pro
            340                 345                 350

Ile Gln Asn Gln Ala Lys Ser Val Asp Val Glu Tyr Thr Val Gln Phe
        355                 360                 365

Thr Pro Leu Asn Pro Asp Asp Phe Arg Pro Gly Leu Lys Asp Thr
370                 375                 380
```

-continued

```
Lys Leu Leu Lys Thr Leu Ala Ile Gly Asp Thr Ile Thr Ser Gln Glu
385                 390                 395                 400

Leu Leu Ala Gln Ala Gln Ser Ile Leu Asn Lys Asn His Pro Gly Tyr
                405                 410                 415

Thr Ile Tyr Glu Arg Asp Ser Ser Ile Val Thr His Asp Asn Asp Ile
            420                 425                 430

Phe Arg Thr Ile Leu Pro Met Asp Gln Glu Leu Ser Tyr Arg Val Lys
        435                 440                 445

Asn Arg Glu Gln Ala Tyr Arg Ile Asn Lys Lys Ser Gly Leu Asn Glu
    450                 455                 460

Glu Ile Asn Asn Thr Asp Leu Ile Ser Glu Lys Tyr Tyr Val Leu Lys
465                 470                 475                 480

Lys Gly Glu Lys Pro Tyr Asp Pro Phe Asp Arg Ser His Leu Lys Leu
                485                 490                 495

Phe Thr Ile Lys Tyr Val Asp Val Asp Thr Asn Glu Leu Leu Lys Ser
            500                 505                 510

Glu Gln Leu Leu Thr Ala Ser Glu Arg Asn Leu Asp Phe Arg Asp Leu
        515                 520                 525

Tyr Asp Pro Arg Asp Lys Ala Lys Leu Leu Tyr Asn Asn Leu Asp Ala
    530                 535                 540

Phe Gly Ile Met Asp Tyr Thr Leu Thr Gly Lys Val Glu Asp Asn His
545                 550                 555                 560

Asp Asp Thr Asn Arg Ile Ile Thr Val Tyr Met Gly Lys Arg Pro Glu
                565                 570                 575

Gly Glu Asn Ala Ser Tyr His Leu Ala Gly Gly Gln Ala Gln Gln
            580                 585                 590

Ile Val Pro Ile Ala Glu Lys Cys Phe Asp His Ala Ala Gly Thr Ser
        595                 600                 605

Tyr Leu Val Gly Glu Thr Trp Glu Lys Pro Tyr Gln Gly Trp Met Met
    610                 615                 620

Val Asp Cys Thr Cys Leu Gly Glu Gly Ser Gly Arg Ile Thr Cys Thr
625                 630                 635                 640

Ser Arg Asn Arg Cys Asn Asp Gln Asp Thr Arg Thr Ser Tyr Arg Ile
                645                 650                 655

Gly Asp Thr Trp Ser Lys Lys Asp Asn Arg Gly Asn Leu Leu Gln Cys
            660                 665                 670

Ile Cys Thr Gly Asn Gly Arg Gly Glu Trp Lys Cys Glu Arg His Thr
        675                 680                 685

Ser Val Gln Thr Thr Ser Ser Gly Ser Gly Pro Phe Thr Asp Val Arg
    690                 695                 700
```

<210> SEQ ID NO 28
<211> LENGTH: 2115
<212> TYPE: DNA
<213> ORGANISM: Artificial Sequence
<220> FEATURE:
<223> OTHER INFORMATION: CSSK original 5' modified 3' with modified
      alpha signal sequence

<400> SEQUENCE: 28

```
atgagatttc cttcaatttt tactgcagtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc cattttccaa cagcacaaat   180
aacgggttat tgtttataaa tactactatt gccagcattg ctgctaaaga agaaggggta   240
```

```
tctctcgaga aaagagttca agcccagcag attgttccaa tcgctgagaa gtgtttcgat    300
cacgctgctg gtacttcata cttggtcggt gaaacctggg aaaagccata ccagggatgg    360
atgatggttg actgcacctg tttaggtgaa ggttccggta gaatcacctg tacctccaga    420
aacagatgta acgaccagga caccagaacc tcttacagaa tcggtgatac ctggtccaag    480
aaggacaaca gaggtaacct gttgcagtgt atctgtaccg gtaacggtcg tggagaatgg    540
aagtgcgaga gacacacttc cgttcaaact acttcttccg gttccggtcc attcactgat    600
gttagaatcg ctggtccaga atggttgttg gacagaccat ccgttaacaa ctcccagttg    660
gttgtttctg ttgctggtac tgttgaggga actaaccagg acatctcctt gaagttcttc    720
gagatcgact tgacttctag accagctcat ggtggaaaga ctgagcaagg cttaagtcca    780
aaatcaaaac catttgctac tgatagtggc gcgatgtcac ataaacttga aaagctgac     840 ttactaaagg ctattcaaga acaattgatc gctaacgtcc acagtaacga cgactacttt    900
gaggtcattg atttttgcaag cgatgcaacc attactgatc aaacggcaa ggtctacttt     960 gctgacaaag atggttcggt aaccttgccg acccaacctg tccaagaatt tttgctaagc   1020
ggacatgtgc gcgttagacc atataaagaa aaaccaatac aaaaccaagc gaaatctgtt   1080
gatgtggaat atactgtaca gtttactccc ttaaaccctg atgacgattt cagaccaggt   1140
ctcaaagata ctaagctatt gaaaacacta gctatcggtg acaccatcac atctcaagaa   1200
ttactagctc aagcacaaag catttttaaac aaaaaccacc caggctatac gatttatgaa   1260
cgtgactcct caatcgtcac tcatgacaat gacattttcc gtacgatttt accaatggat   1320
caagagttat cttaccgtgt taaaaatcgg aacaagcctt ataggatcaa taaaaaatct   1380
ggtctgaatg aagaaataaa caacactgac ctgatctctg agaaatatta cgtccttaaa   1440
aaaggggaaa agccgtatga tccctttgat cgcagtcact tgaaactgtt caccatcaaa   1500
tacgttgatg tcgataccaa cgaattgcta aaaagtgagc agctcttaac agctagcgaa   1560
cgtaacttag acttcagaga tttatacgat cctcgtgata aggctaaact actctacaac   1620
aatctcgatg cttttggtat tatggactat accttaactg aaaagtaga ggataatcac    1680 gatgacacca accgtatcat aaccgtttat atgggcaagc gacccgaagg agagaatgct   1740
agctatcatt tagccggtgg cggacaagct caacaaattg tgcccatagc tgagaagtgt   1800
tttgatcatg ctgctgggac ttcctatttg gtcggagaaa cgtgggagaa gccctaccaa   1860
ggctggatga tggtagattg tacttgcctg ggagaaggca gcggacgcat cacttgcact   1920
tctagaaata gatgcaacga tcaggacaca aggacatcct atagaattgg agacacctgg   1980
agcaagaagg ataatcgagg aaacctgctc cagtgcatct gcacaggcaa cggccgagga   2040
gagtggaagt gtgagaggca cacctctgtg cagaccacat cgagcggatc tggccccttc   2100
accgatgttc gttag                                                    2115
```

<210> SEQ ID NO 29
<211> LENGTH: 704
<212> TYPE: PRT
<213> ORGANISM: Artificial Sequence
<220> FEATURE:
<223> OTHER INFORMATION: CSSK original N-terminal modified C-terminal
      with modified alpha signal sequence

<400> SEQUENCE: 29

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln

```
            20                  25                  30
Ile Pro Ala Glu Ala Val Ile Gly Tyr Ser Asp Leu Glu Gly Asp Phe
            35                  40                  45
Asp Val Ala Val Leu Pro Phe Ser Asn Ser Thr Asn Asn Gly Leu Leu
 50                  55                  60
Phe Ile Asn Thr Thr Ile Ala Ser Ile Ala Ala Lys Glu Glu Gly Val
 65                  70                  75                  80
Ser Leu Glu Lys Arg Val Gln Ala Gln Gln Ile Val Pro Ile Ala Glu
                85                  90                  95
Lys Cys Phe Asp His Ala Ala Gly Thr Ser Tyr Leu Val Gly Glu Thr
                100                 105                 110
Trp Glu Lys Pro Tyr Gln Gly Trp Met Met Val Asp Cys Thr Cys Leu
                115                 120                 125
Gly Glu Gly Ser Gly Arg Ile Thr Cys Thr Ser Arg Asn Arg Cys Asn
                130                 135                 140
Asp Gln Asp Thr Arg Thr Ser Tyr Arg Ile Gly Asp Thr Trp Ser Lys
145                 150                 155                 160
Lys Asp Asn Arg Gly Asn Leu Leu Gln Cys Ile Cys Thr Gly Asn Gly
                165                 170                 175
Arg Gly Glu Trp Lys Cys Glu Arg His Thr Ser Val Gln Thr Thr Ser
                180                 185                 190
Ser Gly Ser Gly Pro Phe Thr Asp Val Arg Ile Ala Gly Pro Glu Trp
                195                 200                 205
Leu Leu Asp Arg Pro Ser Val Asn Asn Ser Gln Leu Val Ser Val
                210                 215                 220
Ala Gly Thr Val Glu Gly Thr Asn Gln Asp Ile Ser Leu Lys Phe Phe
225                 230                 235                 240
Glu Ile Asp Leu Thr Ser Arg Pro Ala His Gly Gly Lys Thr Glu Gln
                245                 250                 255
Gly Leu Ser Pro Lys Ser Lys Pro Phe Ala Thr Asp Ser Gly Ala Met
                260                 265                 270
Ser His Lys Leu Glu Lys Ala Asp Leu Leu Lys Ala Ile Gln Glu Gln
                275                 280                 285
Leu Ile Ala Asn Val His Ser Asn Asp Asp Tyr Phe Glu Val Ile Asp
                290                 295                 300
Phe Ala Ser Asp Ala Thr Ile Thr Asp Pro Asn Gly Lys Val Tyr Phe
305                 310                 315                 320
Ala Asp Lys Asp Gly Ser Val Thr Leu Pro Thr Gln Pro Val Gln Glu
                325                 330                 335
Phe Leu Leu Ser Gly His Val Arg Val Arg Pro Tyr Lys Glu Lys Pro
                340                 345                 350
Ile Gln Asn Gln Ala Lys Ser Val Asp Val Glu Tyr Thr Val Gln Phe
                355                 360                 365
Thr Pro Leu Asn Pro Asp Asp Asp Phe Arg Pro Gly Leu Lys Asp Thr
                370                 375                 380
Lys Leu Leu Lys Thr Leu Ala Ile Gly Asp Thr Ile Thr Ser Gln Glu
385                 390                 395                 400
Leu Leu Ala Gln Ala Gln Ser Ile Leu Asn Lys Asn His Pro Gly Tyr
                405                 410                 415
Thr Ile Tyr Glu Arg Asp Ser Ser Ile Val Thr His Asp Asn Asp Ile
                420                 425                 430
Phe Arg Thr Ile Leu Pro Met Asp Gln Glu Leu Ser Tyr Arg Val Lys
                435                 440                 445
```

Asn Arg Glu Gln Ala Tyr Arg Ile Asn Lys Lys Ser Gly Leu Asn Glu
    450                 455                 460

Glu Ile Asn Asn Thr Asp Leu Ile Ser Glu Lys Tyr Tyr Val Leu Lys
465                 470                 475                 480

Lys Gly Glu Lys Pro Tyr Asp Pro Phe Asp Arg Ser His Leu Lys Leu
                485                 490                 495

Phe Thr Ile Lys Tyr Val Asp Val Asp Thr Asn Glu Leu Leu Lys Ser
            500                 505                 510

Glu Gln Leu Leu Thr Ala Ser Glu Arg Asn Leu Asp Phe Arg Asp Leu
        515                 520                 525

Tyr Asp Pro Arg Asp Lys Ala Lys Leu Leu Tyr Asn Asn Leu Asp Ala
530                 535                 540

Phe Gly Ile Met Asp Tyr Thr Leu Thr Gly Lys Val Glu Asp Asn His
545                 550                 555                 560

Asp Asp Thr Asn Arg Ile Ile Thr Val Tyr Met Gly Lys Arg Pro Glu
                565                 570                 575

Gly Glu Asn Ala Ser Tyr His Leu Ala Gly Gly Gln Ala Gln Gln
                580                 585                 590

Ile Val Pro Ile Ala Glu Lys Cys Phe Asp His Ala Ala Gly Thr Ser
            595                 600                 605

Tyr Leu Val Gly Glu Thr Trp Glu Lys Pro Tyr Gln Gly Trp Met Met
610                 615                 620

Val Asp Cys Thr Cys Leu Gly Glu Gly Ser Gly Arg Ile Thr Cys Thr
625                 630                 635                 640

Ser Arg Asn Arg Cys Asn Asp Gln Asp Thr Arg Thr Ser Tyr Arg Ile
                645                 650                 655

Gly Asp Thr Trp Ser Lys Lys Asp Asn Arg Gly Asn Leu Leu Gln Cys
            660                 665                 670

Ile Cys Thr Gly Asn Gly Arg Gly Glu Trp Lys Cys Glu Arg His Thr
        675                 680                 685

Ser Val Gln Thr Thr Ser Ser Gly Ser Gly Pro Phe Thr Asp Val Arg
    690                 695                 700

<210> SEQ ID NO 30
<211> LENGTH: 21
<212> TYPE: DNA
<213> ORGANISM: Artificial Sequence
<220> FEATURE:
<223> OTHER INFORMATION: 5' AOX1 forward primer sequence

<400> SEQUENCE: 30
gactggttcc aattgacaag c                                                21

<210> SEQ ID NO 31
<211> LENGTH: 21
<212> TYPE: DNA
<213> ORGANISM: Artificial Sequence
<220> FEATURE:
<223> OTHER INFORMATION: 3' AOX1 reverse primer

<400> SEQUENCE: 31
gcaaatggca ttctgacatc c                                                21

<210> SEQ ID NO 32
<211> LENGTH: 33
<212> TYPE: DNA
<213> ORGANISM: Artificial Sequence
<220> FEATURE:

```
<223> OTHER INFORMATION: Forward Primer

<400> SEQUENCE: 32
gacagcctcg agaaaagagt gcaagctcaa caa                              33

<210> SEQ ID NO 33
<211> LENGTH: 33
<212> TYPE: DNA
<213> ORGANISM: Artificial Sequence
<220> FEATURE:
<223> OTHER INFORMATION: Primer sequence

<400> SEQUENCE: 33
gacagcctcg agaaaagagt gcaagctcaa caa                              33
```

GENETICALLY MODIFIED YEAST CELL AND IMPROVED PROCESS FOR PRODUCTION OF CLOT-SPECIFIC STREPTOKINASE

FIELD OF INVENTION

The present invention relates to genetically modified yeast cells for expression of clot specific streptokinase (CSSK) protein for improved production of CSSK. The present invention also relates to preparation of a vector comprising expression sequences of clot specific streptokinase. The vector has a modified alpha signal sequence and a CSSK codon sequence for expressing CSSK in yeast cells.

BACKGROUND OF THE INVENTION

In recent years, thrombolytic therapy with fibrinolytic agents, such as Streptokinase (SK), tissue plasminogen activator (TPA) or urokinase (UK) has revolutionized the clinical management of diverse circulatory diseases e.g., deep-vein thrombosis, pulmonary embolism and myocardial infarction. These agents exert their fibrinolytic effects through activation of plasminogen (PG) in the circulation by cleavage of the scissile peptide bond between residues 561 and 562 in PG. As a result, the inactive zymogen is transformed to its active form, the serine protease, plasmin (PN), which then acts on fibrin to degrade the latter into soluble degradation products. Activation of PG to PN can be catalyzed by TPA, the SK-plasminogen complex, and UK, each of which can cleave the scissile peptide bond in PG.

Unlike UK and TPA, SK has no proteolytic activity of its own, and it activates PG to PN indirectly by first forming a high-affinity equimolar complex with PG, known as the activator complex (reviewed in Castellino, F. J., 1981, Chem. Rev. 81: 431). Due to a lack of any appreciable fibrin clot-specificity in SK, the administration of SK can cause systemic PG activation, resulting in hemorrhagic complications due to the proteolytic degradation of blood factors by the plasmin generated throughout the circulatory system. In the past, the gene encoding for SK has been isolated from its natural source (*Streptococcus*) and cloned into several heterologous micro-organisms such as yeast (Hagenson, M. J., 1989, Enzyme. Microb. Technol. 11:650), bacteria such as *E. coli* (Malke, H, Ferretti, J. J., 1984, Proc. Nat'l. Acad. Sci. 81: 3557), other species of *Streptococcus* (Malke, H., 1984, Mol. Gen. Genet. 196:360), and *Bacillus* (Wong, S. L., 1994, Applied and Env. Microbiol. 1:517).

U.S. Pat. Nos. 7,163,817 and 8,143,027 disclose creation of novel clot-specific streptokinase proteins that contain SK or functionally relevant parts thereof, connected with fibrin binding domains of human fibronectin that confer fibrin affinity and altered plasminogen activation characteristics. The altered plasminogen activation involves an initial period of lag of several minutes' duration in the rate of PG activation, which is followed by high rates of PG activation akin to that of native SK.

Fibrin affinity and delayed PG activation in the CSSK chimeric proteins confer distinct advantages in the treatment of a subject in need of thrombolytic therapy. Specifically, after injection into the body, while the chimeric PG activator proteins are still in an inactive or partially active state, they bind to the pathological fibrin clot in the vascular system. However, after an initial lag, these will become fully activated while bound to the clot, thereby avoiding the systemic PG activation coincident with natural SK administration. Thus, the fibrin affinity of CSSK confers an ability to target itself to the immediate locale of the pathological clot and thus help build up therapeutically effective concentrations of the activator therein; the initially slowed kinetics of PG activation result in an overall diminished generation of free plasmin in the circulation prior to their localization to the site of circulatory impedance induced by the pathological fibrin clot. The net result is a continued and more efficient fibrinolysis at the target sustained by lowered therapeutically effective dosages of CSSK.

The development of CSSK has been a boon to the medical community. However, prior art methods to produce CSSK are time-consuming and laborious, resulting in low yield and high production costs.

In the method known in the art, clot specific streptokinase is produced intracellularly in *E. coli*, but the biologically-active protein is obtained by solubilization in urea/WO guanidinium chloride (strong chaotropes), and subsequent refolding. The in vitro refolding step is time-consuming and can be undertaken with high efficiency at a very low protein concentration. In addition, the *E. coli* cell wall contains lipopolysaccharides that are pyrogenic, and all *E. coli* based processes requires steps to remove these endotoxins.

Thus, there is a need in the art for an improved method of making clot specific streptokinase, particularly methods that improve on bacterial CSSK expression systems.

Although expression in yeast cells has desirable attributes, yeast expression is also not without drawbacks. For example, in some yeasts, transformants can express widely varying amounts of protein, possibly due to differences in site of plasmid integration or difference in expression cassette copy number. These drawbacks require many rounds of diagnosis and screening procedure to obtain transformants to get a high producing clone. Positive transformed cells can be characterized by polymerase chain reaction (PCR) or by Southern blot analysis to corroborate the integration of DNA fragment. In order to analyze the expression of protein of interest in a yeast expression system, reverse transcription can be used together with PCR or Northern blot technique. However, depending upon polypeptide composition and required post-translational modification, the protein levels might not always be in consonance with the transcription level. Further, conventional methods of screening of yeast clones involves SDS-PAGE analysis of direct or concentrated supernatants which is very tedious (due to low yield, concentrating the culture media of plethora of transformants etc.) for screening thousands of clones least one misses a true, and desirable, hyper-producer clone.

Thus, there is a need in the art for a process for producing CSSK in non-bacterial species, such as yeast, and for methods for screening yeast transformants expressing biologically active CSSK, that does not suffer from the above deficiencies.

OBJECTIVE OF THE INVENTION

An objective of the present invention is to provide an expression cassette comprising a polynucleotide, said polynucleotide comprising a yeast methanol inducible promotor sequence, a modified alpha signal gene sequence, a nucleic acid sequence encoding clot specific streptokinase and a transcription terminator sequence.

Another objective of the present invention is to provide an expression vector for transforming a yeast cell, wherein the expression vector comprises at least one expression cassette.

Another objective is to provide a genetically modified yeast cell containing an expression cassette, said expression cassette further comprising a hybrid polynucleotide comprising a yeast methanol inducible promotor sequence, a modified alpha signal gene sequence, a nucleic acid sequence having 85% homology to clot specific streptokinase and a transcription terminator sequence, wherein the sequence encoding clot specific streptokinase is selected from the group consisting of SEQ ID NO: 2, SEQ ID NO: 4, SEQ ID NO: 6 and SEQ ID NO: 8.

Yet another objective of the present invention is to provide a polynucleotide having the nucleic acid sequence selected from the group consisting of SEQ ID NO: 4, SEQ ID NO: 6, SEQ ID NO: 8, SEQ ID NO: 23, SEQ ID NO: 26 and SEQ ID NO: 28.

Another objective of the present invention is to provide a transformed yeast cell expressing a clot specific streptokinase (CSSK), said CSSK comprising: (a) streptokinase (SK) produced by *Streptococcus equisimilis*, or a derivative of SK having the ability to activate plasminogen; and (b) fibrin binding domains 4 and 5 (FBD 4,5) of human fibronectin, or a derivative of FBD 4,5 thereof having fibrin affinity.

Yet another objective of the present invention is to provide a clot specific streptokinase produced by the transformed yeast cell, wherein the clot specific streptokinase is glycosylated and has a molecular weight of 80,515 Da.

Still another objective of the present invention is to provide a composition comprising the clot specific streptokinase and a pharmaceutically acceptable carrier.

Another objective of the present invention is to provide a method of treating or preventing a disease in a subject in need thereof, comprising administering to the subject by way of injection or infusion a therapeutically effective amount of the composition.

Yet another objective of the present invention is to provide a method of screening a yeast cell to identify a transformed yeast cell producing clot specific streptokinase.

SUMMARY OF THE INVENTION

In an embodiment, the present invention relates to a genetically modified yeast cell containing an expression cassette, said expression cassette further comprising a hybrid polynucleotide comprising a yeast methanol inducible promotor sequence, a modified alpha signal gene sequence, a nucleic acid sequence having 85% homology to clot specific streptokinase and a transcription terminator sequence, wherein the sequence encoding clot specific streptokinase is selected from the group consisting of SEQ ID NO: 2, SEQ ID NO: 4, SEQ ID NO: 6 and SEQ ID NO: 8.

In another embodiment, the present invention relates to the genetically modified yeast cell having an expression vector comprised of the expression cassette.

In an aspect, the present invention relates to an expression cassette comprising a hybrid polynucleotide comprising a yeast methanol inducible promotor sequence, a modified alpha signal gene sequence, a nucleic acid sequence having 85% homology to clot specific streptokinase and a transcription terminator sequence, wherein the sequence encoding clot specific streptokinase is selected from the group consisting of SEQ ID NO: 2, SEQ ID NO: 4, SEQ ID NO: 6 and SEQ ID NO: 8.

In another aspect, the present invention provides an expression cassette comprising a polynucleotide, said polynucleotide comprising a yeast methanol inducible promotor sequence, a modified alpha signal gene sequence, a nucleic acid sequence encoding clot specific streptokinase and a transcription terminator sequence, wherein the nucleic acid sequence encoding clot specific streptokinase is selected from the group consisting of SEQ ID NO: 2, SEQ ID NO: 4, SEQ ID NO: 6 and SEQ ID NO: 8.

Another aspect of the present invention provides an expression vector for transforming a yeast cell, wherein the expression vector comprises at least one expression cassette.

Yet another aspect of the present invention provides an expression vector comprising a polynucleotide having at least 85% identity to a polynucleotide sequence selected from the group consisting of SEQ ID NO: 2, SEQ ID NO: 4, SEQ ID NO: 6, SEQ ID NO: 8, SEQ ID NO: 23, SEQ ID NO: 26 and SEQ ID NO: 28.

Still another aspect of the present invention provides an expression vector encoding a polypeptide having at least 85% identity to a polypeptide sequence selected from the group consisting of SEQ ID NO: 1, SEQ ID NO: 3, SEQ ID NO: 5, SEQ ID NO: 7, SEQ ID NO: 24, SEQ ID NO: 25, SEQ ID NO: 27 and SEQ ID NO: 29.

Another aspect of the present invention provides a polynucleotide having the nucleic acid sequence selected from the group consisting of SEQ ID NO: 4, SEQ ID NO: 6, SEQ ID NO: 8, SEQ ID NO: 23, SEQ ID NO: 26 and SEQ ID NO: 28. Yet another aspect of the present invention provides a transformed yeast cell expressing a clot specific streptokinase (CSSK), said CSSK comprising: (a) streptokinase (SK) produced by *Streptococcus equisimilis*, or a derivative of SK having the ability to activate plasminogen; and (b) fibrin binding domains 4 and 5 (FBD 4,5) of human fibronectin, or a derivative of FBD 4,5 thereof having fibrin affinity.

Still another aspect of the present invention provides a transformed yeast cell expressing a clot specific streptokinase (CSSK), wherein said CSSK comprises: a streptokinase sequence having at least 85% identity to the polypeptide sequence as set forth in SEQ ID NO: 11; and a polypeptide sequence having at least 85% identity to the polypeptide sequence as set forth in SEQ ID NO: 22, at each of the N- and C-termini of the streptokinase sequence.

Still another aspect is directed to a transformed yeast cell expressing the expression cassette described hereinabove wherein the nucleic acid sequence encoding a clot specific streptokinase (CSSK) comprising: (a) streptokinase (SK) produced by *Streptococcus equisimilis*, or a derivative of SK having the ability to activate plasminogen; and (b) fibrin binding domains 4 and 5 (FBD 4,5) of human fibronectin, or a derivative of FBD 4,5 thereof having fibrin affinity.

Yet another aspect of the present invention provides a transformed yeast cell comprising the expression cassette, wherein the yeast is methylotropic yeast selected from the group consisting of *Pichia, Hansenula, Torulopsis* and *Candida* species. Still another aspect of the present invention provides a so transformed *Pichia pastoris*.

An aspect of the present invention provides for a transformed *Pichia pastoris* having accession no. MTCC 25071.

Another aspect of the present invention provides a clot specific streptokinase produced by the transformed yeast cell, wherein the clot specific streptokinase is glycosylated and has a molecular weight of 80,515 Da.

Yet another aspect of the present invention provides a composition comprising the clot specific streptokinase and a pharmaceutically acceptable carrier.

Still another aspect of the present invention provides a method of treating or preventing a disease selected from the group consisting of myocardial infarction, vascular thromboses, pulmonary embolism, stroke, acute ischemic stroke, angina, pulmonary embolism, transient ischemic attack, deep vein thrombosis, thrombotic re-occlusion subsequent to a coronary intervention procedure, peripheral vascular thrombosis, heart failure, Syndrome X and a narrowing of at least one coronary artery in a subject in need thereof, comprising administering to the subject by way of injection or infusion a therapeutically effective amount of the composition.

Another aspect of the present invention provides a method of screening a yeast cell to identify a transformed yeast cell producing clot specific streptokinase, said method comprising: transforming at least one yeast cell with a vector to obtain a transformed yeast cell; culturing at least one transformed yeast cell in BMMY culture medium with methanol to induce expression of CSSK protein; separating the culture medium from the transformed yeast cell to obtain a supernatant; testing the supernatant for plasminogen activation; and identifying a transformed yeast cell producing clot specific streptokinase by detecting plasminogen activation in the supernatant of the cell.

An aspect of the present invention provides a method of site directed dissolution of blood clots comprising administering to a subject in need of such treatment an effective amount of a composition comprising the clot specific streptokinase and a pharmaceutically acceptable carrier.

BRIEF DESCRIPTION OF THE FIGURES

FIG. 3: Partial nucleotide (SEQ ID NO: 17) and amino acid (SEQ ID NO: 14) sequence of pPIC9K CSSK showing sequence and location of STE13 cleavage site which is removed in the recombinant vector. The underlined bases are removed after XhoI and NotI digestion.

FIG. 6A: Diagrammatic representation of the recombinant expression plasmid pPIC9K with alpha modified signal sequence preprotein.

FIG. 6B: Depiction of linearized recombinant plasmid. The CSSK encoding gene was cloned between XhoI and NotI restriction sites. Bgl II sites were used to linearize the plasmid prior to transformation.

FIG. 21: Individual blood flow data in femoral arteries of Cynomolgus monkeys administered CSSK by intravenous bolus.

BRIEF DESCRIPTION OF SEQUENCE LISTING

Figure 1A:
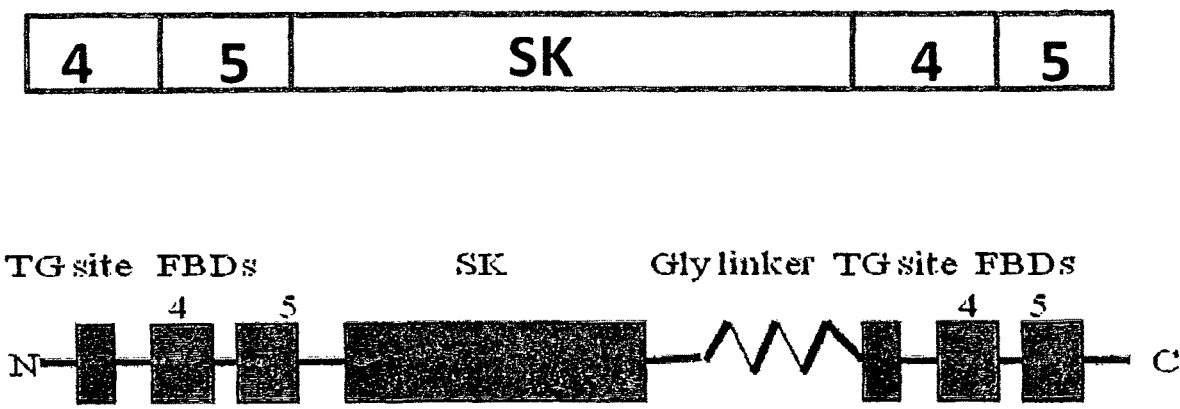
FIG. 1A: Schematic representation of the gene-blocks in the Clot Specific Streptokinase hybrid construct, with FBD (4,5) fused at the N- and C-terminals of SK.

SEQ ID NO: 1. CSSK amino acid sequence
SEQ ID NO: 2. CSSK nucleic acid sequence
SEQ ID NO: 3. CSSK sequence modified for Pichia (amino acid sequence)
SEQ ID NO: 4. CSSK sequence modified for Pichia (nucleic acid sequence)
SEQ ID NO: 5. CSSK modified N-terminal original C-terminal (amino acid sequence)
SEQ ID NO: 6. CSSK modified 5' original 3' (nucleic acid sequence)

SEQ ID NO: 7. CSSK original N-terminal modified C-terminal (amino acid sequence)

SEQ ID NO: 8. CSSK original 5' modified 3' (nucleic acid sequence)

SEQ ID NO: 9. Modified alpha signal sequence (amino acid sequence)

SEQ ID NO: 10. Modified alpha signal sequence (nucleic acid sequence)

SEQ ID NO: 11. Streptokinase sequence (amino acid sequence)

SEQ ID NO: 12. SK C-terminal sequence with poly-glycine linker and transglutaminase site (amino acid sequence)

SEQ ID NO: 13. SK 3' sequence with poly-glycine linker and transglutaminase site (nucleic acid sequence)

SEQ ID NO: 14. Native alpha signal sequence (amino acid sequence)

SEQ ID NO: 15. Native alpha signal sequence (nucleic acid sequence)

SEQ ID NO: 16: Signal peptide sequence stretch (amino acid sequence)

SEQ ID NO: 17. Partial vector sequence with AOX1 5' promoter and alpha sequence (nucleic acid sequence)

SEQ ID NO: 18. Partial vector sequence (nucleic acid sequence)

SEQ ID NO: 19: Polypeptide encoded by partial vector sequence (amino acid sequence)

SEQ ID NO: 20. Alpha signal sequence plus N-terminal CSSK (amino acid sequence)

SEQ ID NO: 21. Fibrin binding domains 4,5 (nucleic acid sequence)

SEQ ID NO: 22. Fibrin binding domains 4,5 (amino acid sequence)

SEQ ID NO: 23. CSSK sequence modified alpha sequence plus modified for *Pichia*. (nucleic acid sequence)

SEQ ID NO: 24. CSSK sequence modified alpha sequence plus modified for *Pichia*. (amino acid sequence)

SEQ ID NO: 25. Original CSSK with modified alpha signal sequence (amino acid sequence)

SEQ ID NO: 26. Original CSSK with modified alpha signal sequence (nucleic acid sequence)

SEQ ID NO: 27. CSSK modified N-terminal original C-terminal with modified alpha signal sequence (amino acid sequence)

SEQ ID NO: 28. CSSK original 5'modified 3' with modified alpha signal sequence (nucleic acid sequence)

SEQ ID NO: 29. CSSK original N-terminal modified C-terminal with modified alpha signal sequence (amino acid sequence)

SEQ ID NO: 30. 5'AOX1 forward primer

SEQ ID NO: 31. 3'AOX1 reverse primer

SEQ ID NO: 32. Forward primer

SEQ ID NO: 33. Primer sequence

DETAIL DESCRIPTION OF THE INVENTION

The invention will now be described in detail in connection with certain preferred and optional embodiments, so that various aspects thereof may be more fully understood and appreciated.

An embodiment of the present invention provides an expression cassette, a vector, a polynucleotide sequence, a transformed yeast cell, a clot specific streptokinase, a composition comprising the clot specific streptokinase, a method of treating a disease using the clot specific streptokinase and a method of screening transformed yeast cells. The modified microorganism *P. pastoris* pPIC9K-alpha modified CSSK/ GS115/B15 strain, transformed by introduction of the vector pPIC9K-alpha modified CSSK encoding CSSK has been deposited at International Microorganism Depository Authority, Microbial Type Culture Collection & Genebank, Institute of Microbial Technology, Sector 39-A, Chandigarh, India. The accession of said modified *P. pastoris* is MTCC 25071 and date of deposit is Oct. 19, 2015.

Clot-Specific Streptokinase

As used herein, "clot-specific streptokinase" or "CSSK" is defined as a chimeric polypeptide that combines (1) streptokinase (SK) produced by *Streptococcus equisimilis*, or derivative or variant forms of SK thereof, said SK or derivative or variant of SK having the ability to activate plasminogen; and (2) fragments of the human fibronectin gene that possess fibrin binding ability (e.g., fibrin binding domains 4 and 5 of human fibronectin), or derivative or variant forms of fibrin binding domains thereof having fibrin affinity. The disclosed CSSK thus has functional SK activity and can activate plasminogen to plasmin, and also has functional fibrin affinity via fibrin binding domains 4,5 of human fibronectin. This CSSK also has delayed PG activation kinetics relative to the immediate (i.e., without a distinct time-delay) activation kinetics of native SK expressed by *Streptococcus equisimilis*. CSSK and its expression in bacterial systems are disclosed in U.S. Pat. Nos. 7,163,817 and 8,143,027, the contents of both of which are incorporated by reference herein. As disclosed in these patents, CSSK has a distinct initial delay in activation kinetics relative to native SK. This delayed activation is correlated to the presence of trace amounts of plasmin in the system, indicating that CSSK requires plasmin for activation that is in contrast to native SK, which can activate plasminogen in the absence of any plasmin i.e. a via a plasmin-independent mechanism.

In accordance with the present invention, "derivatives" include fragments, portions, mutants, homologs, and mimetics from natural, synthetic or recombinant sources including fusion proteins. Derivatives may be derived by insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Additions to amino acid sequences include fusions with other peptides, polypeptides or proteins. A "variant" refers to a molecule substantially similar in structure and function to either the entire molecule, or to a fragment thereof. The term "fragment" refers to any functional subset of the molecule, that is, a shorter peptide which retains the desired biological activity CSSK variant polypeptides are contemplated within the scope of this application, as for example SK conjugated with different combinations of fibrin binding domains as disclosed in U.S. Pat. No. 8,143,027.

An embodiment of the present invention provides an expression cassette comprising a polynucleotide, said polynucleotide comprising a yeast methanol inducible promotor sequence, a modified alpha signal gene sequence, a nucleic acid sequence encoding clot specific streptokinase and a transcription terminator sequence, wherein the nucleic acid sequence encoding clot specific streptokinase is selected from the group consisting of SEQ ID NO: 2, SEQ ID NO: 4, SEQ ID NO: 6 and SEQ ID NO: 8.

In another embodiment of the present invention, there is provided an expression cassette, wherein the modified alpha signal gene sequence is as set forth in SEQ ID NO: 10.

In accordance with the present invention, the CSSK includes (a) a polypeptide sequence having at least 80%, 81%, 82%, 83%, 84%, 85%, 86%, 87%, 88%, 89%, 90%, 91%, 92%, 93%, 94%, 95%, 96%, 97%, 98%, or 99% or greater identity to the polypeptide sequence of Streptococcus equisimilis streptokinase (SEQ ID NO: 11); and (b) polypeptide sequence having at least 80%, 81%, 82%, 83%, 84%, 85%, 86%, 87%, 88%, 89%, 90%, 91%, 92%, 93%, 94%, 95%, 96%, 97%, 98%, or 99% or greater identity to the polypeptide sequence of the human fibrinogen fibrin binding domains 4,5 (FBD 4,5) (SEQ ID NO: 22), at the N-terminus, the C-terminus, or both of the N- and C-termini of the streptokinase polypeptide sequence. In accordance with the present invention, polypeptide sequence of CSSK has at least 85%, 86%, 87%, 88%, 89%, 90%, 91%, 92%, 93%, 94%, 95%, 96%, 97%, 98%, or 99% or greater identity to the polypeptide sequence selected from the group consisting of SEQ ID NO: 1, 3, 5, 7, 24, 25, 27 and 29. In accordance with the present invention, CSSK is encoded by a polynucleotide sequence having at least 85%, 86%, 87%, 88%, 89%, 90%, 91%, 92%, 93%, 94%, 95%, 96%, 97%, 98%, or 99% or greater identity to the polynucleotide sequence selected from the group consisting of SEQ ID NO: 2, 4, 6, 8, 23, 26 and 28. CSSK as encoded by any of the polynucleotides, has fibrinogen-activation activity and fibrin affinity.

The CSSK produced in accordance with the present invention is modified by post-translational modification, such as glycosylation, which makes it more suitable for administration to humans.

Yeast Cells Producing CSSK

Another embodiment of the present invention provides a transformed yeast cell expressing a clot specific streptokinase (CSSK), said CSSK comprising: (a) streptokinase (SK) produced by Streptococcus equisimilis, or a derivative of SK having the ability to activate plasminogen; and (b) fibrin binding domains 4 and 5 (FBD 4,5) of human fibronectin, or a derivative of FBD 4,5 thereof having fibrin affinity.

In another embodiment of the present invention, there is provided a transformed yeast cell expressing a clot specific streptokinase (CSSK), wherein said CSSK comprises: a streptokinase sequence having at least 85% identity to the polypeptide sequence as set forth in SEQ ID NO: 11; and a polypeptide sequence having at least 85% identity to the polypeptide sequence as set forth in SEQ ID NO: 22, at each of the N- and C-termini of the streptokinase sequence.

In yet another embodiment of the present invention, there is provided a transformed yeast cell expressing a clot specific streptokinase (CSSK), wherein said CSSK is encoded by a polynucleotide sequence having at least 85% homology to the polynucleotide sequence selected from the group consisting of SEQ ID NO: 2, SEQ ID NO: 4, SEQ ID NO: 6 and SEQ ID NO: 8.

In yet another embodiment of the present invention, there is provided a transformed yeast cell expressing a clot specific streptokinase (CSSK), wherein said CSSK is encoded by a polynucleotide selected from the group consisting of SEQ ID NO: 2, SEQ ID NO: 4, SEQ ID NO: 6 and SEQ ID NO: 8.

In still another embodiment of the present invention, there is provided a transformed yeast cell expressing a clot specific streptokinase (CSSK), wherein the yeast is methylotrophic yeast selected from the group consisting of Pichia, Hansenula, Torulopsis and Candida species.

In yet another embodiment of the present invention there is provided a transformed yeast cell expressing a clot specific streptokinase (CSSK), wherein the yeast is selected from the group consisting of Pichia pastoris, Pichia methanolica, Pichia anomola, Hansenula polymorpha and Candida boidinii.

In still another embodiment of the present invention, there is provided a transformed yeast cell expressing a clot specific streptokinase (CSSK), wherein the yeast is Pichia pastoris.

In another embodiment of the present invention there is provided a transformed yeast cell expressing a clot specific streptokinase (CSSK), wherein the yeast is Pichia pastoris having accession no. MTCC 25071.

Another embodiment of the present invention provides a transformed yeast cell comprising the expression cassette, wherein the yeast is methylotropic yeast selected from the group consisting of Pichia, Hansenula, Torulopsis and Candida species.

In another embodiment of the present invention, there is provided a transformed yeast cell, wherein the yeast is selected from the group consisting of Pichia pastoris, Pichia methanolica, Pichia anomola, Hansenula polymorpha and Candida boidinii.

In another embodiment of the present invention, there is provided a transformed yeast cell, wherein the yeast is Pichia pastoris having accession no. MTCC 25071. The transformed yeast cell is deposited at an International Microorganism Depository Authority, Microbial Type Culture Collection & Genebank, Institute of Microbial Technology, Sector 39-A, Chandigarh, India. The date of deposit is Oct. 19, 2015.

These transformed yeast strains express high quantities of CSSK. The yeast species useful in the present invention are methylotrophic species, which can grow in media containing methanol or methane as a carbon source. Exemplary methylotrophic yeasts in accordance with the present invention include yeast of the genus Hansenula, Pichia, Candida, or Torulopsis. Preferred species include Pichia pastoris, Pichia methanolica, Pichia anomola, Hansenula polymorpha and Candida boidinii. Most preferred is Pichia pastoris. The auxotrophic mutant strain of P. pastoris His4 (GS115) is particularly preferred.

The yeast species can be transformed by introduction into the yeast cell of a vector encoding CSSK, as further detailed below.

The recombinant yeast secrete CSSK extracellularly, so CSSK can be obtained with mild recovery methods known in the art, such as centrifugation and microfiltration and the like that enable less degradation and higher yield of CSSK.

Nucleic Acids and Vectors for Expression of CSSK in Yeast

Another embodiment of the present invention provides an expression vector for transforming a yeast cell, wherein the expression vector comprises at least one expression cassette of the present invention.

In another embodiment of the present invention, there is provided an expression vector, wherein the expression vector comprises a polynucleotide having at least 80%, 81%, 82%, 83%, 84%, 85%, 86%, 87%, 88%, 89%, 90%, 91%, 92%, 93%, 94%, 95%, 96%, 97%, 98%, or 99% or greater identity to a polynucleotide sequence selected from the group consisting of SEQ ID NO: 2, SEQ ID NO: 4, SEQ ID NO: 6, SEQ ID NO: 8, SEQ ID NO: 23, SEQ ID NO: 26 and SEQ ID NO: 28.

In another embodiment of the present invention, there is provided an expression vector, wherein the expression vector comprises a polynucleotide having at least 85% identity to a polynucleotide sequence selected from the group consisting of SEQ ID NO: 2, SEQ ID NO: 4, SEQ ID NO: 6, SEQ ID NO: 8, SEQ ID NO: 23, SEQ ID NO: 26 and SEQ ID NO: 28.

In another embodiment of the present invention, there is provided an expression vector, wherein the expression vector comprises a polynucleotide sequence selected from the group consisting of SEQ ID NO: 2, SEQ ID NO: 4, SEQ ID NO: 6, SEQ ID NO: 8, SEQ ID NO: 23, SEQ ID NO: 26 and SEQ ID NO: 28.

In another embodiment of the present invention, there is provided an expression vector, wherein the expression vector encodes a polypeptide having at least 80%, 81%, 82%, 83%, 84%, 85%, 86%, 87%, 88%, 89%, 90%, 91%, 92%, 93%, 94%, 95%, 96%, 97%, 98%, or 99% or greater identity to a polypeptide sequence selected from the group consisting of SEQ ID NO: 1, SEQ ID NO: 3, SEQ ID NO: 5, SEQ ID NO: 7, SEQ ID NO: 24, SEQ ID NO: 25, SEQ ID NO: 27 and SEQ ID NO: 29.

In another embodiment of the present invention, there is provided an expression vector, wherein the expression vector encodes a polypeptide having at least 85% identity to a polypeptide sequence selected from the group consisting of SEQ ID NO: 1, SEQ ID NO: 3, SEQ ID NO: 5, SEQ ID NO: 7, SEQ ID NO: 24, SEQ ID NO: 25, SEQ ID NO: 27 and SEQ ID NO: 29.

In another embodiment of the present invention, there is provided an expression vector, wherein the expression vector encodes a polypeptide having a sequence selected from the group consisting of SEQ ID NO: 1, SEQ ID NO: 3, SEQ ID NO: 5, SEQ ID NO: 7, SEQ ID NO: 24, SEQ ID NO: 25, SEQ ID NO: 27 and SEQ ID NO: 29.

Another embodiment of the present invention provides a polynucleotide sequence having at least 80%, 81%, 82%, 83%, 84%, 85%, 86%, 87%, 88%, 89%, 90%, 91%, 92%, 93%, 94%, 95%, 96%, 97%, 98%, or 99% or greater identity to a polynucleotide sequence selected from the group consisting of SEQ ID NO: 4, SEQ ID NO: 6, SEQ ID NO: 8, SEQ ID NO: 23, SEQ ID NO: 26 and SEQ ID NO: 28.

Another embodiment of the present invention provides a polynucleotide having the nucleic acid sequence selected from the group consisting of SEQ ID NO: 4, SEQ ID NO: 6, SEQ ID NO: 8, SEQ ID NO: 23, SEQ ID NO: 26 and SEQ ID NO: 28.

CSSK as encoded by polynucleotide sequences as disclosed herein have fibrinogen-activation activity and fibrin affinity.

Another embodiment of the present invention also provides vectors for transforming yeast cells to express CSSK. Many vectors useful for transferring exogenous genes into target yeast cells are available. The vectors may be episomal, e.g. plasmids, or may be integrated into the target cell genome, through homologous recombination or random integration. In homologous recombination, the gene of interest (herein, the gene encoding CSSK) is targeted to a particular locus in the host cell genome. Any sequence can be designed for homologous recombination with a target locus within a host cell genome by designing the vector carrying the gene of interest to have regions of DNA homologous to the target locus sequence, the homologous regions flanking the 5' and 3' ends of the gene of interest on the vector (Rothstein, R. J. 1983. *Methods Enzymol* 101: 202-211; Cregg J. M. et al. 1987, *Nature Biotechnology* 5:479-485). A region of homologous sequence designed for integration of a gene of interest into a target locus by homologous recombination with a host cell genome is referred herein as an "integration sequence". Once the vector is introduced into the yeast cell, the regions of the vector with sequence homology to the target locus will align with the target locus and the gene of interest will integrate into the target locus.

The disclosed vectors in accordance with the present invention encode CSSK in operable linkage to a suitable promoter for expression in yeast. The phrase "operably linked" or "under transcriptional control" as used herein means that the promoter is in the correct location and orientation in relation to a polynucleotide to control the initiation of transcription by RNA polymerase and expression of the polynucleotide. Yeast promoters include inducible promoters, such as methanol-inducible promoters, and constitutive promoters, such as the general amino acid permease-1 (GAP-1) promoter. Examples of methanol-inducible promoters include alcohol oxidase I (AOX1) and alcohol oxidase II (AOX2) gene promoters.

In an embodiment of the present invention, an expression cassette has been constructed containing the following DNA sequences in the 5'-3' direction of the transcription reading frame: (a) a yeast methanol-inducible promoter sequence; (b) an *S. cerevisiae* signal sequence for secretion of CSSK from the cell; (c) the polypeptide corresponding to the clot-specific streptokinase; and (d) a transcription termination sequence functional in methylotrophic yeast. The DNA sequences are functionally associated with one another in order to carry out the transcription of the sequences encoding the polypeptide of (c).

Vectors useful in the present invention can include a selection marker gene for selection of yeast transformants. To this purpose, any functional selection marker gene from methylotrophic yeast can be used that confers a different phenotype on a methylotrophic yeast cell and therefore permits it to be identified and grown in a selective way different from the majority of non-transformed cells. Appropriate selection marker genes include, for example, selection marker systems composed of an auxotrophic mutant of *P. pastoris* strains and a wild type biosynthetic gene that complements the defect in the host cells. For example, for the transformation of *P. pastoris* His4-strains, the HIS gene of *S. cerevisiae* or *P. pastoris* can be used.

A vector may further include one or more selection marker genes that are functional in bacteria. Any gene that confers a phenotype in bacteria for the purposes of identification and selective cultivation is suitable. This additional selection marker permits the vector of the application to be introduced into bacteria, such as *E. coli*, for amplification. Appropriate selection marker genes include: the ampicillin (Amp$^r$) resistance gene, the tetracycline (Tc$^r$), the kanamycin (Kan$^r$) resistance gene, and the like.

In an embodiment of the present invention, the heterologous protein expression system used for the expression of CSSK cDNA uses the promoter derived from *P. pastoris* AOX1 methanol inducible gene, which is very efficiently expressed and accurately regulated. In a specific example, the vector has the *P. pastoris* AOX1 promoter; the DNA sequence encoding an alpha mating factor signal sequence; the sequence encoding CSSK; and a transcription terminator derived from *P. pastoris* AOX1 gene.

The vector can have a signal sequence for secretion of CSSK from the cell. A "signal sequence" as disclosed herein is a sequence (also known as a "tag") that directs the expressed protein to the cell surface for release/secretion of the protein to the extracellular environment. Examples of signal sequences include the alpha mating factor signal sequence from *Saccharomyces cerevisiae*, the alpha amylase signal sequence, the inulase signal sequence, the killer protein signal sequence, the lysozyme signal sequence, the albumin signal sequence, and the glucoamylase signal sequence. In accordance with the present invention, the nucleic acid sequence of the native alpha factor signal sequence of *Saccharomyces cerevisiae* is as set forth in SEQ ID NO: 15. The amino acid sequence of the native alpha factor signal sequence of *Saccharomyces cerevisiae* is as set forth in SEQ ID NO: 14.

In another embodiment of the present invention, the vector can encode a "modified" alpha signal sequence. The modification involves removal of the STE13 protease cleavage site from the 'native' alpha mating factor signal sequence in the recombinant vector. In the 'native' alpha mating factor signal sequence, KEX2 and STE13 cleavage sites reside near the C-terminal end of signal peptide sequence.

The KEX2 cleavage site occurs between arginine and glutamate in the signal peptide sequence stretch of Glu-Lys-Arg-Glu-Ala-Glu-Ala (SEQ ID NO: 16). The Glu-Ala repeats are further cleaved by the STE13 gene product. However, the Glu-Ala repeats are not necessary for the cleavage of KEX2, depending on the amino acid following the Glu-Lys-Arg peptide sequences. In some cases, where STE13 cleavage is not efficient, the Glu-Ala repeats are retained at the $NH_2$-terminus of expressed protein of interest. Therefore, removal of the STE13 cleavage site of the alpha factor signal sequence can provide improved proteolytic processing of the signal sequence, which in turn produces CSSK without unwanted N-terminal amino acid residues. In accordance with the present invention, polynucleotide encoding a modified alpha signal sequence is a polunucleotide sequence having at least 85%, 86%, 87%, 88%, 89%, 90%, 91%, 92%, 93%, 94%, 95%, 96%, 97%, 98%, or 99% or greater identity to SEQ ID NO: 9. In accordance with the present invention, polynucleotide encoding a modified alpha signal sequence is as set forth in SEQ ID NO: 9. In accordance with the present invention, the vector disclosed in the present invention has a methylotrophic yeast gene promoter, a modified alpha signal sequence, apolynucletide sequence encoding CSSK and a transcription terminator functional in methylotrophic yeasts.

In accordance with the present invention, the vector can have a polynucleotide sequence encoding CSSK with a codon adaptation index of greater than 0.80, 0.81, 0.82, 0.83, 0.84, 0.85, 0.86, 0.87, 0.88, 0.89, 0.90, 0.91, 0.92, 0.93, 0.94, or 0.95 for the yeast species expressing the CSSK.

An embodiment of the present invention provides a clot specific streptokinase produced by the transformed yeast cell, wherein the clot specific streptokinase is glycosylated and has a molecular weight of 80,515 Da.

Transformation of Yeast to Generate CSSK-Expressing Strains

The vectors disclosed herein are used to transform methylotrophic yeast cells for expression and secretion of CSSK. Transformation occurs via vector elements (also referred to herein as "expression cassettes") with the CSSK gene and an integration sequence upstream and/or downstream of the CSSK gene for homologous recombination in the yeast genome. The plasmid that can be linearized to facilitate integration and the DNA fragment/expression cassette will integrate into the host chromosome by means of the integration sequence or sequences. In one example, integration occurs by at least one crossover recombination at the AOX1 locus.

Methods for introducing vectors into methylotrophic yeast include the spheroplast technique (Cregg J M et al. 1985. *Mol Cell Biol* 5: 3376-3385), electroporation (Simon, J. R. & McEntee, K. 1989. *Biochem Biophys Res Commun* 164: 1157-1164), and lithium chloride transformation (Ito, H et al. 1983. *J Bacteriol* 153:163-168). In one embodiment, electroporation methods are used. Applicable methods for the cultivation of methylotrophic yeast cells are known in the art.

In one embodiment of the present invention, the host yeast cell is transformed with a linear DNA fragment containing the cDNA encoding CSSK, under the regulation of a *P. pastoris* promoter gene, and the expression cassette is integrated into the host genome by homologous recombination.

For the development of *P. pastoris* Mut strains (Mut refers to the phenotype that utilizes methanol), the vector can be integrated into a suitable locus, such as the AOX1 locus. In one example, as a result of integration into the AOX1 locus, $Mut^S$ strains can be obtained. In $Mut^S$ strains, the AOX1 gene is replaced by the expression cassette and therefore the ability to use methanol in this strain is decreased. Loss of the AOX1 gene, and thus a loss of most of the cells alcohol oxidase activity, results in a strain that is phenotypically $Mut^S$ (Methanol utilization slow). This results in a reduction in the cells' ability to metabolize methanol. The cells, therefore, exhibit poor growth on methanol medium. A slow speed of growth is maintained with methanol due to the expression of the AOX2 gene product. The transformed cells that have integrated the expression cassette into the AOX1 locus (through site-directed recombination) can be identified by the presence of the marker gene on the expression cassette. Selected cells can be screened for their $Mut^S$ genotype by growing them in presence of methanol and recording the speed of growth, or by using PCR to confirm the presence of the expression cassette.

Methods of Screening Yeast for CSSK Producing Clones

Another embodiment of the present invention provides a method of screening a yeast cell to identify a transformed yeast cell producing clot specific streptokinase, said method comprising:
(a) transforming at least one yeast cell with a vector of the present invention to obtain a transformed yeast cell;
(b) culturing at least one transformed yeast cell in BMMY culture medium with methanol to induce expression of CSSK protein;
(c) separating the culture medium from the transformed yeast cell to obtain a supernatant;
(d) testing the supernatant for plasminogen activation; and
(e) identifying a transformed yeast cell producing clot specific streptokinase by detecting plasminogen activation in the supernatant of the cell.

In an embodiment of the present invention there is provided a method of screening a yeast cell to identify a transformed yeast cell producing clot specific streptokinase, wherein the plasminogen activation testing in step (d) is done by combining the supernatant with plasminogen and a chromophore and a change in light absorbance is detected at 405 nm.

In another embodiment of the present invention there is provided a method of screening a yeast cell to identify a transformed yeast cell producing clot specific streptokinase, wherein the plasminogen activation is measured against a reference value representing a known quantity of CSSK.

In another embodiment of the present invention there is provided a method of screening a yeast cell to identify a transformed yeast cell producing clot specific streptokinase further comprises confirming CSSK production in the cell identified in step (e) by SDS-PAGE analysis.

The present invention also discloses a plate-based screening methodology for clot specific streptokinase (CSSK) and its variants that enables faster selection of best producing clones. With the help of this plate based methodology, different important culture parameter can be modified at small scale.

The plate-based screening methodology for screening transformed yeast cells can identify a yeast cell producing clot specific streptokinase (CSSK). The methods include the steps of: (a) transforming at least one yeast cell with a vector encoding a CSSK as disclosed herein; (b) culturing said yeast cell with methanol to induce expression of CSSK protein; (c) testing the supernatant of said cultured cell for plasminogen activation; and (d) identifying a CSSK-producing yeast cell or cells by detecting plasminogen activation in the supernatant of the cell Upon transformation of a *P. pastoris* host strain by an expression vector carrying the gene of interest, individual transformants typically express widely varying amounts of protein. Thus many rounds of diagnosis and screening transformants are required to get a hyper-producing clone. Positive transformed cells can be characterized by methods known in the art, such as polymerase chain reaction (PCR), Southern blot, or Northern blot, but depending upon the polypeptide composition and post-translational modification, the protein levels are not always in consonance with the transcription level. Therefore, the present application provides methods to check protein levels directly by a plate based activity assay that enables screening of all obtained transformants quickly and efficiently.

The disclosed plate based screening method was created to select the best clones without time consuming steps of concentration and multiple SDS-PAGE analysis of samples. Moreover, said method allows screening of large numbers of obtained transformants, thus minimizing the chances of missing the rare best ones.

Transformed strains that possess the phenotype or desired genotype are grown in shake-flask for confirmation of selected clones by plate based screening methodology. Selected clones are tested for methanol-induced CSSK expression at different culture conditions, for example, temperature, pH, methanol concentration and harvest days. Fermentation strategy is utilized by preferred standard protocol but systematically modified for best culture conditions to get pronounced yield of the CSSK protein in biologically active form.

Transformed methylotrophic yeasts that are identified by desired genotype and phenotype are grown in a fermentor. The levels of CSSK secreted into the culture medium can be determined by plasminogen activation assay, SDS-PAGE, Western-blot analysis using anti-SK or fibronectin anti-sera and in parallel with *E. coli* expressed and purified SK or CSSK standards.

Plasminogen activation can be tested by combining the supernatant with plasminogen and a chromophore, and detecting plasminogen activation by detecting a change in light absorbance. In another example, plasminogen activation is measured against a reference value representing a known quantity of CSSK. CSSK production in the cell or cells can be optionally confirmed by SDS-PAGE analysis.

Compositions

An embodiment of the present invention provides pharmaceutical composition comprising CSSK produced by the methods disclosed herein. Such compositions are useful for treating circulatory conditions including, but not limited to, myocardial infarction, vascular thromboses, pulmonary embolism, stroke a vascular event, including acute ischemic stroke, angina, pulmonary embolism, transient ischemic attack, deep vein thrombosis, thrombotic re-occlusion subsequent to a coronary intervention procedure, peripheral vascular thrombosis, heart failure, Syndrome X and a disorder in which a narrowing of at least one coronary artery occurs.

The compositions comprise an effective amount of CSSK in a pharmaceutically acceptable carrier. As used herein, the phrase "pharmaceutically acceptable" means the carrier, or vehicle, which does not cause an adverse reaction when administered to a mammal. Such carriers are non-toxic and do not create an inflammatory or allergic response in the body. Pharmaceutically acceptable carriers for practicing the present invention include well known components such as, for example, phosphate buffered saline. Additional pharmaceutically acceptable carriers and their formulations are well-known and generally described in, for example, Remington's Pharmaceutical Science (18th Ed., ed. Gennaro, Mack Publishing Co., Easton, Pa., 1990) and the Handbook of Pharmaceutical Excipients (4th ed., Ed. Rowe et al. Pharmaceutical Press, Washington, D.C.), each of which is incorporated by reference.

Examples of compositions comprising the therapeutic amount of CSSK include liquid preparations for parenteral, subcutaneous, intradermal, intramuscular, intracoronarial, intramyocardial or intravenous administration (e.g., injectable administration), such as sterile suspensions or emulsions. Such compositions may be an admixture with a suitable carrier, diluent, or excipient such as sterile water, physiological saline, glucose or the like. The compositions can also be lyophilized.

The compositions can contain auxiliary substances such as wetting or emulsifying agents, pH buffering agents, gelling or viscosity enhancing additives, preservatives, flavoring agents, colors, and the like, depending upon the route of administration and the preparation desired. For example, a lyophilized composition can contain one, two, three, or four or more auxiliary substances such as gelatin polypeptides, cross-linked gelatin polypeptides, glutamate, sodium L-glutamate, and human albumin.

CSSK may be packaged in units of fibrinolytic activity, for example, in a vial ranging from about 1,000,000 to about 2,000,000 International Units (IU) of fibrinolytic activity per vial, or, or from about 1,250,000 to about 1,750,000 IU of fibrinolytic activity per vial, or about 1,500,000 IU of fibrinolytic activity per vial. Methods of determining International Units of fibrinolytic activity are known in the art, for example, in streptokinase formulations which are commercially available, such as STREPTASE (CSL Behring, Canada). In a further example, lyophilized CSSK can be contained in a vial or other container ranging from about 1,000,000 to about 2,000,000 International Units (IU) of fibrinolytic activity per vial; with cross-linked gelatin polypeptides ranging from about 10 to about 40 mg, or about 20 to about 30 mg, or about 25 mg per vial; sodium L-glutamate at about 10 to about 40 mg, or about 20 to about 30 mg, or about 25 mg per vial; and human albumin from about 10 to about 200 mg, or about 50 to about 150 mg, or about 100 mg per vial. The composition can be prepared for intravenous and/or intracoronary administration by adding an appropriate volume of excipient.

Methods of Treatment

CSSK produced as described herein is a thrombolytic drug. Thus, CSSK produced in accordance with the present invention can be used in conditions associated with thrombosis. A composition comprising CSSK can be used to treat or prevent circulatory conditions including, but not limited to, myocardial infarction, vascular thromboses, pulmonary embolism, stroke, including acute ischemic stroke, angina, pulmonary embolism, transient ischemic attack, deep vein thrombosis, thrombotic re-occlusion subsequent to a coronary intervention procedure, peripheral vascular thrombosis, heart failure, Syndrome X and a narrowing of at least one coronary artery.

The CSSK dissolves the blood clot. In an embodiment, the present disclosure relates to a method of site-directed dissolution of a blood clot by administering a therapeutic effective amount of the CSSK produced as described herein to a patient in need of such treatment The terms "treat", "treatment", "treating", and the like, as used herein include amelioration or elimination of a disease or condition, or alleviation of one or more symptoms associated with such disease or condition. As used herein these terms also encompass, depending on the condition of the patient, ameliorating the disease or condition or of symptoms associated with a disease or condition, including reducing the severity of a disease or condition or symptoms associated therewith. As used herein, the terms "therapeutically effective amount" and "effective amount" are used interchangeably to refer to an amount of a composition of the application that is sufficient to prevent or inhibit the development, recurrence, or onset of a circulatory condition as described above, to reduce the severity and duration of a circulatory condition, ameliorate one or more symptoms a circulatory condition, prevent the advancement of a circulatory condition, and/or enhance or improve the therapeutic effect(s) of other treatment(s) for circulatory conditions.

A therapeutically effective amount can be administered to a patient in one or more doses sufficient to palliate, ameliorate, stabilize, reverse or slow the progression of the disease, or otherwise reduce the pathological consequences of the disease, or reduce the symptoms of the disease. The amelioration or reduction need not be permanent, but may be for a period of time ranging from at least one hour, at least one day, or at least one week or more. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition, as well as the route of administration, dosage form and regimen and the desired result.

As used herein the term "prevention" or "prophylaxis" refers to reducing the tendency or probability of being afflicted with a disease or condition or of symptoms associated with a disease or condition, especially those prone to being afflicted with said disease or condition. prior to affliction with said disease or condition. Such prevention or reduction prior to affliction refers to administration of CSSK to a patient that is not at the time of administration afflicted with the disease or condition. "Preventing" also encompasses preventing the recurrence or relapse-prevention of a disease or condition or of symptoms associated therewith, for instance after a period of improvement.

An embodiment of the present invention provides a method of treating or preventing a disease selected from the group consisting of myocardial infarction, vascular thromboses, pulmonary embolism, stroke, acute ischemic stroke, angina, pulmonary embolism, transient ischemic attack, deep vein thrombosis, thrombotic re-occlusion subsequent to a coronary intervention procedure, peripheral vascular thrombosis, heart failure, Syndrome X and a narrowing of at least one coronary artery in a subject in need thereof, comprising administering to the subject by way of injection or infusion a therapeutically effective amount of the composition comprising clot specific streptokinase and pharmaceutically acceptable carrier.

Compositions can be administered in dosages and by techniques well known to those skilled in the medical and veterinary arts taking into consideration such factors as the age, sex, weight, and condition of the particular patient, and the composition form used for administration (e.g., liquid). Dosages for humans or other mammals can be determined without undue experimentation by the skilled artisan, from this disclosure, the documents cited herein, and the knowledge in the art.

In an embodiment, method of treatment include intravenous administration, as an infusion (for example, i.v. administration from about 10 minutes to about 2 hours, or about 10 to about 90 minutes, or about 20 to about 80 minutes, or about 30 to about 60 minutes) or slow bolus injection (a filled syringe administered over about 3 minutes or less, or about 5 minutes or less, or about 10 minutes or less, or about 15 minutes or less). In an embodiment, the treatment method is a bolus intravenous injection at a rate of about 1, or about 2, or about 3, or about 4 ml/min. A dosage (in mg/kg) of about 0.1 to about 1.9, or, about 0.3 to about 1.1, is contemplated per administration, in a total volume of about 1 to about 4 ml liquid. The dose may be repeated about every 30 to about 90 minutes, or about every 1, 2, 3, 4, 8, 12, or 24 hours, at the discretion of the treating physician.

When administered in liquid form, the CSSK is dissolved in saline solution, sugar solution, such as dextrose, or other physiologically acceptable vehicle, such as a vehicle which is isotonic and has a pH ranging from about 6.5 to about 7.5, e.g., neutral pH. In an embodiment, the CSSK is formulated about 0.9% (w/w) saline solution or about 5% (w/w) dextrose solution or other physiologically acceptable vehicle which is isotonic and within the aforementioned pH range. In another embodiment, CSSK produced and purified from a yeast cell, such as *Pichia pastoris*, contains fiber binding domains 4 and 5 of human fibronectin (FBD 4, 5) or derivative or FBD 4,5 thereof having fibrin affinity attached to each end of the streptokinase. The fibrin binding domains mask the ability of the streptokinase component to interact with blood plasminogen. The CSSK thus remains inactive in the blood circulation and does not convert blood plasminogen into plasmin until the fibrin binding domains are cleaved by clot-bound plasmin. This is in contrast to native streptokinase which indiscriminately converts plasminogen into plasmins; CCSK thus prepared is capable of lysing human blood clots without reducing residual plasma fibrinogen levels.

The present disclosure is further illustrated by the following non-limiting examples.

EXAMPLES

Example 1. Construction of Clot-Specific Streptokinase Genetic Vector for *Pichia* Expression Construction of expression vectors as disclosed in the following examples was carried out according to standard methods as described, for example, by J. Sambrook, E. F. Fritsch and T. Maniatis (Molecular cloning: A laboratory Manual, second edition (1989), Cold Spring Harbor Laboratory Press, Cold Spring Harbor, N.Y., USA).

Figure 1B:
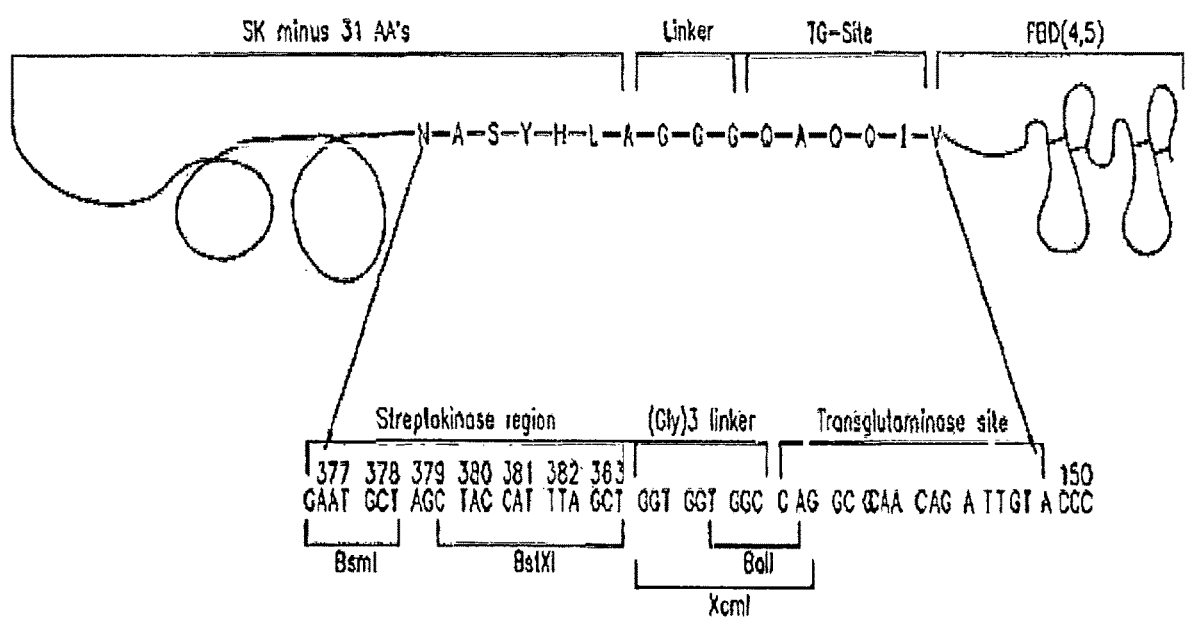
FIG. 1B: Schematic diagram of a fragment of the CSSK gene showing SK connected to the fibrin binding domain via a poly-glycine linker and transglutaminase region. SEQ ID NO: 12 is the amino acid sequence; SEQ ID NO: 13 is the nucleic acid sequence.

The gene encoding clot-specific streptokinase (CSSK) was developed by adding fibrin binding domains 4 and 5 ("FBD(4,5)") from human fibronectin protein onto the streptokinase (SK) gene, with copies of the 4 and 5 domains placed at the N-terminal and also the C-terminal of the streptokinase gene (FIG. 1A). The DNA sequences of SK gene from *Streptococcus equisimilis* H46A, and fibrin binding domains 4 and 5 from human fibronectin, and methods to produce CSSK are disclosed in U.S. Pat. Nos. 7,163,817 and 8,143,027, the contents of each of which are incorporated in their entirety by reference herein. This CSSK has a poly-gly linker and transglutaminase site linking the C-terminal end of SK to the FBD(4,5) domain adjacent to the SK C-terminus (FIG. 1B). CSSK as utilized in the examples herein is streptokinase with FBD 4,5 domains at both N-terminal and C-terminal ends of SK, e.g., FBD(4,5)-SK-FBD(4,5).

Figure 2:
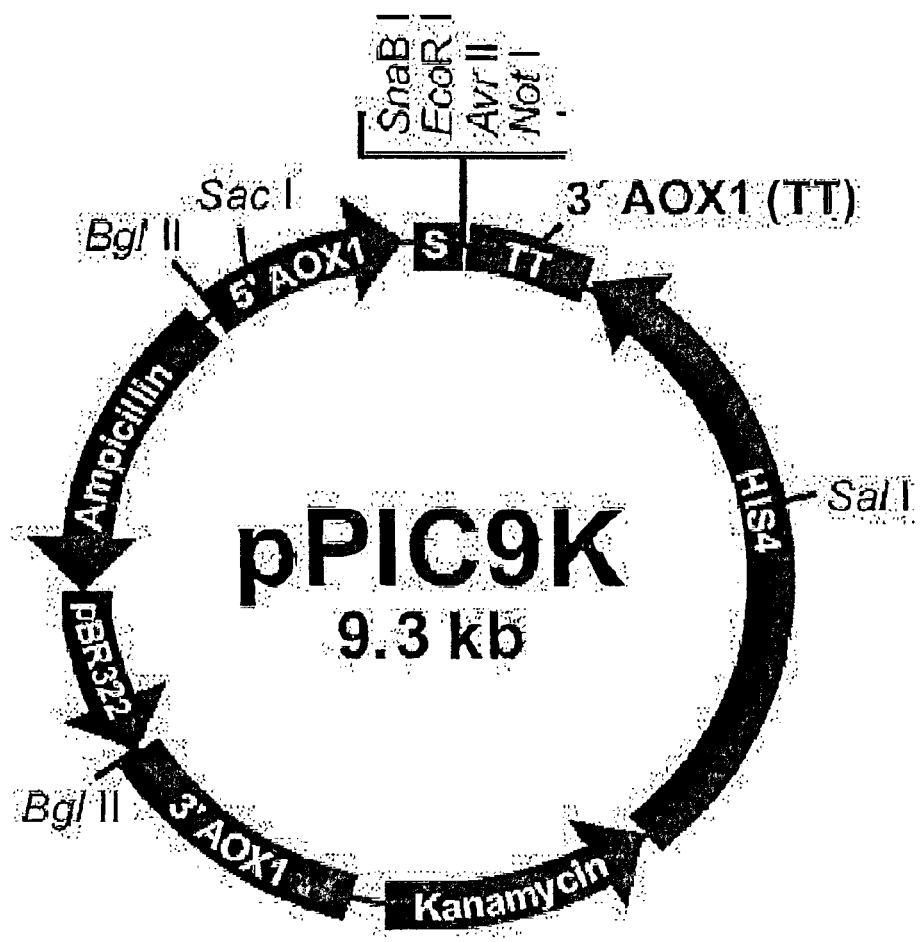
FIG. 2: The pPIC9K vector map. CSSK was cloned into the multi-cloning site in-frame with the alpha mating factor signal sequence indicated as "S" in the vector map.

An expression vector was constructed with the native *Pichia* alpha mating signal sequence preceding the CSSK gene. The CSSK sequence was subcloned from a pET23d vector containing CSSK [pET23(d)FBD(4,5)-SK-FBD(4,5)], as disclosed in U.S. Pat. No. 8,143,027, into the *Pichia* expression vector pPIC9K (Invitrogen/Life Technologies). The pPIC9K vector (FIG. 2) has a 5' AOX1 (alcohol oxidase-1) promoter for methanol-induction, the promoter sequence having a 5' AOX1 primer site; a *Pichia* α-factor secretion signal for secretion of expressed polypeptides from the host cell, the secretion signal sequence having an α-factor primer site; a multiple cloning site (MCS); a 3' AOX1 primer site; a 3' AOX1 transcription termination (TT) region; a histidine-4 (HIS4) open reading frame (ORF); a Kanamycin resistance gene; a 3' AOX1 fragment; a pBR322 origin for replication in *E. coli*; and an ampicillin resistance gene.

The pPIC9K vector has a bacterial origin of replication but no yeast origin of replication. Stable transformants can only result if recombination events occur between the plasmid and the *Pichia* genome. The α-factor secretion signal causes the secretion of recombinant protein into the medium. The MCS has four unique restriction sites that can be employed for in frame cloning of the target gene with the alpha-mating signal sequence. The HIS4 ORF allows the selection of transformants on plates without histidine (the wild host GS115 is his4 and hence requires histidine for growth). If linearized with Sac I and Sal I, transformation results in the generation of His+ Mut+ cells in GS115 after recombination, while if linearized with Bgl II, it results in the generation of His+ and Mut$^s$ cells.

Figure 1C:
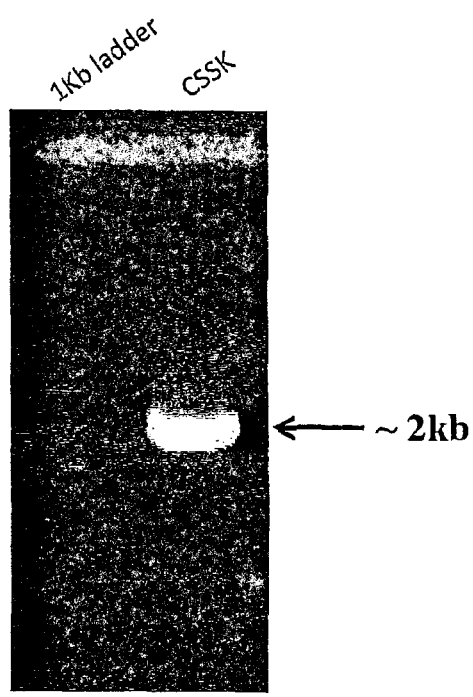
FIG. 1C: Agarose gel (0.8%) showing PCR amplifications of CSSK. The PCR products of 1860 bp were successfully amplified.

For subcloning, pET23(d)FBD(4,5)-SK-FBD(4,5) was cleaved with the restriction enzymes EcoRI and NotI and digested product was resolved on a 0.8% agarose gel. The fragment corresponding to CSSK (1860 bp) (FIG. 1C) was eluted from the gel using the QIAQUICK Gel Extraction kit (Qiagen Sciences), according to manufacturer's specification. The eluted fragment was digested with EcoRI and NotI restriction enzymes and ligated into EcoRI- and Not1-digested pPIC9K vector. The shuttle vector was introduced into *E. coli* XL1-BL by heat shock transformation methodology. The resulting vector, called pPIC9K-CSSK, was digested with the EcoRI and NotI enzymes. The alignment and sequence were confirmed by amplification and sequencing using the 5'AOX1 forward primer sequence (SEQ ID NO: 30; 5'-GACTGGTTCCAATTGACAAGC-3') and 3'AOX1 reverse primer (SEQ ID NO: 31; 5'-GCAAATGG-CATTCTGACATCC-3')

The polypeptide sequence of CSSK is is as set forth in SEQ ID NO. 1. The polynucleotide sequence encoding the CSSK is as set forth in SEQ ID NO. 2.

Example 2. Construction of a *Pichia* CSSK Expression Vector Comprising a Modified Alpha Signal Sequence In the α-factor signal polynucleotide sequence (SEQ ID NO: 15) of the pPIC9K vector, initial cleavage of the signal polypeptide sequence occurs by the action of the KEX2 protein. KEX2 cleavage occurs between arginine and glutamate in the polypeptide sequence Glu-Lys-Arg-Glu-Ala-Glu-Ala (SEQ ID NO: 16). The Glu-Ala repeats are subsequently cleaved by the STE13 protein. However, the Glu-Ala repeats are not necessary for cleavage by KEX2, as KEX2 will recognize and cleave other sequences depending on the amino acid following the Glu-Lys-Arg sequences. As a point of concern, STE13 cleavage can be incomplete, leading to retention of Glu-Ala repeats on the $NH_2$-terminus of expressed protein of interest and inefficient secretion of heterologous protein in extracellular medium.

Figure 4:
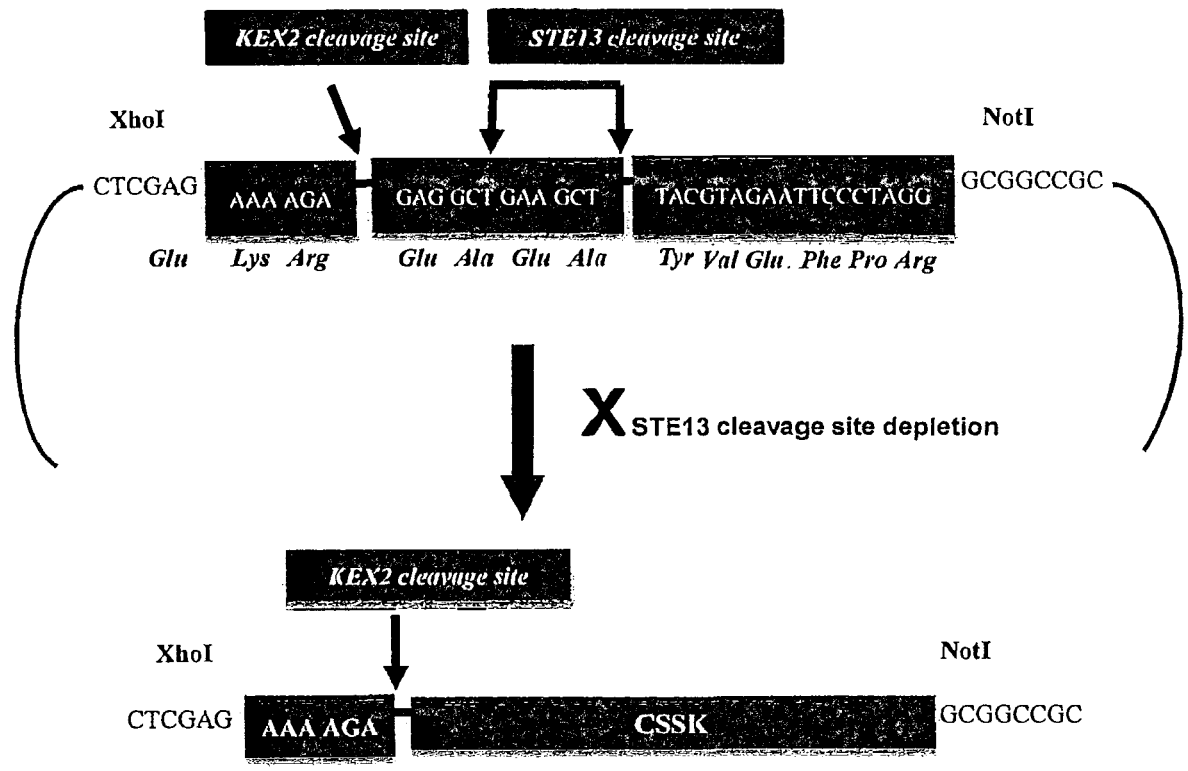
FIG. 4: Strategy for the removal of the STE13 cleavage site from the native alpha mating factor signal sequence. The alpha mating factor signal sequence stretch with KEX2 and STE13 signal cleavage sites (nucleic acid sequence, SEQ ID NO: 18; amino acid sequence, SEQ ID NO: 19) was removed from the pPIC9K vector after digestion with XhoI and NotI. The forward primer for the amplification of CSSK was integrated with XhoI site (CTCGAG) adjacent to the KEX2 cleavage site (AAAAGA) so as to obtain the pPIC9K-alpha modified CSSK expression vector without a STE13 cleavage site, creating the 'modified' alpha mating factor signal sequence. NotI site (GCGGCCGC) was moved from end of signal sequence to end of CSSK.

CSSK was expressed from the pPIC9K-CSSK vector at low levels. In addition, the CSSK N-terminus was subject to GLU-ALA amino acid additions, apparently resulting from incomplete or inefficient STE13 cleavage. Efficient proteolytic processing of the signal sequence promotes the secretion of expressed heterologous protein into the extracellular milieu. Therefore, a modified alpha signal sequence was designed by deleting the STE13 protease cleavage site (FIGS. 3-4). FIG. 4 shows the strategy for the removal of the STE13 cleavage site from the native alpha mating factor signal sequence. The alpha mating factor signal sequence stretch with KEX2 and STE13 signal cleavage sites (polynucleotide sequence as set forth in SEQ ID NO: 18 and polypeptide sequence as set forth in SEQ ID NO: 19) was removed from the pPIC9K vector after digestion with XhoI and NotI. The forward primer is as set forth in SEQ ID NO: 32 (GACAGC<u>CTCGAG</u>AAAAGAGTGCAAGCTCAACAA). [XhoI restriction site is underlined. And KEX2 cleavage site (AAAAGA) is italicized], which is used for the amplification of CSSK was integrated with XhoI site (CTCGAG) adjacent to the KEX2 cleavage site (AAAAGA) so as to obtain the pPIC9K-alpha modified CSSK expression vector without a STE13 cleavage site, creating the 'modified' alpha mating factor signal sequence. NotI site (GCGGCCGC) was moved from end of signal sequence to end of CSSK.

The polypeptide sequence of the modified alpha signal is set forth in SEQ ID NO: 9 and the polynucleotide sequence of modified alpha signal is as set forth in SEQ ID NO: 10.

Figure 5:
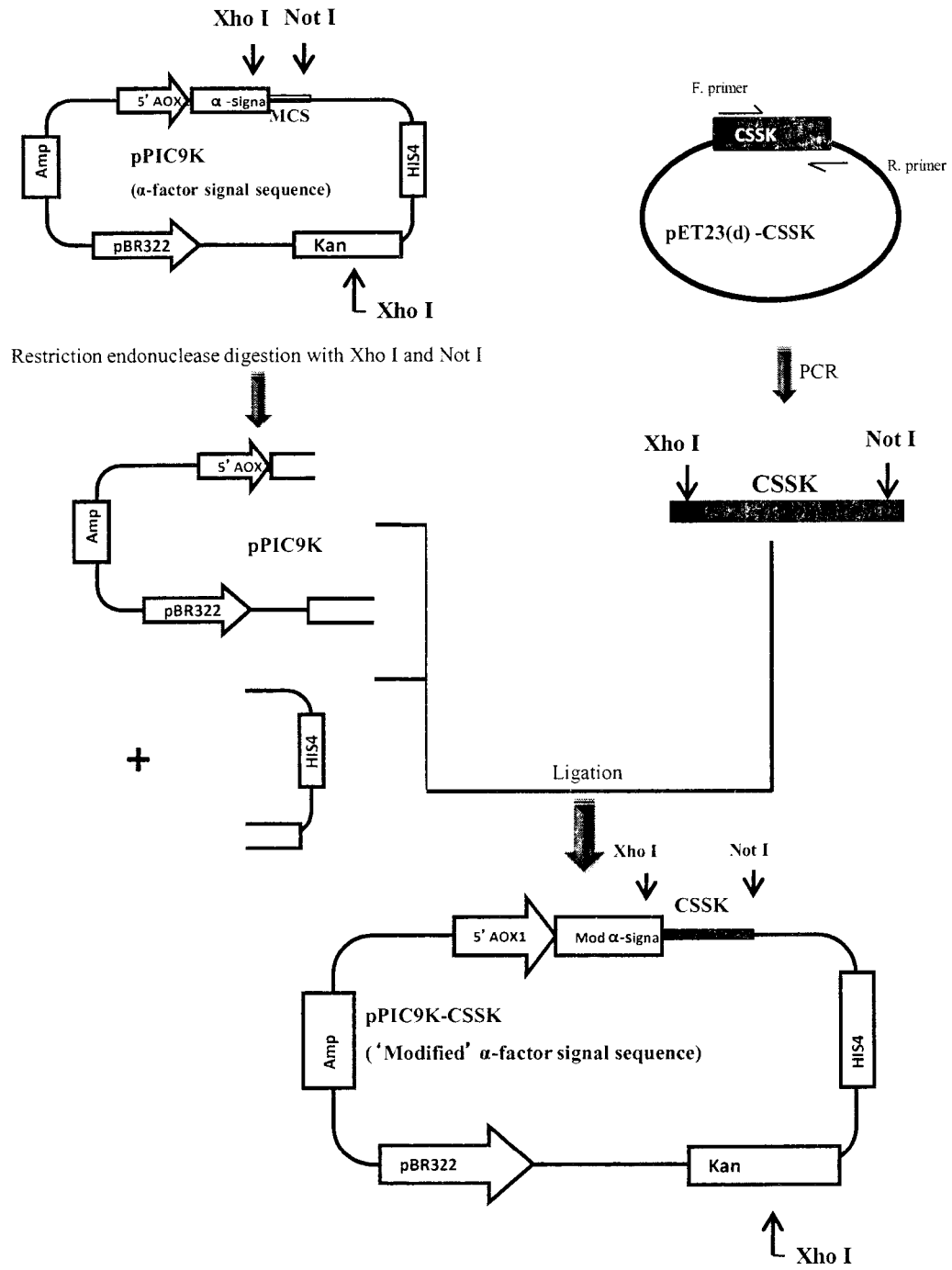
FIG. 5: Schematic representation of construction of the recombinant pPIC9K-alpha modified CSSK plasmid with 'modified' α-factor signal sequence. The CSSK sequence was amplified from pET23(d)-CSSK utilizing primers which incorporated an XhoI restriction site, a KEX2 cleavage site at 5' end, and a NotI restriction site at the 3' end, respectively, followed by double-digestion of the CSSK PCR products with Xho I and Not I enzymes. The pPIC9K vector was also digested with XhoI and NotI, which resulted in cleavage of the STE13 site along with generation of two fragments of pPIC9K vector due to the presence of two XhoI sites in the vector. Subsequently, three-piece ligation of XhoI and NotI digested fragments of the pPIC9K vector (two fragments) and CSSK led to the formation of a recombinant pPIC9K-CSSK plasmid with a 'modified' α-factor signal sequence, devoid of the STE13 cleavage site.
Figure 7:
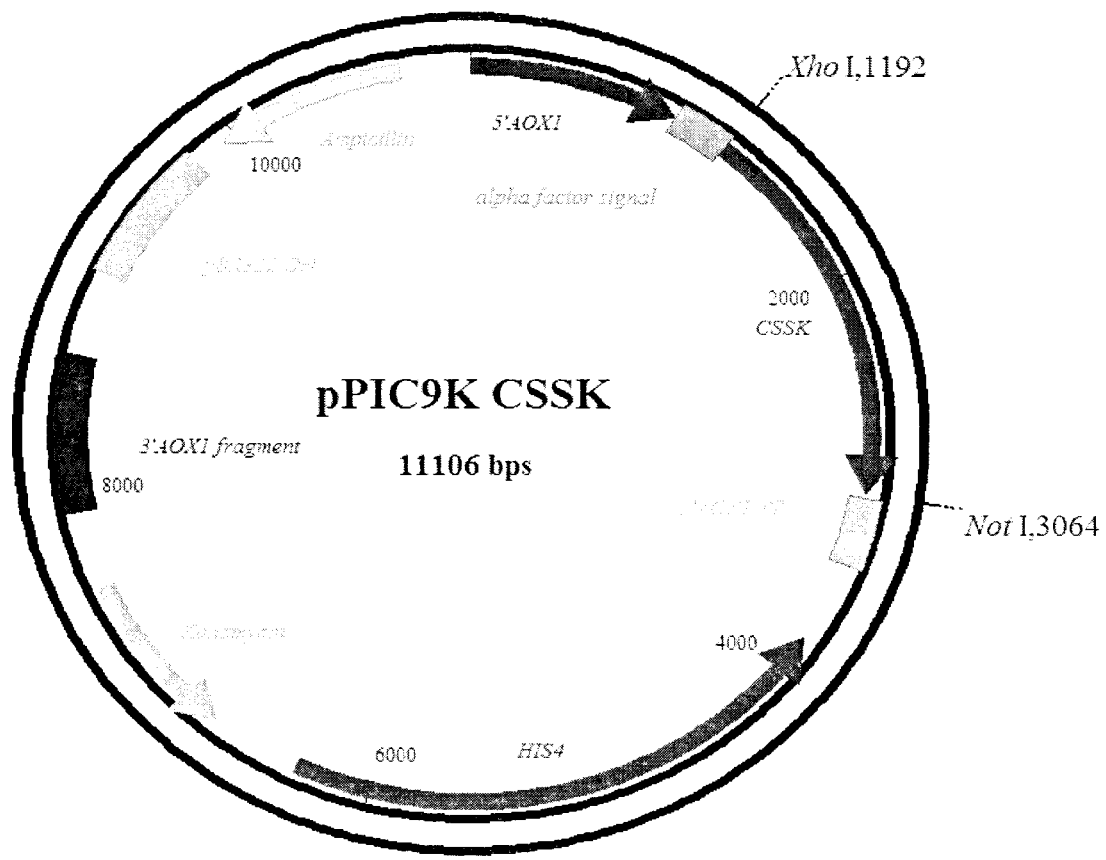
FIG. 7: Vector map of the recombinant expression plasmid pPIC9K with alpha modified CSSK. 5'AOX1 promoter fragment: bases 1-948; allows methanol-inducible high level expression in *Pichia* and also targets plasmid integration to the AOX1 locus. Alpha factor secretion signal: bases 949-1203; allows secretion of desired protein into the medium. CSSK gene: bases 1204-3063. 3' AOX1 transcription termination (TT): bases 3083-3416; permits efficient transcription termination and polyadenylation of the mRNA. HIS4 ORF: bases 3810-6344; provides a selectable marker to isolate *Pichia* recombinant strains. Kanamycin resistance gene: bases 6758-7573; allows selection for kanamycin resistance in *E. coli* and also allows in vivo screening for multicopy inserts by increased resistance to G418. 3'AOX1 fragment: bases 7952-8709; targets plasmid integration at the AOX1 gene. pBR322 origin: bases 9118-9791; allows replication in *E. coli*. Ampicillin resistance gene: bases 9936-10796; allows selection for ampicillin resistance in *E. coli*.
Figure 8:
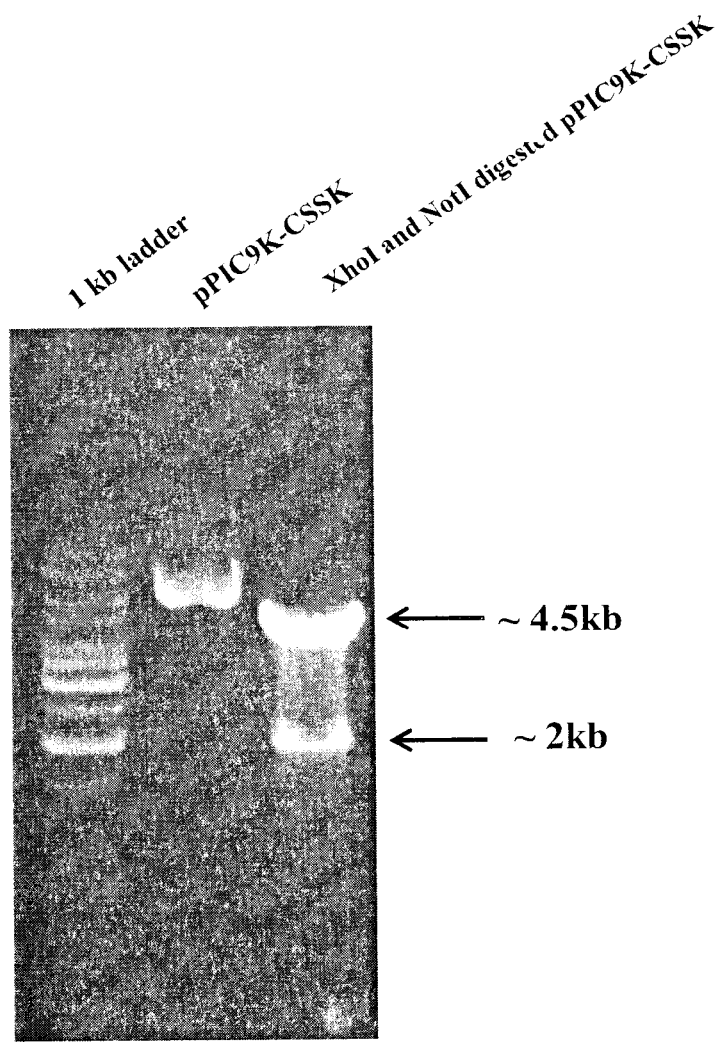
FIG. 8: Agarose gel (0.8%) electropherogram showing the restriction endonuclease digestion of recombinant pPIC9K-alpha modified CSSK plasmid with XhoI and NotI. 1860 bp DNA fragments following double digestion of recombinant pPIC9K-alpha modified CSSK plasmid indicate successful cloning of CSSK in pPIC9K vector containing alpha modified signal sequence.

The polynucleotide sequence of CSSK with the modified alpha signal polypeptide sequence (SEQ ID NO: 26) was cloned into pPIC9K. The CSSK polynucleotide sequence was amplified from pET23(d)-CSSK utilizing primer as set forth in SEQ ID NO: 33 (GACAGC<u>CTCGAG</u>AAAAGAGTGCAAGCTCAACAA) [XhoI restriction site is underlined], which incorporated an XhoI restriction site, a KEX2 cleavage site at 5' end, and a NotI restriction site at the 3' end, respectively, followed by double-digestion of the CSSK PCR products with Xho I and Not I enzymes. The pPIC9K vector was also digested with XhoI and NotI, which resulted in cleavage of the STE13 site along with generation of two fragments of pPIC9K vector due to the presence of two XhoI sites in the vector. Subsequently, three-piece ligation of XhoI and NotI digested fragments of the pPIC9K vector (two fragments due to two XhoI restriction sites in pPIC9K, one present just before the multiple cloning site (MCS) and the other in the kanamycin resistance gene) and CSSK led to the formation of a recombinant pPIC9K-CSSK plasmid with a 'modified' α-factor signal sequence, devoid of the STE13 cleavage site. Schematic representation of the recombinant pPIC9K-CSSK plasmid with 'modified' α-factor signal sequence is outlined in FIG. 5. The resulting vector was named pPIC9K-alpha modified CSSK (FIGS. 6, 7). pPIC9K-alpha modified CSSK plasmid was digested with XhoI and NotI and run on a 0.8% agarose gel. An 1860 bp DNA fragment was identified following double digestion (FIG. 8), indicating successful cloning of CSSK in pPIC9K vector with alpha modified signal sequence. The shuttle vector was introduced into *E. coli* XL1BL cells by heat shock transformation methodology, and the alignment and sequence were confirmed by amplification and sequencing using the 5'AOX1 forward primer (SEQ ID NO: 30) and 3'AOX1 reverse primer (SEQ ID NO: 31, separately.

Example 3. Construction of Expression Vector Comprising the Modified Alpha Signal Sequence and Modified CSSK Gene To obtain a better yield of CSSK protein from expression in the yeast *Pichia pastoris*, the CSSK nucleic acid sequence was modified, taking into consideration preferential codons of the genes most expressed in *P. pastoris* while adding restriction sites at the ends of the synthetic gene to facilitate cloning into the *P. pastoris* expression vector. During the modification process, the following cis-acting sequence motifs were avoided where applicable: internal TATA-boxes, chi-sites and ribosomal entry sites; AT-rich or GC-rich sequence stretches; RNA instability motifs; repeat sequences and RNA secondary structures; (cryptic) splice donor and acceptor sites in higher eukaryotes. During the modification, several unique sites in the gene were preserved, for example, an Afl II restriction site, for generating fusion constructs.

The modification produced a sequence where negative cis-acting sites (such as splice sites, poly(A) signals, TATA boxes etc) were eliminated wherever possible, GC-content was adjusted to prolong mRNA half-life, and a good CAI (codon adaptation index) was achieved. The CAI describes how well the codons match the codon usage preference of the target organism. Thus, a CAI of 1.0 would be perfect, while a CAI of >0.8 is considered good (i.e. allowing high expression). CSSK modified for *Pichia pastoris* has a CAI value of 0.87. The modified gene should therefore allow high and stable expression rates in *Pichia pastoris*. Ultimately, a codon-modified sequence suitable for expression in *P. pastoris* was synthesized.

The polynucleotide sequence of the modified CSSK gene is as set forth in SEQ ID NO. 4 and the polypeptide sequence of encoded by the modified CSSK gene is as set forth in SEQ ID NO: 3. SEQ D NO: 3 has 100% identity to SEQ ID NO: 1. This sequence was used to transform a host cell of *P. pastoris* to express CSSK.

Figure 9:
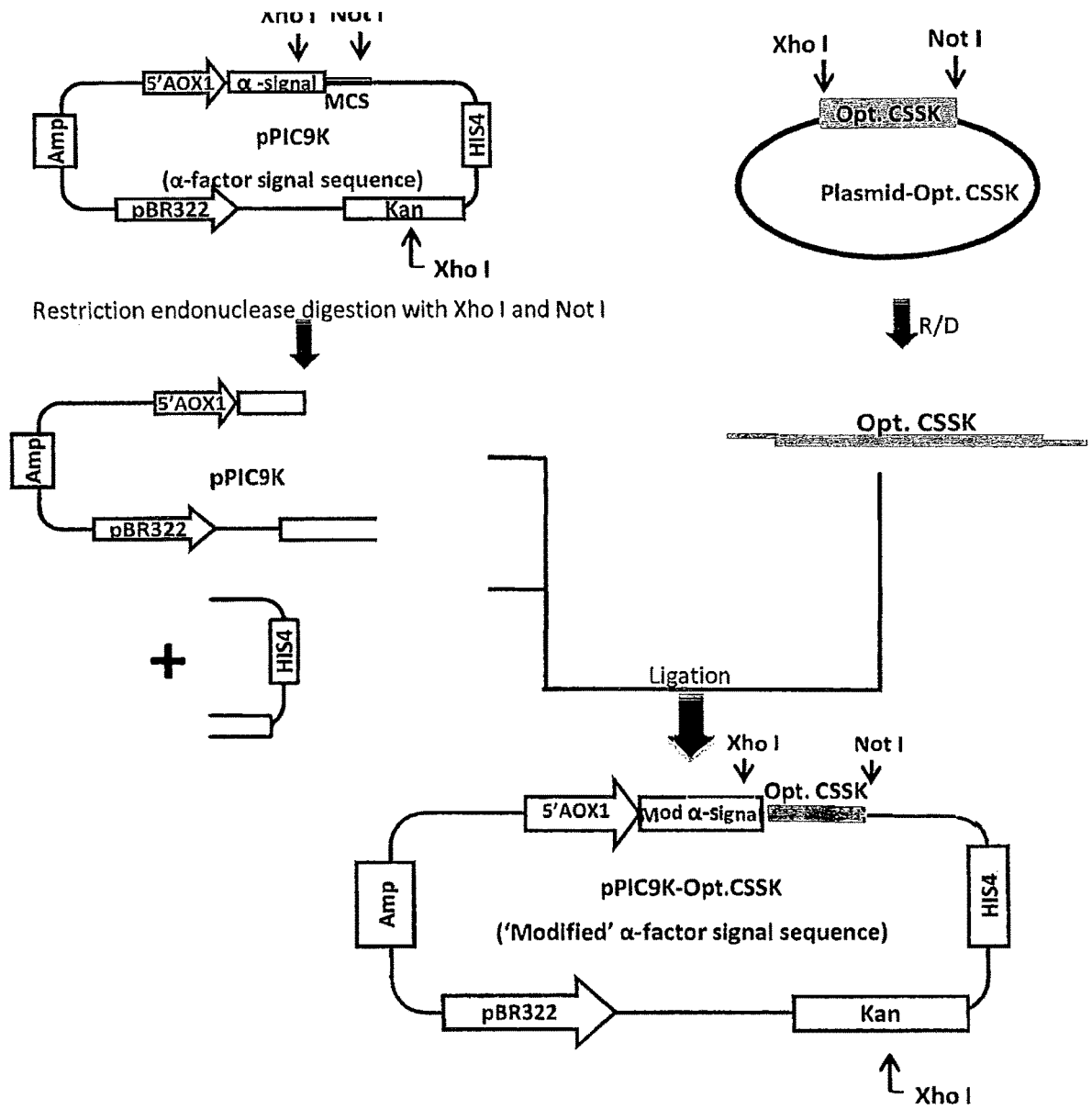
FIG. 9: Schematic representation of construction of the recombinant pPIC9K-Opt CSSK plasmid with 'modified' α-factor signal sequence and 'optimized' CSSK sequence. The CSSK sequence was amplified from a plasmid containing the optimized CSSK nucleotide sequence using primers with XhoI restriction site and KEX2 cleavage site at the 5' end and Not I restriction site at 3' end, respectively, followed by double-digestion of the amplified optimized CSSK PCR products with Xho I and Not I enzymes. The pPIC9K vector was also digested with XhoI and NotI, which resulted in cleavage of STE13 site along with generation of two fragments of pPIC9K vector due to the presence of two XhoI sites in the vector. Subsequently, three-piece ligation of XhoI and NotI digested fragments of pPIC9K vector (two fragments) and CSSK led to the formation of recombinant pPIC9K-Opt CSSK plasmid with a 'modified' alpha mating factor signal sequence.

Schematic representation of construction of the recombinant pPIC9K-Opt CSSK plasmid with 'modified' α-factor signal sequence is outlined (FIG. 9). The polynucleotide sequence of CSSK (SEQ ID NO: 4) (was amplified from a plasmid containing the optimized CSSK nucleotide sequence using primers with XhoI restriction site and KEX2 cleavage site at the 5' end and Not I restriction site at 3' end, respectively, followed by double-digestion of the amplified optimized CSSK PCR products with XhoI and NotI enzymes. The pPIC9K vector was also digested with XhoI and NotI, which resulted in cleavage of STE13 site along with generation of two fragments of pPIC9K vector due to the presence of two XhoI sites in the vector. Subsequently, three-piece ligation of XhoI and NotI digested fragments of pPIC9K vector (two fragments) and CSSK led to the formation of recombinant pPIC9K-Opt CSSK plasmid with a 'modified' alpha mating factor signal sequence. Correct cloning was confirmed by DNA sequencing. Further, in the 5' region of the gene, a sequence was introduced corresponding to the site of KEX2 of *S. cerevisiae* alpha signal sequence and a restriction site for XhoI. At the 3' end of the gene, a stop codon and a restriction site for NotI were introduced. The polynucleotide sequence of the modified CSSK gene with modified alpha sequence is as set forth in SEQ ID NO: 23 and the polypeptide sequence is as set forth in SEQ ID NO: 24.

Figure 10A:
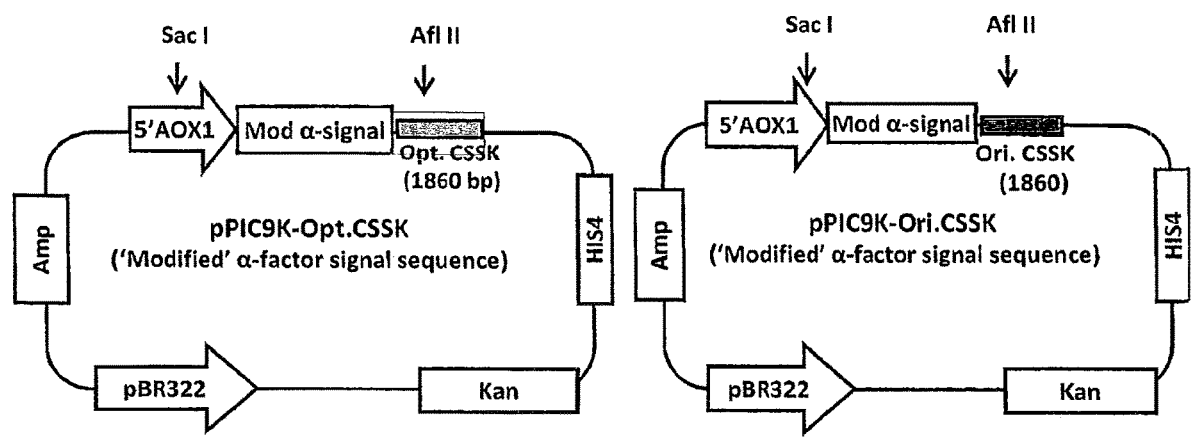
FIG. 10A: Schematic representation of construction of the chimeric recombinant pPIC9K-Native+Opt CSSK and pPIC9K-Opt+Native CSSK plasmids with 'modified' α-factor signal sequence. The pPIC9K-Opt CSK and pPIC9K-Native CSSK containing modified alpha factor signal sequences were digested with Sac I and Afl II restriction enzymes. The AOX1 promoter and CSSK have Sac I and Afl II restriction sites, respectively, which were utilized in generating chimeric recombinant plasmids.
Figure 10B:
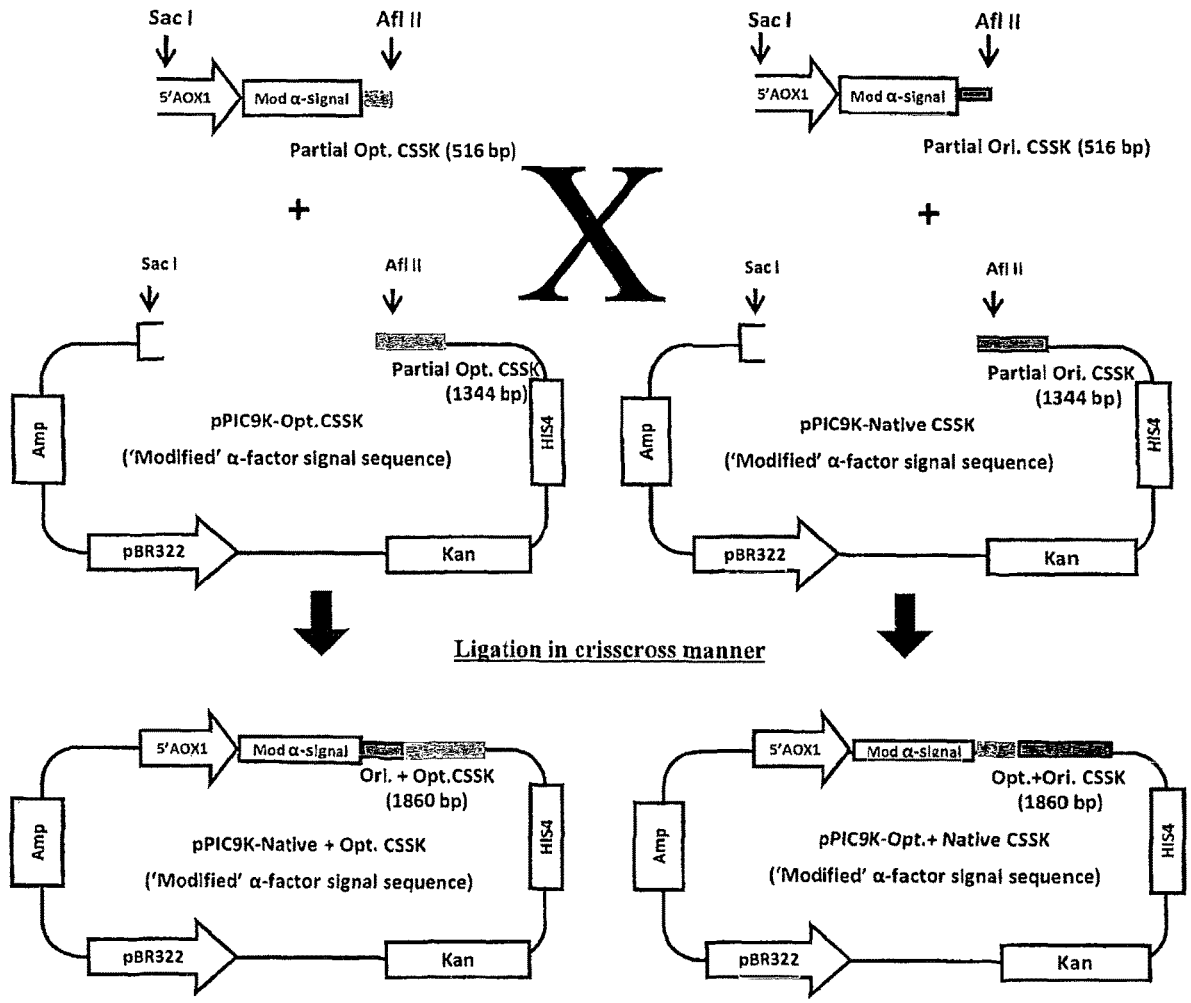
FIG. 10B: Strategy of constructing chimeric recombinant plasmids pPIC9K-Native+Opt CSSK and pPIC9K-Opt+Native CSSK.

Example 4. Construction of Expression Vector Comprising the Modified Alpha Signal Sequence and Chimera of 5' Region Modified CSSK and 3' Region of CSSK Gene Schematic representation of construction of the chimeric recombinant pPIC9K-Opt+Native CSSK plasmid with 'modified' α-factor signal sequence is outlined in FIG. 10. AOX1 promoter and CSSK comprises unique Sac I and Afl II restriction site, respectively in both the pPIC9K-Opt CSK and pPIC9K-Native CSSK recombinant plasmids and these sites were utilized in generating chimeric recombinant plasmids. The polynucleotide sequence of the chimeric CSSK gene 1 (opt+native CSSK gene) having 5' region (precisely, 1-516 bp; total 516 bp as shown underlined) of modified CSSK and 3' region (517-1860 bp; total 1344 bp) of original CSSK is as set forth in SEQ ID NO: 6. The sequence of polypeptide sequence encoded by chimeric CSSK gene 1 is as set forth in SEQ ID NO: 5.

Results of polynucleotide sequence alignment between original CSSK gene sequence (SEQ ID NO: 2) and a chimeric CSSK gene (SEQ ID NO: 6) revealed 93% identity between the chimeric CSSK gene 1 sequence and the original CSSK gene sequence.

Example 5. Construction of an Expression Vector with the Modified Alpha Signal Sequence, the 5' Region of Original CSSK and the 3' Region of the Modified CSSK Gene Schematic representation of construction of the chimeric recombinant pPIC9K-Native+Opt CSSK plasmid with 'modified' α-factor signal sequence is demonstrated in FIG. 10. In both the pPIC9K-Opt CSK and pPIC9K-Native CSSK recombinant plasmids, CSSK has an AOX1 promoter and unique Sac I and Afl II restriction sites, and these sites were utilized in generating the chimeric recombinant plasmids. Polynucleotide sequences of chimeric CSSK gene 2 (native+optCSSK gene) having 5' region (precisely, 1-516 bp; total 51 6 bp) of CSSK gene and 3' region (517-1860 bp; total 1344 bp as shown underlined) of modified CSSK gene is as set forth in SEQ ID NO: 8. The sequence of polypeptide encoded by chimeric CSSK gene 2 is as set forth in SEQ ID NO: 7.

Example 6. Transformation of *Pichia pastoris* with Vectors and Screening of CSSK Expression in Transformants Once the expression vectors pPIC9K-CSSK, pPIC9K-alpha modified CSSK, pPIC9K-optCSSK, pPIC9K-native+optCSSK and pPIC9K-opt+native CSSK were created, digestions were carried out to linearize the plasmids with either endonucleases Sac I or BglII followed by transformation into yeast strain GS115. YPD plate was streaked with GS115 glycerol stock and incubated at 30° C. for 48-72 h. A single isolated colony was inoculated into 5 ml YPD media and incubated overnight at 30° C. followed by inoculation of 500 µl of this overnight grown culture into 250 ml of fresh YPD media in 1litre flask. After the culture O.D reached to 1.3-1.5, the cells were pelleted at 5000 rpm for 5 min at 4° C. and resuspended in 250 ml of ice cold sterile water. Cells were again pelleted, followed by two subsequent washings with 125 ml of ice cold sterile water and 10 ml of 1 M sorbitol. After the washing, the cells were resuspended in 1 ml of 1M sorbitol. Next, the cells were pelleted under same conditions and resuspended in 1 ml of ice-cold 1 M sorbitol. The expression vector of CSSK construct was prepared by QIAGEN plasmid purification kit and concentrated by ethanol precipitation method. Ten µg of DNA was digested with BglII restriction enzyme. The linearized DNA was again concentrated by ethanol precipitation method. Finally DNA pellet was dissolved in 10 µl of sterile water to a final concentration of 1 µg/µl. An aliquot of electrocompetent cells was mixed with 10 µl linearized DNA (10 µg DNA). Mixture was then transferred to ice cold 0.2 cm electroporation cuvette and incubated for 5 min on ice. The cells were transformed with the linearized DNA using a gene-pulser electroporation apparatus (Biorad) at the settings of 1.5 KV, 25 µF with 200Ω resistance and 1 ml of ice-cold 1 M sorbitol was immediately added to the cuvette as described in the Invitrogen users manual. The cuvette contents were transferred to a sterile microcentrifuge tube. The cells were then incubated at 30° C. without shaking for 1-2 h and contents were spread on MD plates. The plates were incubated at 30° C. until colonies appeared.

Transformants were selected first by the non-histidine requiring growth, and if necessary, further by G418 (Geneticin) resistance. Through these selections, CSSK protein expressing strains, pPIC9K-CSSK/GS115, pPIC9K-alpha modified CSSK/GS115, pPIC9K-optCSSK/GS115, pPIC9K-native+optCSSK/GS115 and pPIC9K-opt+nativeCSSK/GS115, respectively, were obtained.
Analysis of the Transformants by Screening for CSSK Expression.

To assess CSSK expression, clones resulting from the transformation of *P. pastoris* were inoculated into 5 ml BMGY media separately and grown to log phase till O.D reached 2 to 6 at 30° C. with shaking. Cells were collected by centrifugation at 5000 rpm for 5 minutes at room temperature and the cell pellet was resuspended to an O.D of 1 in methanol containing BMMY medium for induction. Additional methanol was added at final concentration of 0.5% after every 24 h for 7 days. The methanol-induced culture supernatant was transferred to microcentrifuge tubes after each time course and cells were harvested by centrifugation at 6000 rpm for 5 min at room temperature. The supernatant was transferred to fresh tube. Time course samples were concentrated and then analyzed on 12% SDS-PAGE gels. The results revealed that out of the several clones, only few clones turned out to be positive in terms of secretory expression of CSSK.

Example 7. Development of a Plate Based Screening Method for *P. pastoris* CSSK Strains To select the best producing clone among different transformants by concentration of methanol-induced culture supernatant and their SDS-PAGE analysis is a labor-intensive procedure and "sieving" the best producer is a bottleneck in *Pichia pastoris* expression system. Therefore, to overcome the conventional tedious methodology of screening hundreds of transformants and selection of best producer clone, a direct plate-based screening-method (PBS-method) was developed.

In this screening method, the clones expressing CSSK were cultured after methanol-induction, and supernatants were used for activity assays. In order to optimize the PBS-method, different volumes of CSSK culture broth were used to carry out the functional assay based on exogenous plasminogen activation of the expressed CSSK to plot an activity versus dose response curve. The activity assay results clearly showed incremental increase in CSSK activity with increasing volumes of culture broth containing CSSK till the small volume of less than 10 µl, after which the response got saturated upon increasing the volume, followed by a decline in activity which could be due to interference by the media components present in culture broth in the enzyme activity.

Figure 11:
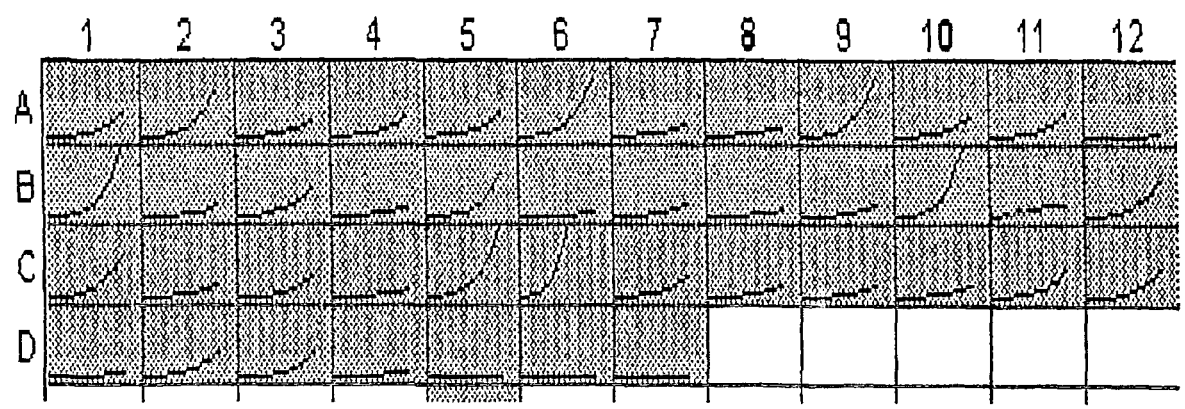
FIG. 11: Representative figure of CSSK screening. CSSK is expressed, secreted from individual transformants and screened for the best producer transformant using a plasminogen activity assay. In this multi-well plate, each block corresponds to a well containing a 100 µl reaction mixture. The curves represent the increase in absorption at 405 nm as a result of plasminogen activation wherein the plasmin acts on the amidolytic substrate. In row A, most transformants show little activity typical of the results of conventional cloning procedures.
Figure 12:
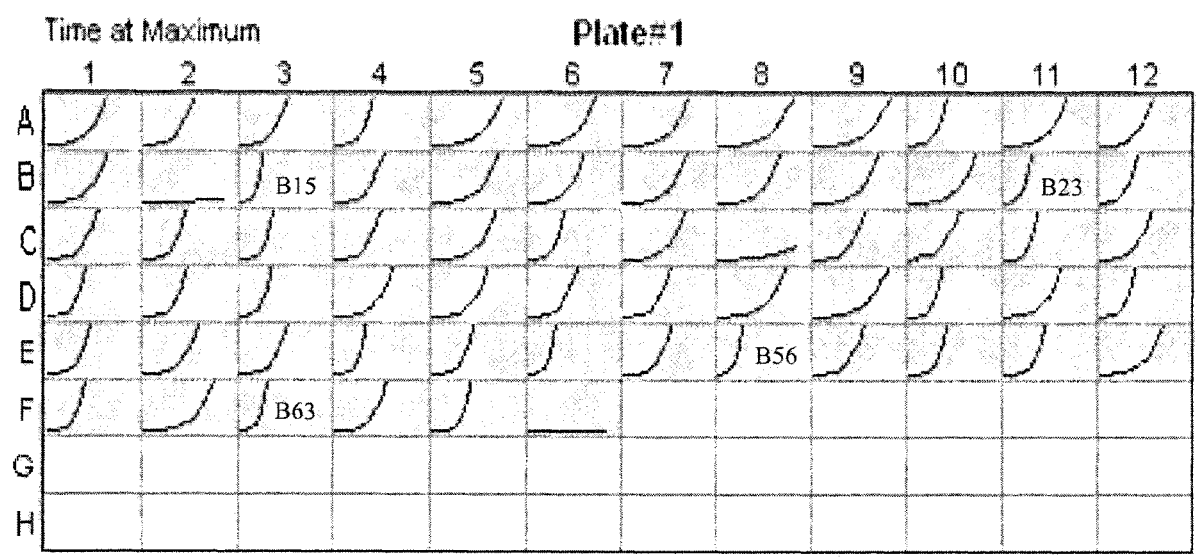
FIG. 12: Representative figure of alpha modified CSSK screening. Alpha modified CSSK was expressed, secreted from individual transformants and screened for the best producer transformant using a plasminogen activity assay. In this multi-well plate, each block corresponds to a well containing a 100 µl reaction mixture. Increased expression was observed by using vectors with modified alpha mating signal. Several clones were selected on the basis of rate of reaction, including clone numbers B15, B23, B56, and B63.

In order to obtain a hyper-producer clone, the individual transformants were cultured in falcon tubes containing 2.5 ml BMGY culture medium for 12-16 h till the O.D reached 2-6. The cells were then diluted in BMMY culture medium to an O.D of 1. The culture was maintained for 10 days with methanol being supplemented to a final concentration of 1% at every 24 h to compensate for methanol evaporation. After every 24 h, cells were centrifuged and culture broth was collected for activity assay. For the assay, 100 µl of reaction mixture in each well consisting of 50 mM Tris-Cl, 21.2 uM of plasminogen (PG), 0.5 mM chromozyme (tosyl-Gly-Pro-Lys-p-nitroanalide) and 3 µl of supernatant were used. The activity assay was performed by recording the change in absorbance at 405 nm as a function of time on microtiter plate reader (VERSAmax, Molecular Devices). The screening methodology in 96-well format and obtained results are shown in FIGS. 11-12. The strains were inoculated into 5 ml BMGY media separately and grown to log phase till O.D reached 2 to 6 at 30° C. with shaking. Cells were collected by centrifugation at 5000 rpm for 5 minutes at room temperature and the cell pellet was resuspended to an O.D of 1 in methanol containing BMMY medium for induction. The methanol-induced culture supernatant was transferred to microcentrifuge tube after each time course and cells were harvested.

The expression level of CSSK protein were checked in strains expressing CSSK, for example, pPIC9K-CSSK/GS115, pPIC9K-alpha modified CSSK/GS115, pPIC9K-optCSSK/GS115, pPIC9K-native+optCSSK/GS115 and pPIC9K-opt+nativeCSSK/GS115.

Figure 13:
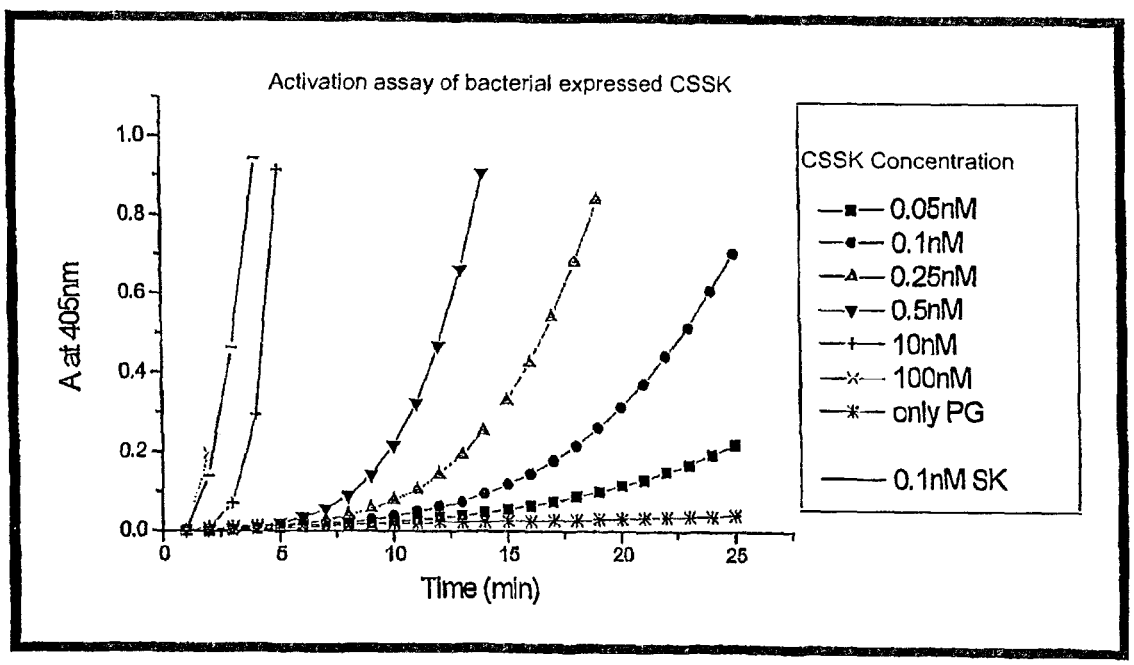
FIG. 13: Activation assay of E. coli expressed and purified CSSK utilized to obtain a standard plot for measuring the exact concentration of Pichia expressed CSSK. Varying concentrations of E. coli expressed and purified CSSK in the range of 0.05 nM, 0.1 nM, 0.25 nM, 0.5 nM, 10 nM and 100 nM were used to measure the slope of the activation curves and thus generate a standard plot of activity (slope) versus concentration of CSSK in the reaction mix. 0.1 nM streptokinase (SK) and plasmingen (PG) were used as a positive and negative control, respectively in the reaction mixtures.

The overall yield of CSSK in culture supernatant was determined using plasminogen activation (Table 1) on the basis of a standard plot employing known concentrations of *E. coli* expressed and purified CSSK versus slope of the activity (FIG. 13). The results are tabulated in Table 1.

TABLE 1

Calculation table for CSSK from the standard curve

| CSSK/GS115 clones | Slope $A_{405}/t^2 \times 10^{-3}$ | Conc. of CSSK (nM) (From standard curve) | Conc. of *P. pastoris* - expressed CSSK (µM) × Dilution factor (50) | Conc. of *P. pastoris* expressed CSSK (µg/ml) = µM × Mol. Wt (70 KDa) |
|---|---|---|---|---|
| Clone S3 | 9 | 2.4 | 0.12 | 8.4 |
| Clone S4 | 9 | 2.4 | 0.12 | 8.4 |

TABLE 1-continued

Calculation table for CSSK from the standard curve

| CSSK/GS115 clones | Slope $A_{405}/$ $t^2 \times 10^{-3}$ | Conc. of CSSK (nM) (From standard curve) | Conc. of P. pastoris - expressed CSSK (μM) × Dilution factor (50) | Conc. of P. pastoris expressed CSSK (μg/ml) = μM × Mol. Wt (70 KDa) |
|---|---|---|---|---|
| Clone S5 | 12 | 3.4 | 0.17 | 11.9 |
| Clone S24 | 22 | 6.2 | 0.31 | 21.7 |

Figure 14A:
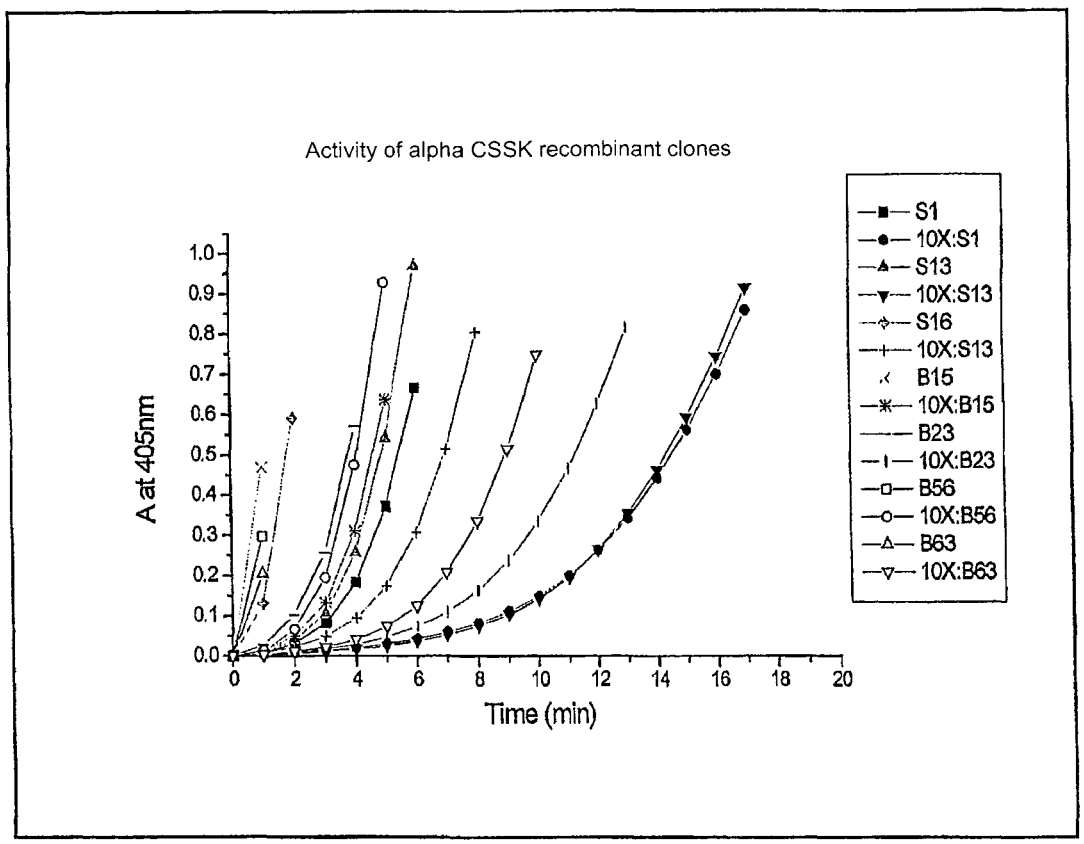
FIG. 14A: Activity assay of alpha modified CSSK culture supernatant and ten times diluted supernatant of selected clones using a plasminogen activity assay. Each block corresponds to a well of a multi-well plate containing a 100 µl reaction mixture. Enhanced activity was observed for Bgl II linearized vectors with the modified alpha mating signal from CSSK transformants, as compared to Sac I linearized DNA. Highest producing CSSK transformants S1, S13, and S16 were selected from hundreds of clones and subjected to vector digestion with Sac I. Selected clones were checked using a plasminogen activity assay. Transformants carrying Bgl II linearized vectors with modified alpha mating signal and CSSK displayed better activity on the basis of rate of reaction, including clone numbers B15, B23, B56, and B63.
Figure 14B:
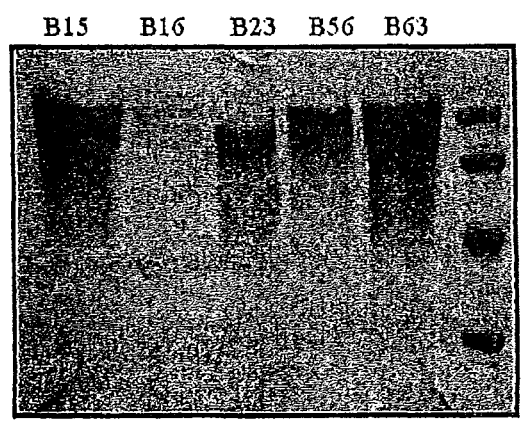
FIG. 14B: SDS-PAGE analysis of the culture supernatant of clones B15, B16, B23, B56, and B63 (equivalent volumes were loaded in each lane).

Selected clones on the basis of activity assay were tested again for activity after ten times dilutions and further validated by SDS-PAGE analysis (FIGS. 14A-B).

Table 2 provides a comparison of secretory expression levels obtained with the CSSK employing different nucleotide sequences but with same alpha modified signal sequence in *P. pastoris*. As can be seen in Table 2, CSSK expression was highest in a clone transformed with 5' optimized/3' native CSSK.

TABLE 2

Secretory expression levels obtained with CSSK employing different nucleotide sequences in *P. pastoris*.

| Protein | Expression level (mg/L) of best clone | CSSK gene |
|---|---|---|
| CSSK | 50 | Original |
| Opt CSSK | 8 | Modified and synthesized |
| Native + Opt CSSK | 12 | Original 5' region (516 bp) + Modified 3' region (1344 bp) [5' native/3' optimized CSSK] |
| Opt + Native CSSK | 110 | Modified 5' region (516 bp) + Original 3' region (1344bp) [5' optimized/3' native CSSK] |

Example 8. Culture and Purification of CSSK Protein

Figure 15:
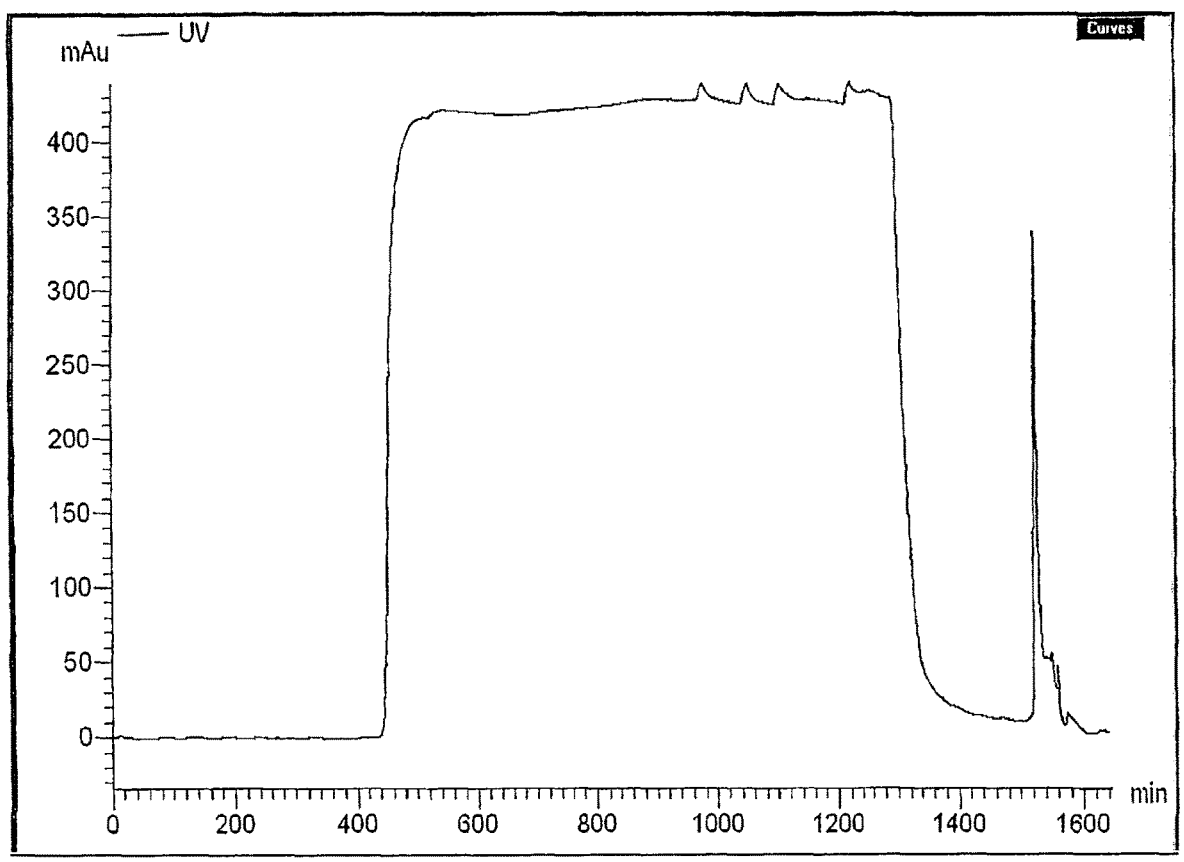
FIG. 15: Chromatographic elution profile of CSSK from a phenyl sepharose column. The culture broth was applied to the phenyl sepharose column pre-equilibrated with 0.25M NaCl in 25 mM phosphate buffer (pH 7.4) and washed with same buffer followed by 25 mM phosphate buffer, pH 7.4. CSSK was then eluted in a sterile water wash, shown by the distinct peak in the chromatogram.

Although secretory expression of CSSK in *Pichia* strains simplified protein extraction procedures relative to bacterial production of CSSK, the CSSK nevertheless had to be separated from the rest of the media components. To improve the separation steps, various salts and salt concentrations were tested that allowed binding of CSSK with the HIC material in the column at high efficiency, and arrived at a low salt concentration that selectively allowed its elution in a purer form, and salt conditions that maximized binding to phenyl sepharose beads without affecting protein stability was finalized. Large-scale expression of CSSK protein was performed in a 2 L flask. On the basis of reasonably good activity profile using plate based screening methodology, the clone of *P. pastoris* recombinant strains (pPIC9K-alpha modified CSSK/GS115) and pPIC9K-opt+nativeCSSK/GS115 producing maximum amount of protein was cultured in 125 ml BMGY culture medium at 30° C. with shaking (280 rpm) until the culture reached O.D$_{600}$ of 2-6. Cells were pelleted at 1500 g for 10 min and resuspended in 500 ml BMMY culture medium. Pure methanol was added every 24 h to a final concentration of 1%. After 48 h, cells were repelleted at 5000 g for 12 min and culture broth was resuspended in equilibration buffer: 0.25M NaCl and 25 mM phosphate buffer, pH 7.4. To purify CSSK, a phenyl-sepharose column was packed and equilibrated with same buffer. The culture broth was applied to an equilibrated column which was then subsequently washed with eight bed volumes of the same buffer followed by 25 mM phosphate buffer, pH 7.4 and then the protein was eluted with sterile water at a flow rate of 1.0 ml/min. The elution fractions were collected as 1 ml fractions (FIG. 15). All the purification steps were performed in ÄKTAprime chromatography system (GE Healthcare Life Sciences) at 4° C.

Example 9. Analysis of Purified CSSK Protein

Characterization of CSSK Protein Obtained from Single Step Purification.

Figure 16:
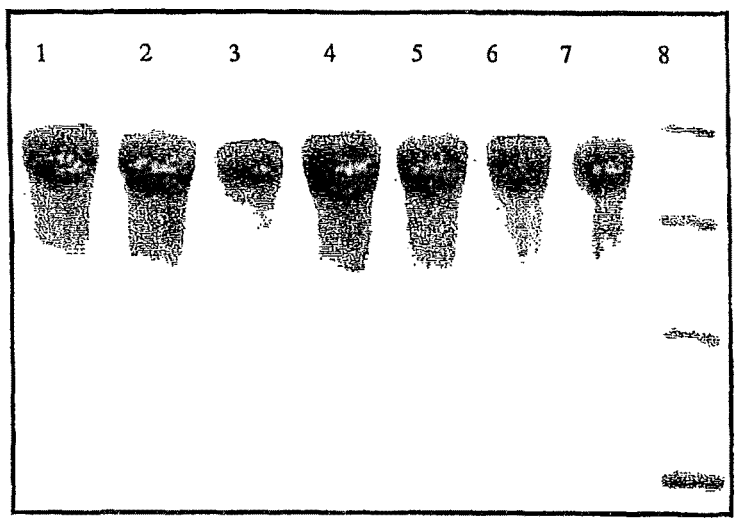
FIG. 16: 10% SDS-PAGE analysis of the CSSK expressed in recombinant P. pastoris pPIC9K-alpha modified CSSK/GS115/B15. Lane 1-7: peak fractions; 8, molecular weight markers.

SDS-PAGE was performed using 10% SDS-polyacrylamide gel. Samples including chromatographic fractions were dissolved in the SDS sample buffer under reducing conditions (FIG. 16A-16B). Gels were stained with coomassie brilliant blue R-250 (Sigma) for visualization of protein bands. Chromatographic fraction analysis revealed a peak at approximately 1520 minutes corresponding to expressed CSSK protein. SDS-PAGE analysis clearly revealed an upshift of molecular size of *Pichia* expressed CSSK protein compared to *E. coli* expressed CSSK. As an expression host, yeast offers many advantages over *E. coli* in terms of eukaryotic protein processing, folding, and post-translational modifications. Thus, an explanation of the increased size of *Pichia* derived CSSK might be the post translational modification, such as glycosylation.

Figure 17:
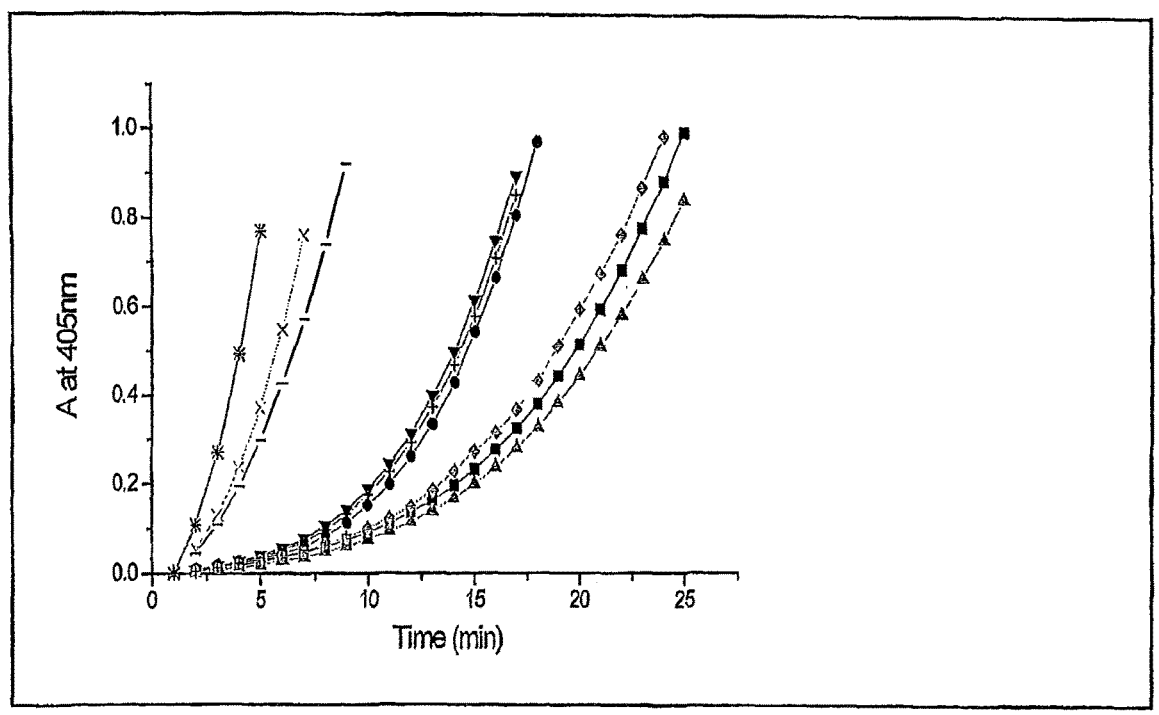
FIG. 17: Comparative plasminogen activator activity assay of CSSK expressed in a recombinant Pichia strain and CSSK expressed in E. coli. X-axis, time (min) and Y-axis, absorbance at 405 nm. Square, plasminogen activation activity of 0.1 nM concentration of P. pastoris expressed CSSK purified by Hydrophobic Interaction Chromatography (HIC). Circle, plasminogen activation activity of 0.5 nM concentration of P. pastoris expressed CSSK purified by HIC. Upward triangle, plasminogen activation activity of 0.1 nM concentration of E. coli expressed CSSK purified by HIC. Downward triangle, plasminogen activation activity of 0.5 nM concentration of E. coli expressed CSSK purified by HIC. Diamond, plasminogen activation activity of 0.1 nM concentration of E. coli expressed CSSK purified by HIC followed by Diethylaminoethyl (DEAE). (+), plasminogen activation activity of 0.5 nM concentration of E. coli expressed CSSK purified by HIC followed by DEAE. (x), plasminogen activation activity of 0.5 nM concentration of P. pastoris expressed CSSK purified by HIC plus human plasmin. (*), plasminogen activation activity of 0.5 nM concentration of E. coli expressed CSSK purified by HIC plus human plasmin. (−), plasminogen activation activity of 0.5 nM concentration of E. coli expressed CSSK purified by HIC followed by DEAE, plus human plasmin.

Biochemical Assay and Comparison with Bacterial Expressed CSSK:

*Pichia* expressed CSSK purified protein should show comparable activity to *E. coli* expressed CSSK purified protein. Plasminogen activation was tested and found to be essentially identical between *Pichia* expressed CSSK and *E. coli* expressed CSSK. In addition, there was a progressive decrease in the lag in activity in the presence of increasing amounts of plasmin added to the reaction (FIG. 17). This denotes that the yeast derived CSSK was as active as *E. coli* derived CSSK, and had the same dependence on plasmin for activation. The dependence of plasminogen activation capability on the presence of small quantities of plasmin (as present in blood clots) allows a fibrin clot specificity to be operational since unlike native SK, CSSK (either yeast or *E. coli* derived) now is inactive in the blood circulation (as plasmin is rapidly inactivated therein) but selectively is activated within the pathological blood clot by virtue of the "shielded" plasmin therein. The presence of this property in the yeast derived CSSK is a clear validation that the CSSK produced in this system, like that prepared from *E. coli*, has the same (most important) biological characteristics in terms of its plasminogen activator activity characteristics.

Immunoblotting with SK and Fibrin Binding Domain.

Figure 20:
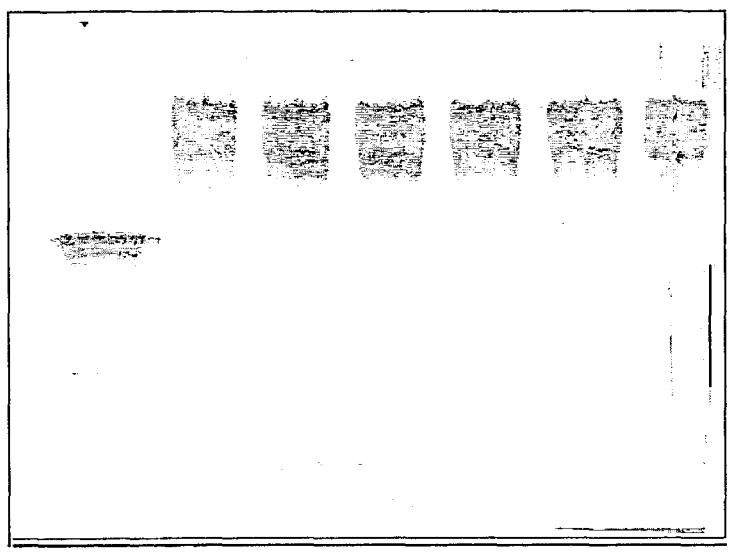
FIG. 20: Western Blot showing CSSK batches compared with standard (E. coli expressed SK). Lanes 1 to 5 represents CSSK batches at 5 L scale whereas lane 6 represents a 100 L scale batch.

CSSK batches were compared with bacterial expressed CSSK and native unglycosylated SK by Western Blot. As seen in FIG. 20, *Pichia*-expressed CSSK has a higher molecular weight due to glycosylation. The Western blotting revealed that the protein purified from five 5 L batches (FIG.

20, lanes 1-5) and one 100 L production batch (FIG. 20, lane 6) is consistent, indicating *Pichia* expressed CSSK has the same molecular weight across batches and batch sizes.

Biophysical Characterization of Purified CSSK

N-Terminal Sequencing:

Purified CSSK protein with the 'modified' α-factor signal sequence was transferred to a polyvinylidene difluoride (PVDF) membrane by electroblotting. Protein bands were excised and processed for N-terminal sequencing. SEQ ID NO: 20 provides the sequence of the modified alpha signal sequence and the beginning of the mature CSSK protein. In this sequence, a colon (:) denotes the start of the mature protein coding sequence and the sites of processing of different signal sequences, and the underlined residues depicts determined N-terminal sequences of mature CSSK protein. The non-underlined residues are the modified alpha signal sequences.

SEQ ID NO: 20
MRFPSIFTAVLFAASSALAAPVNTTTEDETAQIPAEAVIGYSDLEGDFDV

AVLPFSNSTNNGLLFINTTIASIAAKEEGVSLEKR: QAQQIVPIAEKC

The N-terminal sequencing of the protein was achieved by automated protein sequencers using Edman degradation. The Edman reagent, phenylisothiocyanate (PTC), is added to the adsorbed protein, together with a mildly basic buffer solution of 12% trimethylamine. The terminal amino acid, which is now derivatized, is then selectively detached by the addition of anhydrous acid. The derivative then isomerizes to give a substituted phenylthiohydantoin which is washed off and identified by chromatography, and the cycle is repeated.

N-terminal sequencing was performed to check whether the N-terminus of CSSK protein produced by yeast expression has the same N-terminal as that expressed by *E. coli*, the purified proteins from the several batches produced by fermentation were adsorbed on to PVDF membrane by electroblotting. Similarly blots were made with purified *E. coli* expressed and purified CSSK. The protein Blots were loaded on to BLOTT™ cartridge (reaction chamber) of Applied Biosystems Procise Protein Sequencer Model 491 cLC. It utilizes the Edman degradation chemistry to cause sequential degradation of the amino acid from the N-terminal of protein after derivatization.

N-terminal sequencing results revealed the correct proteolytic processing and removal of the signal sequence. Excision of the signal sequence resulted in the desired CSSK N-terminal sequence. Thus, secretory expression of CSSK using the modified alpha signal sequences led to N-terminal sequences without the problem of unexcised signal sequence and identical N-terminal sequence to *E. coli* expressed CSSK.

Example 10. Glycosylation Studies of Purified CSSK

Enzymatic Deglycosylation of CSSK.

Figure 18:
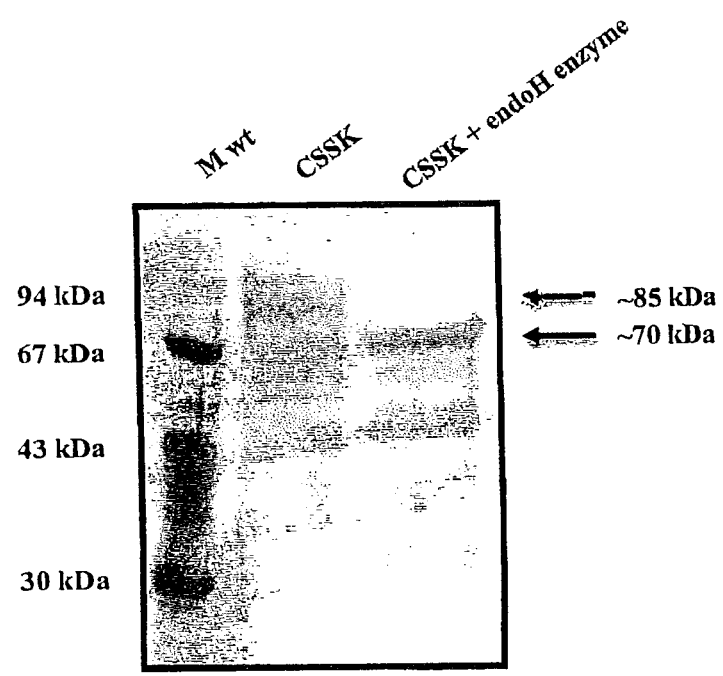
FIG. 18: 10% SDS-PAGE silver stained gel of glycosylated CSSK expressed by recombinant P. pastoris pPIC9K-alpha modified CSSK/GS115/B15 strain. Hydrophobic interaction chromatography was used to purify CSSK, which was treated with and without endoH enzyme to check the differences in glycosylated and deglycosylated forms. CSSK treated with endoH enzyme showed a band shift from 85 kDa to 70 kDa which is in agreement with the calculated molecular weight of CSSK. Lane 1 contains standard molecular weight markers ("M. wt.").

Deglycosylation of CSSK secreted from *P. pastoris* (20 µg) was performed by using endoglycosidase Hf and PNGase F (New England Biolabs, Beverly, USA), using their respective deglycosylation buffers and conditions, according to the manufacturer's instructions. The deglycosylated proteins were analyzed on 10% SDS-PAGE gels and stained with Coomassie brilliant blue R-250 to determine any shift in the protein molecular weight compared to untreated controls. A reduction in molecular size from 85 kDa to 70 kDa (equivalent to *E. coli* expressed CSSK) was observed when *Pichia* CSSK was incubated with endoH enzyme (FIG. 18). The molecular weight of deglycosylated CSSK was 69,695 Da whereas that of yeast expressed glycosylated CSSK was 80,515 Da. These results indicate that *Pichia* expressed CSSK was subject to glycosylation when expressed in yeast cells, but this did not affect its biological activity compared to *E. coli* expressed CSSK, which is devoid of any glycosylation.

Pas-Staining.

Figure 19:
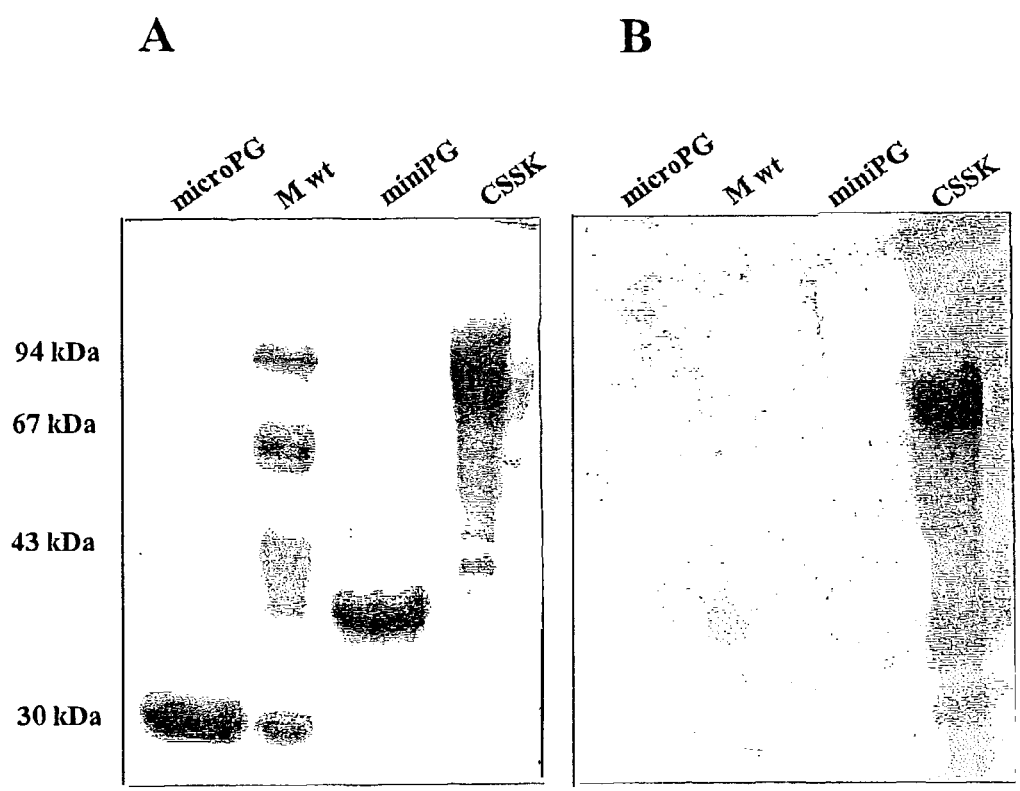
FIG. 19A: Glycosylation analysis of CSSK purified and expressed in recombinant P. pastoris pPIC9K-alpha modified CSSK/GS115/B15 as Coomassie brilliant blue-stained gel
FIG. 19B: Glycosylation analysis of CSSK purified and expressed in recombinant P. pastoris pPIC9K-alpha modified CSSK/GS115/B15 as PAS-stained SDS-PAGE gels. Pichia derived CSSK was stained by PAS reagent, indicating the presence of glycosylation. Lower molecular forms of plasminogen, for example, the non-glycosylated proteins miniplasminogen (miniPG) and microplasminogen (microPG), also obtained from Pichia, were used as a negative control for PAS staining.

To check the presence of glycosylated moieties, the SDS-PAGE gel was stained with Coomassie Brilliant Blue G-250 and in parallel another gel was treated with a glycoprotein detection kit (Sigma, USA). This detection system is a modification of the Periodic Acid-Schiff (PAS) method and yields magenta bands with a light pink or colorless background. The protocol for PAS staining was followed as per manufacturer's instructions. The *Pichia* expressed CSSK was stained by Periodic acid-Schiff (PAS) staining thus confirming the presence of glycosylation (FIGS. 19A-19B).

Culture of CSSK Expressing Strains in the Fermentor.

A 7 liter fermentor (with working volume close to 5 liters) was used for fermentation. The fermentor was equipped with automatic control of temperature, pH, dissolved oxygen, and air flow at the desired set-points. The fermentor was also equipped with data logging software for online record of the operating parameters. The fermentor was sterilized along with the growth medium after inserting probes for pH, dissolved oxygen and connecting air and exhaust filters. After sterilization and cooling, the remaining components of the medium were added to the vessel under aseptic conditions. Liquor ammonia was used for pH control and as a nitrogen source. After setting pH at desired set-point and after calibration of the DO probe, the fermentor medium was inoculated with the seed culture. pH, temperature and dissolved oxygen were maintained at desired set-points throughout the fermentation. The stirrer speed was maintained between 300-900 rpm and air flow at 1.0±0.2 vvm. After the completion of batch phase, fed-batch phase was started by addition of feed medium at a pre-determined flow rate. Pure oxygen was connected and was taken when ever needed by the DO controller. The culture was grown to desired optical density and was induced by adding methanol. Samples were taken at regular intervals and tested for $OD_{600}$ and expression level by activity assay. After maximum levels of expression were achieved the batch was harvested on $10^{th}$ day post induction.

For obtaining CSSK from *Pichia* fermentation at a higher scale (100 Liter), a 15 L fermentor (with working volume close to 10 L) was used for inoculum preparation. The production fermentor (140 L) with working volume close to 100 L was inoculated with 10% inoculum. Both these fermenters were equipped with automatic control of temperature, pH, dissolved oxygen, air flow at the desired set-points. The fermentor was also equipped with data logging software for online record of the operating parameters. The fermentor was sterilized in-situ using steam in place (SIP) with the growth medium after inserting probes for pH, dissolved oxygen and connecting air and exhaust filters. Post sterilization and cooling, remaining components of the medium were added to the production (100 L) fermenter under aseptic conditions. Liquor ammonia was used for pH control and as a nitrogen source. After setting pH at desired set-point and after calibration of the DO probe, the fermentor medium was inoculated with the seed culture. pH, temperature and dissolved oxygen were maintained at desired set-points throughout the fermentation. The stirrer speed was maintained between 150-400 rpm and air flow at 1.0±0.2 vvm. After the completion of batch phase, fed-batch phase was started by addition of feed medium at a pre-determined flow rate. Pure oxygen was connected and was taken when ever needed by the DO controller. The culture was grown to desired optical density and was induced by adding methanol. Samples were taken at regular intervals and tested for $OD_{600}$ and expression level by activity assay. Batches were harvested on $10^{th}$ day post induction, after maximum levels of expression were achieved. Yields exceeding 2 g of CSSK per Liter were typically obtained.

Purification. Solid Liquid Separation:

The fermentation broth was collected from the fermentor and subjected to centrifugation for the separation of cells from the culture medium. The wet cell weight and the total volume of culture supernatant obtained were recorded. To the supernatant, final concentration of Sodium chloride and Phosphate buffer was maintained as 0.1M and 20 mM respectively to achieve final conductivity 50±10 mS/cm and it was immediately loaded on to the chromatographic column. The biomass was subjected to autoclaving followed by incineration. At 100 L scale the clarification of broth was performed using Grand stand hollow fiber system (G.E Healthcare) using 0.2 μm hollow-fiber cartridges. The conductivity of permeate containing desired protein was set to 50±10 mS/cm using 5M NaCl and 1M PB (pH 7.2) before loading on to chromatographic column.

Chromatography:

The modified streptokinase was purified from the culture supernatant using a hydrophobic interaction chromatography (HIC) column. The culture supernatant was loaded onto the column, after extensive washing with different buffers, and the protein was eluted. The purified protein from this step was then applied on to ion-exchange column for the removal of some cationic impurities. The protein from this step was concentrated and desalted using cross-flow ultra-filtration (30 kDa) then subjected to lyophlization. The final product was sterile filtered and stored at −80 C.

Example 11. In Vivo Study of CSSK Dose-Response in Primate Model of Thrombosis

Thrombolytic response to CSSK in cynomolgus monkeys (3.3-6.9 kg) was studied. Animals were subjected to surgery to gain access to the femoral artery in order to introduce a blood flow probe for monitoring femoral arterial blood flow. Additionally, a needle electrode was introduced into the femoral artery to induce thrombosis. A platelet rich/fibrin clot was generated spontaneously by passing current (150 uA) through the electrode which resulted in endothelial disruption of the inner lining of the blood vessel followed by platelet adherence to the injury site. Platelet aggregation ensued followed by fibrin deposition and cross linking. CSSK was administered by bolus injection to determine the dose response characteristics of the agents as effective lytics in previously thrombosed femoral arteries. The time to reperfusion, incidence of reperfusion and time to reocclusion was monitored as well as residual thrombus weight, bleeding time and serial laboratory measurements of plasma fibrinogen.

Animals were sedated prior to animal handling, conducting technical procedures and surgical preparation using a cocktail containing 0.2 mg/kg Acepromazine and 0.02 mg/kg Atropine followed by a 4 mg/kg Propofol injection via a cephalic or saphenous vein intravenous catheter (i.v.). Following sedation, animals were prepared for surgery/procedure: The animals were immediately intubated and provided inhalant isoflurane anesthetic at 2.5%-4% for induction and 0.5-2.5% for maintenance delivered through either a volume-regulated respirator or rebreathing apparatus. Drug administration was performed through the IV catheter and the drug, dose, route, and site of administration documented. Lactated ringer solution was administered at 10 ml/kg/hr throughout surgery.

The femoral artery was instrumented for monitoring of arterial blood pressure and heart rate. The femoral vein was cannulated for blood sampling and the administration of intravenous fluids. The contralateral femoral artery was carefully dissected away from the femoral vein using topically applied Lidocaine HCl (2% solution) to aid in the prevention of vasospasm. A 2.0 mm perivascular flow probe (Transonic Systems) was positioned on the femoral artery approximately 15 mm distal from the point where the inferior epigastric artery originates from the femoral artery. The perivascular space was filled with a viscous acoustic gel that allows for measurement of phasic and mean arterial femoral blood flow by the ultrasonic transit time method (Transonic Systems).

A small electrode fashioned from a 25 gauge hypodermic needle was utilized to produce endothelial injury. The electrode was introduced into the vascular lumen between the branch at the inferior epigastric artery and the blood flow probe. Animals were bolus dosed with CSSK after the thrombus formed and had been aged for 1 hr. During the aging process, sodium heparin was administered intravenously to prevent clot extension (100 U/kg, iv following occlusion and an additional 50 U/kg/hr, iv). Blood samples were collected and recorded at baseline, post-thrombotic occlusion, just prior to CSSK bolus iv dose, and then 30 min, 1 hr, 2 hr, 3 hr and 4 hr after CSSK dosing. Blood was collected at designated timepoints from an independent auricular marginal venipuncture for, aPTT, ACT and fibrinogen determinations. A total of ~5 mL blood was collected for each timepoint.

Coagulation Testing.

Blood draws of approximately 1.8 mL into sodium citrate tubes (0.2 mL of 3.8% sodium citrate) was accomplished. Blood samples were kept on ice until centrifugation at 4° C. at 1,500 g for 15 minutes to prepare plasma. Citrated plasma samples were siphoned off using a pipette and evenly divided among 2 individual clean labeled tubes. Samples were stored at −80° C. for analysis of activated partial thromboplastin time (aPTT). ACT's were run on-site. One vial was analyzed and one vial stored as a back-up sample.

Plasma Fibrinogen:

Approximately 3 mL of blood was obtained and added to EDTA/PPACK tubes. Blood samples were kept on ice until centrifugation at 4° C. at 1,500 g for 15 minutes. The plasma EDTA/PPACK samples were siphoned off using a pipette and evenly divided among 2 individual clean labelled tubes. Samples were stored at −80° C. for later analysis of plasma fibrinogen. One vial was analyzed using a precipitation method to determine plasma fibrinogen levels (Orsonneau, J., et al., Clin. Chem., 35:2233, 1989).

Pharmacokinetics (PK).

Blood samples for PK analysis of CSSK plasma levels were obtained from each animal in the study at times 0, 1, 3, 10, 15, 30, 60, 120, 240, 300 and 360 min. These samples are analyzed in a S2251 amidolytic bioassay (Grierson D S and Bjornsson T D, Clin Pharmacol Ther. 1987 March; 41(3):304-13).

Bleeding Time.

Cutaneous bleeding times were determined on a forearm that was subjected to 40 mmHg venostasis by an occluder cuff placed on the upper arm. A uniform incision (5 mm long×1 mm deep) was made with a SURGICUT template bleeding device. Bleeding time was determined to be the time in seconds required to form a primary platelet plug that was sufficient to arrest the flow of blood from the incision site.

Blood Pressure, Heart Rate & Treatment Vessel Blood Flow.

Percutanous arterial access was obtained during the procedure as described and utilized for arterial blood pressure monitoring. The side port of the arterial sheath was connected to a Datascope Passport System for monitoring systolic arterial pressure (SAP), diastolic arterial pressure (DAP), mean arterial pressure (MAP) and heart rate (HR). All data were monitored and digitally recorded continuously on an AD Instrument throughout the procedure.

Results

Thrombolytic Efficacy and Residual Thrombus Mass.

The efficacy of thrombolysis was assessed by the ability of CSSK to restore blood flow through a previously thrombosed and completely occluded femoral artery. Thrombotic occlusion was achieved via electrolytic injury to the inner surface of the blood vessel, resulting in endothelial disruption which is followed by platelet adherence, platelet aggregation and fibrin deposition.

Table 3 illustrates the primary endpoints of the study for CSSK: incidence of reperfusion, time to reperfusion, incidence of re-occlusion and time to re-occlusion. CSSK was evaluated at i.v. bolus doses of 25,000, 50,000 and 100,000 U/kg. Based on the specific activity of CSSK (70,000 U/mg) these 3 doses of CSSK translate into 0.35, 0.71 and 1.42, mg/kg, respectively. Two animals were studied per dose group.

CSSK administered at 25,000 U/kg (0.35 mg/kg) failed to elicit reperfusion of the target vessel in 2 monkeys studied. The residual thrombus mass was relatively high, compared to other groups treated with higher doses of CSSK, indicating that the low dose is not sufficient, in this animal model, to degrade the clot sufficiently to achieve successful reperfusion (defined as 50% or greater restoration of blood flow compared to the baseline flow before the thrombus was induced).

CSSK administered at the next higher dose of 50,000 U/kg (0.71 mg/kg), elicited successful reperfusion in 1 of 2 animals studied and in both animals, the residual thrombus mass was very low.

At the highest dose of CSSK utilized (100,000 U/kg or 1.42 mg/kg), successful reperfusion occurred in both animals, with a low residual thrombus mass, as seen in the previous mid-dose CSSK group.

FIG. 21 represents a real time analysis of femoral arterial blood flow. Open areas of the timeline indicate that the target vessel is open and blood is flowing at 50% or greater level as defined above. Closed areas indicate that the vessel is thrombosed with no blood flow. CSSK is administered at the arrow and then the progression of the lytic effect can be realized visually. This convention was originally described by Gold et al. (Circ., 77(3):673, 1988) to describe the actions of tPA and related analogs.

Figure 22A:
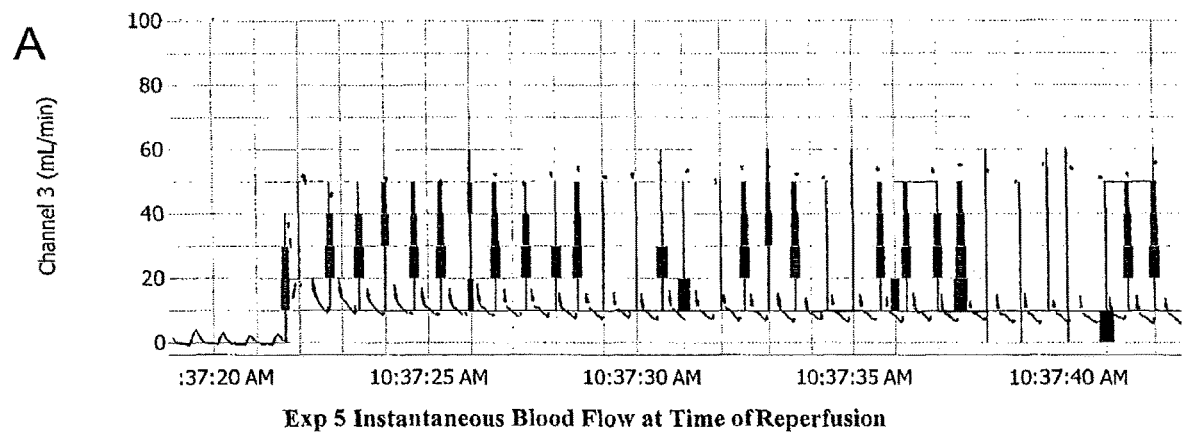
FIG. 22A: Instantaneous blood flow following reperfusion.
Figure 22B:
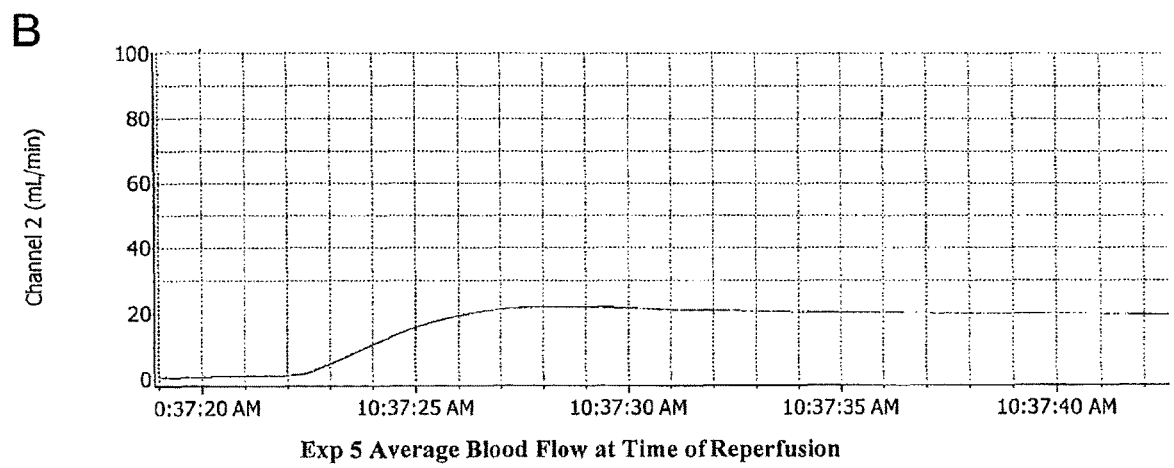
FIG. 22B: Average blood flow following reperfusion.

Real time femoral arterial blood flow tracings at the time of effective CSSK-induced thrombolysis are provided in FIGS. 22A-22B. The top tracing is the pulsatile blood flow pattern that fluctuates with diastole and systole and the bottom tracing is the mean (average) blood flow through the target vessel (femoral artery). Both animals treated with the highest dose of CSSK (100,000 U/kg or 1.4 mg/kg) were effectively reperfused at 35 and 162 min, respectively.

Plasma Fibrinogen Levels.

Plasma fibrinogen levels are illustrated in Table 4. CSSK elicited only minor fluctuations in fibrinogen levels post-treatment with a tendency to fall off over time, a phenomenon noted previously in PBS only treated cynomolgus monkeys.

TABLE 3

Thrombolytic Efficacy of CSSK in Cynomolgus Monkey Femoral Artery

| Animal # | CSSK Dose (U/Kg) | Occlusion time (min) | Reperfusion | Time to Reperfusion (min) | Residual Thrombosis Weight | Time to re-occlusion (min) |
| --- | --- | --- | --- | --- | --- | --- |
| 1 | 25,000 | 12 | No | na | 7 | na |
| 2 | 25,000 | 17 | No | na | 15 | na |
| 3 | 50,000 | 53 | Yes | 102 | 2 | 9 |
| 4 | 50,000 | 53 | No | na | 2 | na |
| 5 | 100,000 | 29 | Yes | 35 | 2 | na |
| 6 | 100,000 | 39 | Yes | 162 | 3 | na |

TABLE 4

| | | Plasma Fibrinogen Levels (mg/dl) | | | | | | | |
|---|---|---|---|---|---|---|---|---|---|
| Animal | CSSK Dose (U/kg) | Baseline | Occl. | TX0' | TX30' | TX1 hr | TX2 hr | TX3 hr | TX4 hr |
| 1 | 25,000 | 232 | 186 | 160 | 188 | 181 | 150 | 120 | 115 |
| 2 | 25,000 | 350 | 364 | 233 | 233 | 262 | 287 | 228 | 231 |
| 3 | 50,000 | 238 | 196 | 192 | 162 | 141 | 148 | 157 | 134 |
| 4 | 50,000 | 246 | 250 | 223 | 183 | 171 | 181 | 214 | 230 |
| 5 | 100,000 | 117 | 222 | 181 | 171 | 165 | 157 | 141 | 109 |
| 6 | 100,000 | 350 | 321 | 270 | 252 | 240 | 178 | 185 | 122 |

Bleeding Time.

Bleeding times fluctuated in this study and no consistent pattern in response to CSSK was observed.

Mean Arterial Blood Pressure and Heart Rate.

Mean arterial blood pressure and heart rate were monitored constantly throughout the duration of each experiment. CSSK, at all doses tested, did not significantly alter mean arterial blood pressure or heart rate.

Conclusion.

The primary objective was to determine the dose-response characteristics of CSSK in a model that is as close to a human thrombotic situation as possible. The non-human primate model utilized herein provides critical data to the development of novel thrombolytic agents, especially in providing important information on dose selection for human clinical trials. The data obtained in the present study provide a strong pharmacological basis for human dosing of CSSK. The CSSK dose of 1.42 mg/kg (100,000 U/kg) that was effective in both animals studied was also effective in 2 previous cynomolgus monkeys studied and thus this dose is now collectively effective in 4 of 4 non-human primates to elicit successful reperfusion.

The other end of the dose response was also identified in this study at the low dose of 0.35 mg/kg (25,000 U/kg). This dose failed to reperfuse 2 animals; however in a previous study, this dose was effective at lysing the clot but the vessel quickly re-occluded. Thus, the 0.35 mg/kg dose defines the approximate bottom end of the dose-response curve.

The mid dose utilized of 0.70 mg/kg (50,000 U/kg) reperfused 1 of 2 animals tested. In a previous study this dose was also effective at the 50% level and thus the total collectively at this dose is 2 of 4.

As thus shown, in vivo CSSK (0.7-1.4 mg/kg as an iv bolus), lysed experimentally-induced femoral arterial thrombi in cynomolgus monkeys with relatively minor fluctuations in plasma fibrinogen, forearm bleeding time or hemodynamics.

The predicted CSSK human dose of approximately 0.5 mg/kg falls close to the dose response range of the non-human primate. The non-human primate is modestly less sensitive to human-derived plasminogen activators and thus it is not surprising that the human dose may be slightly lower than predicted from the non-human primate.

GLP safety studies with CSSK were conducted at doses of 1, 3, and 10 mg/kg/day for 5 consecutive days in male and female cynomolgus monkeys. The CSSK at these dose levels was generally well tolerated in both the male and female monkeys. Thus, the low dose of 1 mg/kg is considered the No-Observed Adverse Effect Level (NOAEL) for daily repeat-dose administration of CSSK administered via bolvs i.v. injection in cynomolgus monkeys.

A thrombolytic agent that may be administered as a single bolus has many advantages for patients diagnosed in rural situations where access to a hospital facility is literally hours away. With the speed of evolving myocardial infarctions, time is of the essence and thus a clot specific lytic drug, such as CSSK, that could be administered as a single bolus, would potentially save myocardium at risk of infarction and thereby people's lives.

Example 12. Efficacy and Safety of Bolus Injection of CSSK as Produced as Described Herein in Patients with ST-Segment Elevation Acute Myocardial Infarction (STEMI This study was conducted in India, more specifically, in Nagpur, Baroda, Karamsad, India Route of Administration:

IV bolus over 2 min, peripheral vein

Dosage:

20 mg of CSSK produced as described herein

Ten patients with documented STEMI enrolled voluntarily at 3 centers (Nagpur, Baroda, and Karamsad, India). All patients (n=10) were treated with CSSK, in less than 6 hrs from onset of their reported chest pain. There were 9 males and 1 female treated with the CSSK and ages ranged from 40-61 and weight from 41-80 kg. The patients were evaluated angiographically 90 minutes after CSSK administration and all were stented (independent of TIMI flow rate 0-3)

The results are tabulated below.

TABLE 5

Coronary TIMI Blood Flow Characteristics and Patient Outcomes

| Clinical Site | Patient No. | TIMI Flow (0-3) | Coronary Stent Implanted (Y/N) | Clinical Outcome |
|---|---|---|---|---|
| Nagpur | 001 | 0 | Y | Released |
| Nagpur | 002 | 0 | Y | Released |
| Baroda | 001 | 3 | Y | Released |
| Baroda | 002 | 0 | Y | Released |
| Baroda | 003 | 0 | Y | Released |
| Karamsad | 001 | 3 | Y | Released |
| Karamsad | 002 | 2 | Y | Released |
| Karamsad | 003 | 2 | Y | Released |
| Karamsad | 004 | 2 | Y | Released |
| Karamsad | 005 | 0 | Y | Released |

Other Results were as Follows:
- No minor or major bleeding diatheses occurred in any of the 10 patients treated with 20 mg CSSK
- Hemodynamics (BP, heart rate, respiratory rate) were not appreciably altered by CSSK administration.
- Biochemical and clinical laboratory coagulation parameters were not changed substantially due to treatment with CSSK.

There was no serum chemistry evidence of liver injury from CSSK. However, there was a slight elevation of liver enzymes, but these the SGOT (and slight SGPT), but these were considered secondary to the acute myocardial ischemic events occurring in these patients.

Figure 23:
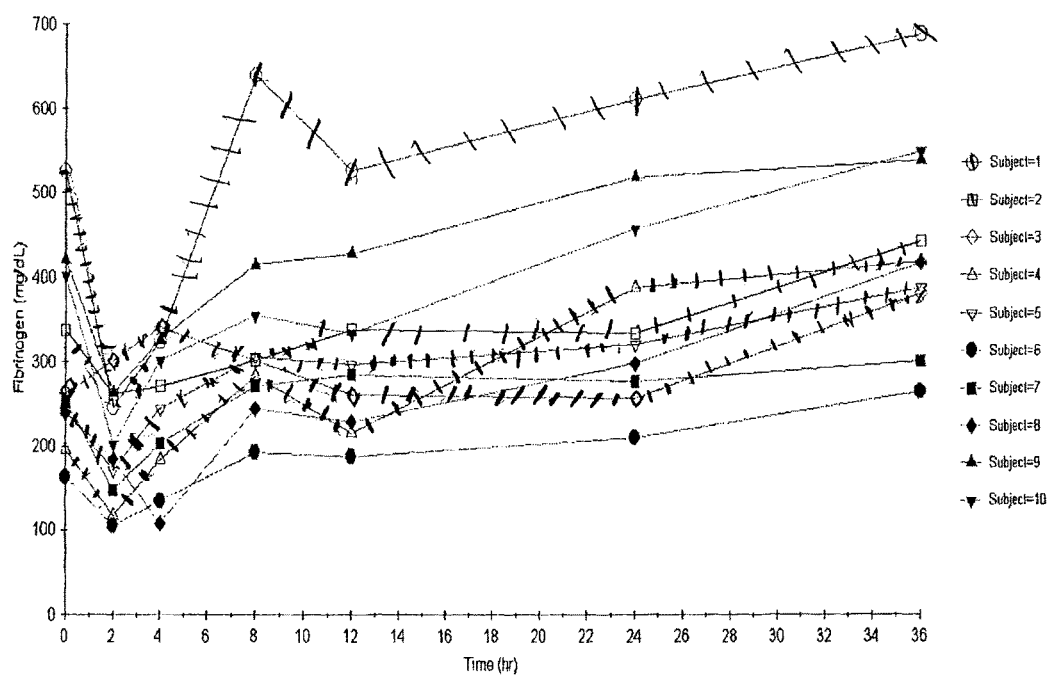
FIG. 23 graphically depicts the effect of the administration of CSSK, as prepared herein, on plasmin fibrinogen levels in patients with acute segment elevated myocardial infarction (AMI/STEMI).

Plasma fibrinogen was evaluated in all patients at predose and up to 36 hours following administration of CSSK. There was an expected and consistent decrease in plasma fibrinogen levels that recovered 4-8 hours after drug administration. No patient had a fibrinogen drop to less than 100 mg/dL., as shown in FIG. 23.

TIMI grade 2 or 3 flow, as a demonstration of efficacy, was achieved with IV bolus SMRX-11 (20 mg) in 5 of 10 patients.

All patients were released.

REFERENCES

Castellino F J (1981). Recent advances in the chemistry of the fibrinolytic system. Chem Rev 81, 431-446.

Cregg J M, Barringer K J, Hessler A Y, Madden K R (1985). Pichia pastoris as a host system for transformations. Mol Cell Biol. December; 5(12):3376-85.

Grierson D S, Bjornsson T D (1987). Pharmacokinetics of streptokinase in patients based on amidolytic activator complex activity. Clin Pharmacol Ther. 41(3):304-13.

Hagenson M J, Holden K A, Parker K A, Wood P J, Cruze J A, Fuke M, Hopkins T R, Stroman D W (1989). Expression of streptokinase in Pichia pastoris yeast. Enzyme Microb Technol 11, 650-656.

Malke H, Ferretti J J (1984). Streptokinase: cloning, expression, and excretion by Escherichia coli. Proc Natl Acad Sci USA 81, 3557-3561

Malke H, Gerlach D, Kohler W, Ferretti J J (1984). Expression of a streptokinase gene from Streptococcus equisimilis in Streptococcus sanguis. Mol Gen Genet 196, 360-363.

Simon J R, McEntee K (1989) A rapid and efficient procedure for transformation of intact Saccharomyces cerevisiae by electroporation. Biochem Biophys Res Commun. 15; 164(3):1157-1164.

Orsonneau J L, Douet P, Massoubre C, Lustenberger P, Bernard S (1989) An improved pyrogallol red-molybdate method for determining total urinary protein. Clin Chem; 35:2233-2235.

Wong S L, Ye R, Nathoo S (1994). Engineering and production of streptokinase in a Bacillus subtilis expression-secretion system. Appl Environ Microbiol 60, 517-523.

BOOKS

Sambrook J, Fritsch E F, Maniatis T (1989). Molecular Cloning: a Laboratory Manual. Cold Spring Harbor Laboratory Press, Cold Spring Harbor, N.Y., USA 18th Ed., ed. Gennaro, Mack Publishing Co., Easton, Pa., 1990

4th ed., Ed. Rowe et al. Pharmaceutical Press, Washington, D.C

PATENTS

U.S. Pat. No. 7,163,817 January/2007 Sahni et. al 435/212

U.S. Pat. No. 8,143,027 March/2012 Sahni et. al 435/71.1

---

The invention claimed is:

1. An eukaryotic expression cassette comprising a polynucleotide, said polynucleotide comprising a yeast methanol inducible alcohol oxidase I promotor sequence or a yeast methanol inducible alcohol oxidase II promoter sequence, a modified *Pichia* alpha signal gene sequence, wherein the modified *Pichia* alpha signal gene sequence is an alpha signal gene sequence devoid of the STE13 protease cleavage site, a nucleic acid sequence encoding clot specific streptokinase and a transcription terminator sequence, wherein the nucleic acid sequence encoding clot specific streptokinase is selected from the group consisting of a nucleotide sequence with 100% identity to the sequence set forth in SEQ ID NO: 2, a nucleotide sequence with at least 85% identity to the sequence set forth in SEQ ID NO: 4, a nucleotide sequence with at least 85% identity to the sequence set forth in SEQ ID NO: 6 and a nucleotide sequence with at least 85% identity to the sequence set forth in SEQ ID NO: 8.

2. The expression cassette according to claim 1, wherein the nucleic acid sequence encoding clot specific streptokinase is selected from the group consisting of SEQ ID NO: 2, SEQ ID NO: 4, SEQ ID NO: 6 and SEQ ID NO: 8.

3. The expression cassette as claimed in claim 1, wherein the modified alpha signal gene sequence is as set forth in SEQ ID NO: 10.

4. An expression vector comprised of the expression cassette according to claim 1.

5. The expression vector as claimed in claim 4, wherein the expression vector comprises a polynucleotide selected from the group consisting of a polynucleotide sequence with 100% identity to the sequence set forth in SEQ ID NO: 2, a polynucleotide sequence with at least 85% identity to the sequence set forth in SEQ ID NO: 4, a polynucleotide sequence with at least 85% identity to the sequence set forth in SEQ ID NO: 6, a polynucleotide sequence with at least 85% identity to the sequence set forth in SEQ ID NO: 8, a polynucleotide sequence with at least 85% identity to the sequence set forth in SEQ ID NO: 23, a polynucleotide sequence with at least 85% identity to the sequence set forth in SEQ ID NO: 26 and a polynucleotide sequence with at least 85% identity to the sequence set forth in SEQ ID NO: 28.

6. The expression vector as claimed in claim 4, wherein the expression vector encodes a polypeptide selected from the group consisting of a polypeptide sequence with 100% identity to the sequence set forth in SEQ ID NO: 1, a polypeptide sequence with at least 85% identity to the sequence set forth in SEQ ID NO: 3, a polypeptide sequence with at least 85% identity to the sequence set forth in SEQ ID NO: 5, a polypeptide sequence with at least 85% identity to the sequence set forth in SEQ ID NO: 7, a polypeptide sequence with at least 85% identity to the sequence set forth in SEQ ID NO: 24, a polypeptide sequence with at least 85% identity to the sequence set forth in SEQ ID NO: 25, a polypeptide sequence with at least 85% identity to the sequence set forth in SEQ ID NO: 27 and a polypeptide sequence with at least 85% identity to the sequence set forth in SEQ ID NO: 29.

7. A polynucleotide having a nucleic acid sequence selected from the group consisting of SEQ ID NO: 4, SEQ ID NO: 6, SEQ ID NO: 8, SEQ ID NO: 23, SEQ ID NO: 26 and SEQ ID NO: 28.

8. A method of screening a yeast cell to identify a transformed yeast cell producing clot specific streptokinase, said method comprising:
 (a) transforming at least one yeast cell with the expression vector as claimed in claim 5 to obtain a transformed yeast cell;
 (b) culturing at least one transformed yeast cell in BMMY culture medium with methanol to induce expression of clot specific streptokinase (CSSK) protein,
 (c) separating the culture medium from the transformed yeast cell to obtain a supernatant;
 (d) testing the supernatant for plasminogen activation; and
 (e) identifying a transformed yeast cell producing clot specific streptokinase by detecting plasminogen activation in the supernatant of the cell.

9. The method as claimed in claim 8, wherein the plasminogen activation testing in (d) comprises combining the supernatant with plasminogen and a chromophore and detecting a change in light absorbance at 405 nm.

10. The method as claimed in claim 9, wherein the plasminogen activation is measured against a reference value representing a known quantity of CSSK.

11. The method as claimed in claim 8, further comprising confirming CSSK production in the cell identified in (e) by SDS-PAGE analysis.

12. The expression cassette according to claim 1, wherein the nucleic acid sequence encoding clot specific streptokinase has at least 85% identity to the nucleotide sequence selected from the group consisting of SEQ ID NO: 4, SEQ ID NO: 6 or SEQ ID NO: 8.

13. The expression cassette according to claim 1, wherein the nucleic acid sequence encoding clot specific streptokinase has at least 85% identity to the nucleotide sequence set forth in SEQ ID NO: 4.

14. The expression cassette according to claim 1, wherein the nucleic acid sequence encoding clot specific streptokinase comprises the nucleotide sequence set forth in SEQ ID NO: 4.

15. The expression cassette according to claim 1, wherein the nucleic acid sequence encoding clot specific streptokinase has at least 85% identity to the nucleotide sequence set forth in SEQ ID NO: 6.

16. The expression cassette according to claim 1, wherein the nucleic acid sequence encoding clot specific streptokinase comprises the nucleotide sequence set forth in SEQ ID NO: 6.

17. The expression cassette according to claim 1, wherein the nucleic acid sequence encoding clot specific streptokinase has at least 85% identity to the nucleotide sequence set forth in SEQ ID NO: 8.

18. The expression cassette according to claim 1, wherein the nucleic acid sequence encoding clot specific streptokinase comprises the nucleotide sequence set forth in SEQ ID NO: 8.

19. The expression cassette according to claim 1, wherein the nucleic acid sequence encoding clot specific streptokinase comprises the nucleotide sequence set forth in SEQ ID NO: 2.

\* \* \* \* \*